US011834494B2

(12) United States Patent
Diamond et al.

(10) Patent No.: US 11,834,494 B2
(45) Date of Patent: Dec. 5, 2023

(54) ANTIBODIES TO ZIKA VIRUS AND METHODS OF USE THEREOF

(71) Applicant: Washington University, St. Louis, MO (US)

(72) Inventors: Michael S. Diamond, St. Louis, MO (US); Daved Fremont, St. Louis, MO (US); Haiyan Zhao, St. Louis, MO (US); Estefania Fernandez, St. Louis, MO (US); Derek Platt, St. Louis, MO (US); Christopher Nelson, St. Louis, MO (US)

(73) Assignee: Washington University, St. Louis, MO (US)

( * ) Notice: Subject to any disclaimer, the term of this patent is extended or adjusted under 35 U.S.C. 154(b) by 1024 days.

(21) Appl. No.: 16/320,872

(22) PCT Filed: Jul. 26, 2017

(86) PCT No.: PCT/US2017/044003
§ 371 (c)(1),
(2) Date: Jan. 25, 2019

(87) PCT Pub. No.: WO2018/022786
PCT Pub. Date: Feb. 1, 2018

(65) Prior Publication Data
US 2021/0332111 A1 Oct. 28, 2021

Related U.S. Application Data

(60) Provisional application No. 62/366,782, filed on Jul. 26, 2016.

(51) Int. Cl.
| C07K 16/10 | (2006.01) |
| A61P 31/14 | (2006.01) |
| A61K 39/42 | (2006.01) |
| G01N 33/569 | (2006.01) |
| A61K 39/00 | (2006.01) |

(52) U.S. Cl.
CPC .......... *C07K 16/1081* (2013.01); *A61K 39/42* (2013.01); *A61P 31/14* (2018.01); *G01N 33/56983* (2013.01); *A61K 2039/505* (2013.01); *C07K 2317/34* (2013.01); *C07K 2317/55* (2013.01); *C07K 2317/56* (2013.01); *C07K 2317/622* (2013.01); *C07K 2317/76* (2013.01); *G01N 2333/185* (2013.01)

(58) Field of Classification Search
None
See application file for complete search history.

(56) References Cited

U.S. PATENT DOCUMENTS

| 6,180,370 | B1* | 1/2001 | Queen .................... A61P 31/12 435/69.6 |
| 10,208,107 | B2* | 2/2019 | Ahmed ............ G01N 33/56983 |
| 2008/0268423 | A1* | 10/2008 | Barrett ............. G01N 33/56983 435/5 |
| 2017/0298119 | A1* | 10/2017 | Wollacott ................ A61P 31/14 |

FOREIGN PATENT DOCUMENTS

| WO | 2017181098 A2 | 10/2017 |
| WO | 2018022786 A1 | 2/2018 |

OTHER PUBLICATIONS

Stryer, Biochemistry 4th, WH Freeman, New York. 1995 (Year: 1995).*
Colman, Research in Immunology 145.1 (1994): 33-36 (Year: 1994).*
Kipriyanov, Sergey M., and Fabrice Le Gall. "Generation and production of engineered antibodies." Molecular biotechnology 26.1 (2004): 39-60. (Year: 2004).*
Janeway, Charles A. "Immunobiology: The Immune System in Health and Disease." 2001 (Year: 2001).*
Adams, P. et al., "PHENIX: a comprehensive Python-based system for macromolecular structure solution," Acta Crystallogr. D Biol. Crystallogr., 2010, pp. 213-221, vol. D66.
Al-Lazikani, B. et al., "Standard Conformations for the Canonical Structures of Immunoglobulins," J. Mol. Biol., 1997, pp. 927-948, vol. 273.
Austin, S. et al., "Structural Basis of Differential Neutralization of DENV-1 Genotypes by an Antibody that Recognizes a Cryptic Epitope," PLOS Pathog., Oct. 2012, pp. 1-15, vol. 8, No. 10, e1002930.
Balsitis, S. et al., "Lethal Antibody Enhancement of Dengue Disease in Mice Is Prevented by Fc Modification," PLOS Pathog., Feb. 2010, pp. 1-13, vol. 6, No. 2, e1000790.
Barba-Spaeth, G. et al., "Structural basis of potent Zika-dengue virus antibody cross-neutralization," Nature, Aug. 4, 2016, pp. 48-53, vol. 536.
Baronti, C. et al., "Complete Coding Sequence of Zika Virus from a French Polynesia Outbreak in 2013," Genome Announcements, May/Jun. 2014, pp. 1-2, vol. 2, No. 3, e00500-14.

(Continued)

*Primary Examiner* — Michael Szperka
*Assistant Examiner* — Lia E Taylor
(74) *Attorney, Agent, or Firm* — POLSINELLI PC

(57) ABSTRACT

The present disclosure relates to antibodies specific to Zika virus and methods for detecting Zika virus infection in a subject. The present disclosure also relates to therapeutic antibodies useful in reducing viral load.

8 Claims, 24 Drawing Sheets
(19 of 24 Drawing Sheet(s) Filed in Color)
Specification includes a Sequence Listing.

(56) References Cited

OTHER PUBLICATIONS

Beasley, D. et al., "Identification of Neutralizing Epitopes within Structural Domain III of the West Nile Virus Envelope Protein," J. Virol., Dec. 2002, pp. 13097-13100, vol. 76, No. 24.

Belmusto-Worn, V. et al., "Randomized, Double-Blind, Phase III, Pivotal Field Trial of the Comparative Immunogenicity, Safety, and Tolerability of Two Yellow Fever 17D Vaccines (Arilvax and Yf-Vax) in Healthy Infants and Children in Peru," Am. J. Trop. Med. Hyg., 2005, pp. 189-197, vol. 72, No. 2.

Beltramello, M. et al., "The Human Immune Response to Dengue Virus Is Dominated by Highly Cross-Reactive Antibodies Endowed with Neutralizing and Enhancing Activity," Cell Host & Microbe, Sep. 16, 2010, pp. 271-283, vol. 8.

Block, O. et al., "A tetravalent recombinant dengue domain III protein vaccine stimulates neutralizing and enhancing antibodies in mice," Vaccine, Nov. 29, 2010, pp. 8085-8094, vol. 28, No. 51.

Brasil, P. et al., "Zika Virus Infection in Pregnant Women in Rio de Janeiro—Preliminary Report," N. Engl. J. Med., Dec. 15, 2016, pp. 2321-2334, vol. 375.

Brien, J. et al., "Genotype-Specific Neutralization and Protection by Antibodies against Dengue Virus Type 3," J. Virol., Oct. 2010, pp. 10630-10643, vol. 84, No. 20.

Brien, J. et al., "Propagation, Quantification, Detection, and Storage of West Nile Virus," Curr. Protoc. Microbiol., Nov. 2013, pp. 15D.3.1-15D.3.18, Suppl. 31, John Wiley & Sons, Inc.

Carteaux, G. et al., "Zika Virus Associated with Meningoencephalitis," N. Engl. J. Med., Apr. 21, 2016, pp. 1595-1598, vol. 374, No. 16.

Chan, J. et al., "Zika fever and congenital Zika syndrome: An unexpected emerging arboviral disease," J. Infect., 2016, pp. 507-527, vol. 72.

Chothia, C. et al., "Canonical Structures for the Hypervariable Regions of Immunoglobulins," J. Mol. Bio., 1987, pp. 901-917, vol. 196.

Chothia, C. et al., "Conformations of immunoglobulin hypervariable regions," Nature, Dec. 1989, pp. 877-883, vol. 342.

Co, M. et al., "Humanized antibodies for antiviral therapy," PNAS, Apr. 1991, pp. 2869-2873, vol. 88.

Cockburn, J. et al., "Mechanism of Dengue Virus Broad Cross-Neutralization by a Monoclonal Antibody," Structure, Feb. 8, 2012, pp. 303-314, vol. 20.

Correia, B. et al., "Proof of principle for epitope-focused vaccine design," Nature, Mar. 14, 2014, pp. 201-206, vol. 507.

Cugola, F. et al., "The Brazilian Zika virus strain causes birth defects in experimental models," Nature, Jun. 9, 2016, pp. 267-271, vol. 534.

Dai, L. et al., "Structures of the Zika Virus Envelope Protein and Its Complex with a Flavivirus Broadly Protective Antibody," Cell Host and Microbe, May 11, 2016, pp. 696-704, vol. 19.

De Alwis, R. et al., "Identification of human neutralizing antibodies that bind to complex epitopes on dengue virions," PNAS, May 8, 2012, pp. 7439-7444, vol. 109, No. 19.

Dick, G. et al., "Zika Virus (I). Isolations and Serological Specificity," Trans. R. Soc. Trop. Med. Hyg., Sep. 1952, pp. 509-520, vol. 46, No. 5.

Dick, G., "Zika Virus (II). Pathogenicity and Physical Properties," Trans. R. Soc. Trop. Med. Hyg., Sep. 1952, pp. 521-534, vol. 46, No. 5.

Dowd, K. et al., "A Dynamic Landscape for Antibody Binding Modulates Antibody-Mediated Neutralization of West Nile Virus," PLOS Pathog., Jun. 2011, pp. 1-14, vol. 7, No. 6, e1002111.

Dowd, K. et al., "Genotypic Differences in Dengue Virus Neutralization Are Explained by a Single Amino Acid Mutation That Modulates Virus Breathing," mBio, Nov./Dec. 2015, pp. 1-11, vol. 6, No. 6, e01559-15.

Edeling, M. et al., "Potent Dengue Virus Neutralization by a Therapeutic Antibody with Low Monovalent Affinity Requires Bivalent Engagement," PLOS Pathog., Apr. 2014, pp. 1-10, vol. 10, No. 4, e1004072.

Emsley, P. et al., "Features and development of Coot," Acta Crystallogr. D Biol. Crystallogr., 2010, pp. 486-501, vol. D66.

Evans, P. et al., "How good are my data and what is the resolution?," Acta Crystallogr. D Biol. Crystallogr., 2013, pp. 1204-1214, vol. D69.

Fibriansah, G. et al., "A potent anti-dengue human antibody preferentially recognizes the conformation of E protein monomers assembled on the virus surface," EMBO Mol. Med., 2014, pp. 358-371, vol. 6, No. 3.

GenBank Accession AY947539.1, "Dengue virus type 4 strain H241, complete genome," Mar. 23, 2005; 5 pgs.

GenBank Accession KJ776791.2, "Zika virus strain H/PF/2013, complete genome," Aug. 31, 2016; 5 pgs.

Goncalvez, A. et al., "Monoclonal antibody-mediated enhancement of dengue virus infection in vitro and in vivo and strategies for prevention," PNAS, May 29, 2007, pp. 9422-9427, vol. 104, No. 22.

Goncalvez, A. et al., "Humanized Monoclonal Antibodies Derived from Chimpanzee Fabs Protect against Japanese Encephalitis Virus In Vitro and In Vivo," J. Virol., Jul. 2008, pp. 7009-7021, vol. 82, No. 14.

Grant, A. et al., "Zika Virus Targets Human STAT2 to Inhibit Type I Interferon Signaling," Cell Host & Microbe, Jun. 8, 2016, pp. 882-890, vol. 19.

Gromowski, G. et al., "Characterization of an antigenic site that contains a dominant, type-specific neutralization determinant on the envelope protein domain III (ED3) of dengue 2 virus," Virology, 2007, pp. 349-360, vol. 366.

Hanna, S. et al., "N-Linked Glycosylation of West Nile Virus Envelope Proteins Influences Particle Assembly and Infectivity," J. Virol., Nov. 2005, pp. 13262-13274, vol. 79, No. 21.

Heinz, F. et al., "Field effectiveness of vaccination against tick-borne encephalitis," Vaccine, 2007, pp. 7559-7567, vol. 25.

Heinz, F. et al., "Flaviviruses and their antigenic structure," J. Clin. Virol., Dec. 2012, pp. 289-295, vol. 55, No. 4.

International Search Report and Written Opinion dated Jan. 2, 2018 from related Patent Application No. PCT/US2017/044003; 14 pgs.

Invitation to Pay Additional Fees and, Where Applicable, Protest Fee dated Oct. 23, 2017 from related Patent Application No. PCT/US2017/044003; 2 pgs.

Jarmer, J. et al., "Variation of the Specificity of the Human Antibody Responses after Tick-Borne Encephalitis Virus Infection and Vaccination," J. Virol., Dec. 2014, pp. 13845-13857, vol. 88, No. 23.

Kabsch, W., "XDS," Acta Crystallogr. D Biol. Crystallogr., 2010, pp. 125-132, vol. D66.

Kaufmann, B. et al., "West Nile virus in complex with the Fab fragment of a neutralizing monoclonal antibody," PNAS, Aug. 15, 2006, pp. 12400-12404, vol. 103, No. 33.

Kaufmann, B. et al., "Neutralization of West Nile virus by cross-linking of its surface proteins with Fab fragments of the human monoclonal antibody CR4354," PNAS, Nov. 2, 2010, pp. 18950-18955, vol. 107, No. 44.

Kim, J. et al., "FcRn in the Yolk Sac Endoderm of Mouse Is Required for IgG Transport to Fetus," J. Immunol., 2009, pp. 2583-2589, vol. 182.

Kostyuchenko, V. et al., "Structure of the thermally stable Zika virus," Nature, May 19, 2016, pp. 425-428, vol. 533.

Kuhn, R. et al., "Structure of Dengue Virus: Implications for Flavivirus Organization, Maturation, and Fusion," Cell, Mar. 8, 2002, pp. 717-725, vol. 108.

Lanciotti, R. et al., "Genetic and Serologic Properties of Zika Virus Associated with an Epidemic, Yap State, Micronesia, 2007," Emerg. Infect. Dis., Aug. 2008, pp. 1232-1239, vol. 14, No. 8.

Larocca, R. et al., "Vaccine Protection Against Zika Virus from Brazil," HHS Public Access Author Manuscript, Feb. 25, 2017, pp. 1-24, published in final edited form as: Nature, Aug. 25, 2016, pp. 474-478, vol. 536, No. 7617.

Lawrence, M. et al., "Shape Complementarity at Protein/Protein Interfaces," J. Mol. Biol., Dec. 20, 1993, pp. 946-950, vol. 234, No. 4.

Lazear, H. et al., "A Mouse Model of Zika Virus Pathogenesis," Cell Host & Microbe, May 11, 2016, pp. 720-730, vol. 19.

Lazear, H. et al., "Zika Virus: New Clinical Syndromes and Its Emergence in the Western Hemisphere," J. Virol., May 2016, pp. 4864-4875, vol. 90, No. 10.

(56) References Cited

OTHER PUBLICATIONS

Lee, B. et al., "The Interpretation of Protein Structures: Estimation of Static Accessibility," J. Mol. Biol., 1971, pp. 379-400, vol. 55.
Li, C. et al., "Zika Virus Disrupts Neural Progenitor Development and Leads to Microcephaly in Mice," Cell Stem Cell, 2016, pp. 120-126, vol. 19.
Lok, S. et al., "Binding of a neutralizing antibody to dengue virus alters the arrangement of surface glycoproteins," Nat. Struct. Mol. Biol., Mar. 2008, pp. 312-317, vol. 15, No. 3.
Lucchese, G. et al., "Zika virus and autoimmunity: From microcephaly to Guillain-Barre syndrome, and beyond," Autoimmunity Rev., Aug. 2016, pp. 801-808, vol. 15, No. 8.
Mancia, F. et al., "Optimization of Protein Production in Mammalian Cells with a Coexpressed Fluorescent Marker," Structure, Aug. 2004, pp. 1355-1360, vol. 12.
Martina, B. et al., "Immunization with West Nile virus envelope domain III protects mice against lethal infection with homologous and heterologous virus," Vaccine, Jan. 10, 2008, pp. 153-157, vol. 26, No. 2.
McCoy, A. et al., "Phaser crystallographic software," J. Appl. Cryst., 2007, pp. 658-674, vol. 40.
McDonald, I. et al., "Satisfying Hydrogen Bonding Potential in Proteins," J. Mol. Biol., May 19, 1994, pp. 777-793, vol. 238, No. 5.
Midgley, C. et al., "Structural Analysis of a Dengue Cross-Reactive Antibody Complexed with Envelope Domain III Reveals the Molecular Basis of Cross-Reactivity," J. Immunol., 2012, pp. 4971-4979, vol. 188.
Miner, J. et al., "Zika Virus Infection during Pregnancy in Mice Causes Placental Damage and Fetal Demise," Cell, May 19, 2016, pp. 1081-1091, vol. 165.
NCBI Reference Sequence YP_001527877.1, "flavivirus polyprotein [West Nile virus]," May 24, 2019; 5 pgs.
Nelson, S. et al., "Maturation of West Nile Virus Modulates Sensitivity to Antibody-Mediated Neutralization," PLOS Pathog., May 2008, pp. 1-10, vol. 4, No. 5, e1000060.
Nybakken, G. et al., "Structural basis of West Nile virus neutralization by a therapeutic antibody," Nature, Sep. 29, 2005, pp. 764-768, vol. 437.
Obara, C. et al., "Impact of viral attachment factor expression on antibody-mediated neutralization of flaviviruses," NIH Public Access Author Manuscript, Mar. 1, 2014, pp. 1-17, published in final edited form as: Virol., Mar. 1, 2013, pp. 20-27, vol. 437, No. 1.
Oehler, E. et al., "Zika virus infection complicated by Guillain-Barre syndrome—case report, French Polynesia, Dec. 2013," Euro Surveill., 2014, pp. 1-3, vol. 19, No. 9.
Oliphant, T. et al., "Development of a Humanized Monoclonal Antibody with Therapeutic Potential against West Nile Virus," NIH Public Access Author Manuscript, May 9, 2006, pp. 1-20, published in final edited form as: Nat. Med., May 2005, pp. 522-530, vol. 11, No. 5.
Oliphant, T. et al., "Antibody Recognition and Neutralization Determinants on Domains I and II of West Nile Virus Envelope Protein," J. Virol., Dec. 2006, pp. 12149-12159, vol. 80, No. 24.
Oliphant, T. et al., "Induction of Epitope-Specific Neutralizing Antibodies against West Nile Virus," J. Virol., Nov. 2007, pp. 11828-11839, vol. 81, No. 21.
Pal, P. et al., "Development of a Highly Protective Combination Monoclonal Antibody Therapy against Chikungunya Virus," PLOS Pathog., Apr. 2013, pp. 1-16, vol. 9, No. 4, e1003312.
Pentsuk, N. et al., "An interspecies comparison of placental antibody transfer: New insights into developmental toxicity testing of monoclonal antibodies," Birth Defects Research (Part B), Aug. 2009, pp. 328-344, vol. 86, No. 4.
Pierson, T. et al., "The Stoichiometry of Antibody-Mediated Neutralization and Enhancement of West Nile Virus Infection," Cell Host & Microbe, Apr. 19, 2007, pp. 135-145, vol. 1, No. 2.
Pierson, T. et al., "Structural Insights into the Mechanisms of Antibody-Mediated Neutralization of Flavivirus Infection: Implications for Vaccine Development," Cell Host Microbe, Sep. 11, 2008, pp. 229-238, vol. 4.
Pierson, T. et al., "Molecular mechanisms of antibody-mediated neutralisation of flavivirus infection," NIH Public Access Author Manuscript, Apr. 22, 2009, pp. 1-17, published in final edited form as: Expert. Rev. Mol. Med., 2008, vol. 10, e12.
Pierson, T. et al., "Flaviviruses," In Fields Virology, 2013, D.M. Knipe, and P.M. Howley, eds., Chapter 26, pp. 747-794, Lippincott Williams & Wilkins.
Pierson, T. et al., "A game of numbers: the stoichiometry of antibody-mediated neutralization of flavivirus infection," HHS Public Access Author Manuscript, Jun. 16, 2016, pp. 1-25, published in final edited form as: Prog. Mol. Biol. Transl. Sci., 2015, pp. 141-166, vol. 129.
Rossi, S. et al., "Characterization of a Novel Murine Model to Study Zika Virus," Am. J. Trop. Med. Hyg., 2016, pp. 1362-1369, vol. 94, No. 6.
Rouvinski, A. et al., "Recognition determinants of broadly neutralizing human antibodies against dengue viruses," Nature, Apr. 2, 2015, pp. 109-113, vol. 520.
Sanchez, M. et al., Characterization of neutralizing antibodies to West Nile virus, Virology, 2005, pp. 70-82, vol. 336.
Schneeweiss, A. et al., "A DNA vaccine encoding the E protein of West Nile Virus is protective and can be boosted by recombinant domain DIII," Vaccine, 2011, pp. 6352-6357, vol. 29.
Sheehan, K. et al., "Blocking monoclonal antibodies specific for mouse IFN-alpha/beta receptor subunit 1 (IFNAR-1) from mice immunized by in vivo hydrodynamic transfection," J. Interferon Cytokine Res., 2006, pp. 804-819, vol. 26, No. 11.
Shrestha, B. et al., "The Development of Therapeutic Antibodies That Neutralize Homologous and Heterologous Genotypes of Dengue Virus Type 1," PLOS Pathog., Apr. 2010, pp. 1-18, vol. 6, No. 4, e1000823.
Sirohi, D. et al., "The 3.8 A resolution cryo-EM structure of Zika virus," Sci., Apr. 22, 2016, pp. 467-470, vol. 352, No. 6284.
Smith, S. et al., "The Potent and Broadly Neutralizing Human Dengue Virus-Specific Monoclonal Antibody 1C19 Reveals a Unique Cross-Reactive Epitope on the bc Loop of Domain II of the Envelope Protein," mBio, Nov./Dec. 2013, pp. 1-12, vol. 4, No. 6, e00873-13.
Sukupolvi-Petty, S. et al., "Type- and Sub-Complex-Specific Neutralizing Antibodies against Domain III of Dengue Virus Type-2 Envelope Protein Recognize Adjacent Epitopes," J. Virol., Dec. 2007, pp. 12816-12826, vol. 81, No. 23.
Sukupolvi-Petty, S. et al., "Structure and Function Analysis of Therapeutic Monoclonal Antibodies against Dengue Virus Type 2," J. Virol., Sep. 2010, pp. 9227-9239, vol. 84, No. 18.
Sukupolvi-Petty, S. et al., "Functional Analysis of Antibodies against Dengue Virus Type 4 Reveals Strain-Dependent Epitope Exposure That Impacts Neutralization and Protection," J. Virol., Aug. 2013, pp. 8826-8842, vol. 87, No. 16.
Vogt, M. et al., "Poorly Neutralizing Cross-Reactive Antibodies against the Fusion Loop of West Nile Virus Envelope Protein Protect In Vivo via Fc{gamma} Receptor and Complement-Dependent Effector Mechanisms," J. Virol., Nov. 2011, pp. 11567-11580, vol. 85, No. 22.
Wahala, W. et al., "Natural Strain Variation and Antibody Neutralization of Dengue Serotype 3 Viruses," PLOS Pathog, Mar. 2010, pp. 1-10, vol. 6, No. 3, e1000821.
Williams, K. et al., "Therapeutic Efficacy of Antibodies Lacking Fc{gamma}R against Lethal Dengue Virus Infection Is Due to Neutralizing Potency and Blocking of Enhancing Antibodies," PLOS Pathog., Feb. 2013, pp. 1-17, vol. 9, No. 2, e1003157.
Wu, K. et al., "Structural Basis of a Flavivirus Recognized by Its Neutralizing Antibody," J. Biol. Chem., Nov. 14, 2003, pp. 46007-46013, vol. 278, No. 46.
Zellweger, R. et al., "Enhanced Infection of Liver Sinusoidal Endothelial Cells in a Mouse Model of Antibody-Induced Severe Dengue Disease," Cell Host Microbe, Feb. 18, 2010, pp. 128-139, vol. 7.

(56) References Cited

OTHER PUBLICATIONS

Zhang, X. et al., "Cryo-EM structure of the mature dengue virus at 3.5—A resolution," Nat. Struct. Mol. Biol., Jan. 2013, pp. 105-110, vol. 20, No. 1.
Zhao, H. et al., "Structural Basis of Zika Virus-Specific Antibody Protection," Cell, Aug. 11, 2016, pp. 1016-1027, vol. 166.
Zlatkovic, J. et al., "Aluminum Hydroxide Influences Not Only the Extent but Also the Fine Specificity and Functional Activity of Antibody Responses to Tick-Borne Encephalitis Virus in Mice," J. Virol., Nov. 2013, pp. 12187-12195, vol. 87, No. 22.

\* cited by examiner

Viremia

[Scatter plot: Log$_{10}$ FFU equivalents per mL vs CHK-166, ZV-54, ZV-67. ** significance bars between CHK-166 and ZV-54, and between CHK-166 and ZV-67.]

Days after infection
● CHK-166
■ ZV-54
▽ ZV-67

FIG. 6A

| Summary of mAb somatic mutations | | | |
|---|---|---|---|
| | $V_L$-mutations | $V_H$-mutations | $V_H$-joint insertions |
| ZV-2 | 3 | 12 | 1 |
| ZV-48 | 18 | 13 | 2 |
| ZV-64 | 14 | 4 | 2 |
| ZV-54 | 13 | 15 | 2 |
| ZV-67 | 7 | 10 | 2 |

FIG. 8D

ANTIBODIES TO ZIKA VIRUS AND METHODS OF USE THEREOF

CROSS REFERENCE TO RELATED APPLICATIONS

This application claims the benefit of International Patent Application number PCT/US2017/044003, filed Jul. 26, 2017, which claims the benefit of U.S. Provisional Application No. 62/366,782, filed Jul. 26, 2016, the disclosures of which are hereby incorporated by reference in their entirety.

GOVERNMENTAL RIGHTS

This invention was made with government support under A1077955 and HHSN272201400018C awarded by the National Institutes of Health. The government has certain rights in the invention.

FIELD OF THE INVENTION

The present disclosure relates to antibodies specific to Zika virus and methods for detecting Zika virus infection in a subject. The present disclosure also relates to therapeutic antibodies useful in reducing viral load.

BACKGROUND OF THE INVENTION

Zika virus (ZIKV) is a flavivirus of the Flaviviridae family that is transmitted by Aedes species mosquitoes. ZIKV is closely related to the four serotypes of dengue (DENV) as well as other globally relevant viruses including yellow fever (YFV), West Nile (WNV), and Japanese encephalitis (JEV) viruses (Lazear and Diamond, 2016). Since its identification almost 70 years ago, there were few studies of ZIKV until this past year, when large epidemics in the Americas were accompanied by unexpectedly severe clinical manifestations. Although in most instances ZIKV infection results in a mild febrile illness associated with rash and conjunctivitis, severe neurological phenotypes have been described including Guillain-Barré syndrome and meningoencephalitis. Moreover, infection in pregnant women and mice is now linked causally to fetal abnormalities including microcephaly, spontaneous abortion, and intrauterine growth restriction due to placental insufficiency.

ZIKV infection during pregnancy has emerged as a global public health problem because of its ability to cause severe congenital disease. Thus, there is a need in the art for means to detect and treat Zika virus infection.

BRIEF DESCRIPTION OF THE FIGURES

The application file contains at least one drawing executed in color. Copies of this patent application publication with color drawing(s) will be provided by the Office upon request and payment of the necessary fee.

(FIG. 1A) Specificity pattern of mAb reactivity. Cells were infected with DENV-1, DENV-2, DENV-3, DENV-4, or ZIKV (H/PF/2013), harvested, fixed with paraformaldehyde, and permeabilized. Cells were stained with indicated anti-ZIKV mAbs (ZV-2, ZV-13, ZV-48, ZV-54, ZV-64, and ZV-67) or isotype controls and processed by flow cytometry. The data is representative of several independent experiments. (FIG. 1B) Binding to recombinant proteins. The indicated flavivirus proteins (ZIKV E, ZIKV E-FL [fusion loop mutant], ZIKV DIII, WNV E, and DENV-4 E) were purified (see Methods), adsorbed to 96-well plates, and incubated with the indicated anti-ZIKV MAbs (ZV-2, ZV-13, ZV-48, ZV-54, ZV-64, and ZV-67) or controls (WNV E60 [flavivirus cross-reactive] and WNV E24 [WNV type-specific]. Binding was determined by using an ELISA and the results are representative of two independent experiments performed in triplicate. (FIG. 1C) Neutralization studies. 100 FFU of different ZIKV strains (H/PF/2013, Paraiba 2015, Dakar 41519, and MR-766) were incubated with increasing concentrations of the indicated mAbs in triplicate for 1 h at 37° C. prior to infection of Vero cells. Subsequently, a methylcellulose overlay was added and 40 h later, monolayers were fixed, and stained with 500 ng/ml of ZV-16 (see Methods). Foci were counted and linear regression analysis was performed to generate neutralization curves. The results reflect pooled data from two independent experiments performed in triplicate.

FIG. 2A, FIG. 2B, FIG. 2C, FIG. 2D and FIG. 2E depict graphs showing differential binding and ADE activity of different anti-ZIKV mAbs. (FIG. 2A, FIG. 2B, FIG. 2C) Quantitative analysis of monovalent DIII binding to anti-ZIKV mAbs by BLI. Shown in the top panel are representative binding curves (sensograms) obtained by passing different concentrations of DIII over biotin-labeled anti-ZIKV antibody immobilized on a streptavidin biosensor surface. The kinetic values were obtained by simultaneously fitting the association and dissociation responses to a 1:1 Langmuir binding model (KD, kinetic). The lower panels show the steady-state analysis results for the same BLI data (KD, equilibrium). Plotted in the lower panels (open circles) is the binding response (nm) versus concentration of DIII offered. In each case the binding was saturable. Lower panel insets, Scatchard plots, suggest a single binding affinity for each interaction. The data is representative of two independent experiments per antibody. (FIG. 2D) Binding of anti-ZIKV mAbs to ZIKV SVPs. (Left) ZIKV SVPs were adsorbed to 96-well plates. After washing and blocking of non-specific binding sites, the indicated biotinylated anti-ZIKV (ZV-2, ZV-13, ZV-48, ZV-54, ZV-64, and ZV-67) or control (WNV E60 [flavivirus cross-reactive] and WNV E16 [WNV type-specific] mAbs were added, and binding was measured by ELISA. (Right) The relative avidity of binding was calculated. The binding curves are representative of five independent experiments, and the avidity values reflect the mean of the five experiments. Error bars indicate standard deviations. (FIG. 2E) ADE studies. Serial dilutions of anti-ZIKV (ZV-2, ZV-13, ZV-48, ZV-54, ZV-64, and ZV-67) or control (WNV E60 [flavivirus cross-reactive] and WNV E16 [WNV type-specific] mAbs were mixed with (left) ZIKV H/PF/2013 or (right) DENV-2 RVPs (which encode for GFP) prior to infection of FcγRIIa$^+$ human K562 cells. Cells were harvested 48 hours after infection and processed by flow cytometry. The data is expressed as the percentage of cells expressing GFP as judged by flow cytometry, and one representative experiment of two is shown. Error bars indicate the range of duplicate technical replicates.

(FIG. 3A) Ribbon diagrams of four ZIKV DIII (H/PF/2013) complexes with antibody fragments. The crystal structure of (outer left) ZV-2 Fab (green, elbow angle of 166 degrees), (inner left) ZV-48 scFv (cyan), (inner right) ZV-64 Fab (cyan, elbow angle of 120 degrees), and (outer right) ZV-67 Fab (magenta, elbow angle of 193 degrees) are shown with light chains rendered in paler colors. DIII is colored dark blue with contact segments labeled. (FIG. 3B) Docking of the ZV-2, ZV-48, and ZV-64 complexes onto ZV-67-DIII. DIII is rendered as a molecular surface with each mAbs contact surface color-coded. Simultaneous docking of ZV-2 and ZV-67 with either ZV-48 or ZV-64 buries nearly half of the solvent surface of DIII and creates no van der Waal contacts between adjacent mAbs. (FIG. 3C) ZIKV DIII contains three completely distinct epitopes as defined by binding competition. Five mAbs were probed for competitive and non-competitive binding against the DIII antigen by BLI. In one experiment, biotin-labeled ZV-67 was captured onto the streptavidin sensor, the antibody was then loaded with ZIKV DIII followed by either ZV-54 or ZV-64, and finally ZV-2 was added. In another experiment, ZV-48 was immobilized and ZV-64 or ZV-67 was added after DIII followed by ZV-2. Additional BLI signal indicates an unoccupied epitope (non-competitor), whereas no binding indicates epitope blocking (competition). In this experiment, ZV-48 competed with ZIKV-64 as expected given that they both bind nearly identical epitopes, while ZV-67 competed with its presumed sibling clone ZV-54. A dash (-) represents that no $2^{nd}$ or $3^{rd}$ antibody was offered.

FIG. 4A and FIG. 4B depict sequences and structures to provide a structural definition of ZIKV-specific DIII epitopes. (FIG. 4A) Sequence alignment of DIII from our ZIKV immunizing stains (H/PF/2013 and MR-766), WNV, DENV-1, DENV-2, DENV-3, and DENV-4 and highlighting of structurally defined DIII epitopes. The ABDE sheet epitope of ZV-2 is shown in green, the C-C' loop epitope of ZV-48 and ZV-64 is shown in cyan, and the LR epitope of ZV-67 is shown in magenta. DIII residues are colored if they make van der Waals contact of 3.90-Å distance or less, and the total number of contacts for each epitope residue are shown below the ZIKV sequences. Contact numbers are shown for ZV-48 but not ZV-64 for clarity. For comparison, the same structurally defined DIII epitopes of WNV E16 (magenta, lateral ridge), DV1-E106 (magenta, lateral ridge), DV1-E111 (cyan, C-C' loop), DV2 1A1D-2 (pink, A-strand), DV3 2H12 (light-green, AB-loop), and DV4 4E11 (pink, A-strand) are displayed. The sequence differences at these sites explain the type-specific reactivity of the ZIKV mAbs. The β-strands of the ZIKV secondary structure are labeled and shown in dark blue above the sequence. (FIG. 4B) Delineation of the epitope contact regions on the ZIKV DIII structures of ZV-2 (ABDE sheet), ZV-48 (C-C' loop), ZV-64 (C-C' loop) and ZV-67 (LR). DIII epitope residues are colored as in A, with side chains drawn as sticks and labeled if they make eight or more van der Waals contacts.

FIG. 5A, FIG. 5B, FIG. 5C, FIG. 5D, FIG. 5E and FIG. 5F depict structures showing the accessibility of ZIKV DIII epitopes. (FIG. 5A) Mapping of the three distinct ZIKV DIII epitopes onto the 3.8-Å resolution cryo-electron microscopy structure of the mature virion (SIRE) (Sirohi et al., 2016). The surface distribution of the ABDE sheet (green), C-C' loop (cyan), and LR (magenta) epitopes are rendered on the three symmetrically unique E proteins colored olive, wheat, and grey. While the ABDE sheet and C-C' loop epitopes are dominantly buried in all three symmetry environments, the LR epitope is solvent accessible on the mature virion. (FIG. 5B) Docking of the ZV-2-DIII complex onto the crystal structure of dimeric ZIKV (5JHM) (Dai et al., 2016). Shown above is the ZV-2 Fab docked to a soluble E monomer, which indicates that the ABDE sheet epitope is sterically occluded by DI with severe clashes by the VH domain. Below the ZIKV dimer is depicted, showing how it would sterically clash with the ZV-2 VL domain. ZV-2 CDR loops contact several of the same DIII residues that are contacted by the DII fusion loop in the dimer. (FIG. 5C) Docking of the ZV-64-DIII and ZV-67-DIII complexes onto the cryo-electron microscopy model of the M-E dimer that forms the mature virion (Sirohi et al., 2016). ZV-67 binding to the LR epitope allows for the projection of the Fab away from the viral membrane whereas ZV-64 binding to the C-C' loop epitope positions the Fab in the plane of the viral envelope and membrane. (FIG. 5D) Comparative docking of the DV1-E111 Fab-DIII complex (Austin et al., 2012) onto the cryptic CC' loop epitope suggests similar steric clashes as predicted for ZV-64. (FIG. 5E) Comparative docking of the WNV-E16 Fab-DIII complex (Nybakken et al., 2005) onto the exposed LR epitope indicates unimpeded access, although steric restrictions at the five-fold clustered DIII prevent full occupancy of the mature virion (Kaufmann et al., 2006) this also might be expected for ZV-67 and ZV-54 binding. (FIG. 5F) Comparative docking of the DV2-1A1D-2 Fab-DIII complex (Lok et al., 2008) and DV4-4E11 scFv-DIII complex (Cockburn et al., 2012) onto the exposed A-strand epitope also indicates unimpeded access with both mAbs binding in a highly conserved orientation distinct from that observed for LR engagement by ZV-67 and WNV-E16.

FIG. 6A, FIG. 6B and FIG. 6C depict graphs showing in vivo protection of anti-ZIKV mAbs. Four to five week-old WT C57BL/6 mice were passively transferred 2 mg of anti-Ifnar1 mAb and 250 μg of the indicated mAbs (CHK-166, ZV-54, or ZV-57) via an intraperitoneal injection one day before subcutaneous inoculation with $10^5$ FFU of ZIKV Dakar 41519. (FIG. 6A) On day 3 after infection, serum was collected for analysis of viremia by qRT-PCR. (FIG. 6B) Daily weights were measured. For panels A and B, statistical significance was analyzed by a one-way ANOVA with a Dunnett's multiple comparisons test (, P<0.01; *, P<0.001). (FIG. 6C) Survival curves were constructed. Anti-ZIKV mAbs provided statistically significant protection in the percentage of surviving animals compared to the control CHK-166 mAb (***, P<0.001, log rank test for ZV-54 and ZV-67). The results are pooled from two independent experiments with an n=8-9 mice for each treatment condition.

FIG. 8D depicts a table summarizing the mAb somatic mutations.

DETAILED DESCRIPTION OF THE INVENTION

Figure 1A:
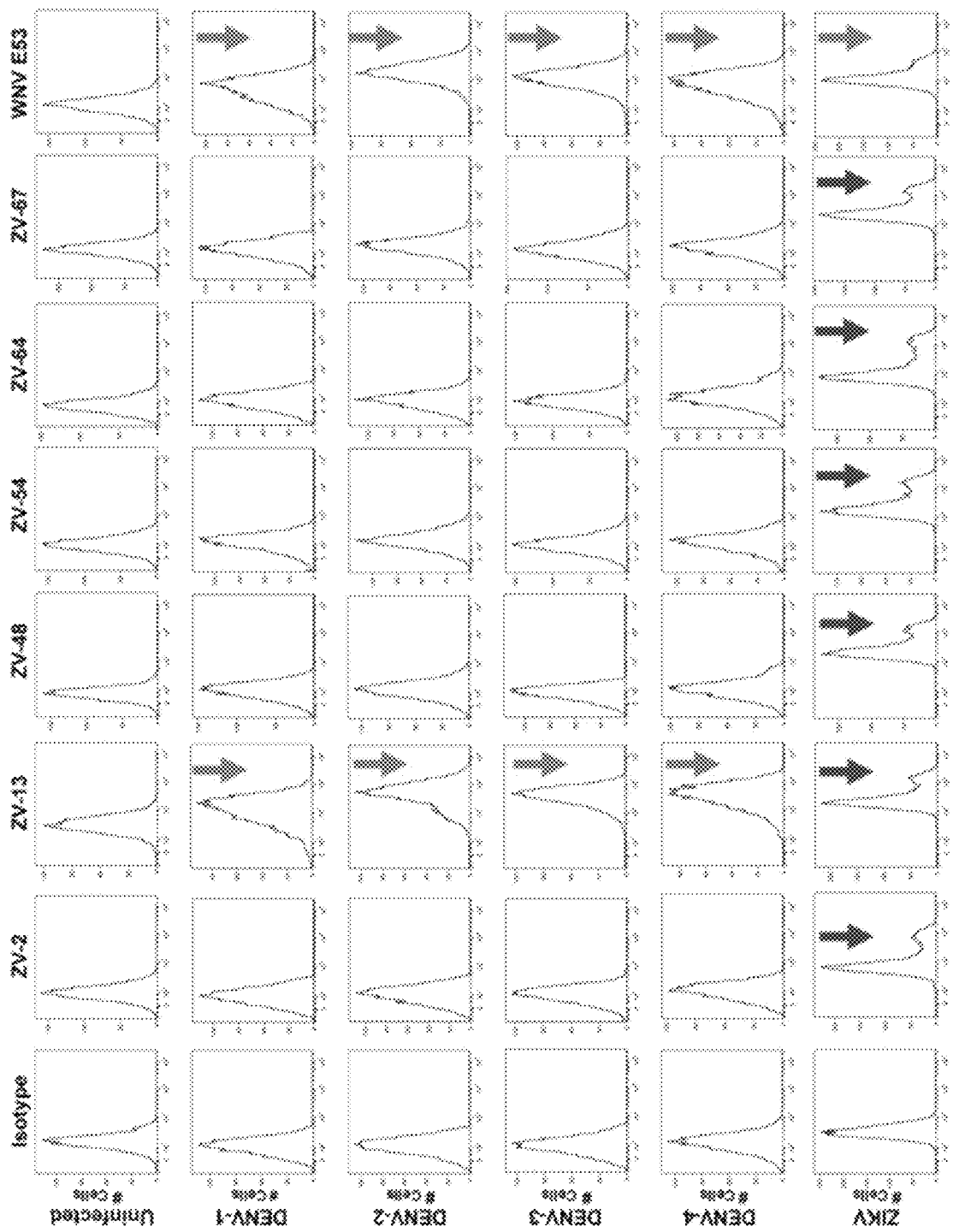
FIG. 1A, FIG. 1B and FIG. 1C depict flow cytometry plots and graphs showing the profile of neutralizing mAbs against ZIKV.

Applicants have developed antibodies and methods of use thereof for detecting Zika virus in a subject. Several of the antibodies specifically bind to defined regions with domain III (DIII) of the E protein of Zika virus. A method of use generally comprises detecting and measuring the amount of Zika virus in a biological sample obtained from a subject using an antigen binding protein of the disclosure. Competition binding and high-resolution X-ray crystallographic analyses of Fab fragments and scFvs defined three spatially distinct epitopes in DIII of the E protein of Zika virus corresponding to the lateral ridge, C-C' loop, and ABDE sheet regions. Further, in vivo passive transfer studies revealed protective activity of DIII-lateral ridge specific neutralizing mAbs in a mouse model of ZIKV infection. These data suggest that DIII is targeted by multiple type-specific antibodies with distinct neutralizing activity, which provides a path for developing prophylactic antibodies for use in pregnancy and designing epitope-specific vaccines against ZIKV. The antigen binding proteins and methods of their use are described in further detail below.

I. Anti-Zika Virus Antigen Binding Proteins

In an aspect, anti-Zika virus antigen binding proteins, also referred to as anti-ZIKV antigen binding proteins, include antigen binding proteins that specifically bind an epitope within domain III (DIII) of the E protein of Zika virus. In certain embodiments, anti-ZIKV antigen binding proteins include antigen binding proteins that specifically bind an epitope within SEQ ID NO:37 or SEQ ID NO:38. In other embodiments, anti-ZIKV antigen binding proteins include antigen binding proteins that specifically bind the lateral ridge (LR), the CC' loop or the ABDE sheet within domain III (DIII) of the E protein of Zika virus. In an embodiment, anti-ZIKV antigen binding proteins include antigen binding proteins that specifically bind the lateral ridge (LR) or the CC' loop within domain III (DIII) of the E protein of Zika virus. In another embodiment, anti-ZIKV antigen binding proteins include antigen binding proteins that specifically bind the lateral ridge (LR) within domain III (DIII) of the E protein of Zika virus. Specifically, anti-ZIKV antigen binding proteins include antigen binding proteins that specifically bind the A-strand, B-C loop, D-E loop and F-G loop within domain III (DIII) of the E protein of Zika virus. More specifically, anti-ZIKV antigen binding proteins include antigen binding proteins that specifically bind one or more sequences selected from the group consisting of SEQ ID NO:45 (TAAFTF), SEQ ID NO:46 (QYAGTDG), SEQ ID NO:47 (SXEN), SEQ ID NO:48 (EKKIT), and SEQ ID NO:49 (DKKIT).

The phrase "specifically binds" herein means antigen binding proteins bind to the protein with an affinity constant or affinity of interaction ($K_D$) of less than 300 nM, less than 250 nM, less than 200 nM, less than 150 nM, less than 100 nM, less than 75 nM, less than 50 nM, less than 25 nM, less than 20 nM, less than 15 nM, less than 10 nM, less than 5 nM, or less than 1 nM. In one embodiment, an anti-ZIKV antigen binding protein binds to an epitope within DIII with a $K_D$ of less than 250 nM. In an embodiment, an anti-ZIKV antigen binding protein binds to an epitope within DIII with a $K_D$ of less than 100 nM. In another embodiment, an anti-ZIKV antigen binding protein binds to an epitope within DIII with a $K_D$ of less than 50 nM. In still another embodiment, an anti-ZIKV antigen binding protein binds to an epitope within DIII with a $K_D$ of less than 20 nM. In still yet another embodiment, an anti-ZIKV antigen binding protein binds to an epitope within DIII with a $K_D$ of less than 10 nM. Methods of determining whether an antigen binding protein binds to DIII of the E protein are known in the art.

The term "antigen binding protein" refers to any form of antibody or fragment thereof that exhibits the desired biological activity. Thus, it is used in the broadest sense and specifically covers monoclonal antibodies (including full length monoclonal antibodies), polyclonal antibodies, multispecific antibodies (e.g. bispecific antibodies), and antibody fragments so long as they exhibit the desired biological activity.

The term "monoclonal antibody" refers to an antibody that is derived from a single copy or clone, including e.g., any eukaryotic, prokaryotic, or phage clone. Monoclonal antibodies are obtained from a population of substantially homogeneous antibodies, i.e., the individual antibodies comprising the population are identical except for possible naturally occurring mutations or post-translational modification that may be present in minor amounts. Monoclonal antibodies are highly specific, being directed against a single antigenic epitope. "Monoclonal antibody" is not limited to antibodies produced through hybridoma technology. Monoclonal antibodies can be produced using e.g., hybridoma techniques well known in the art, as well as recombinant technologies, phage display technologies, synthetic technologies or combinations of such technologies and other technologies readily known in the art. Furthermore, the monoclonal antibody may be labeled with a detectable label, immobilized on a solid phase and/or conjugated with a heterologous compound (e.g., an enzyme or toxin) according to methods known in the art.

The term "fragment thereof" encompasses a fragment or a derivative of an antibody that still substantially retain its biological activity. Therefore, the term "antibody fragment" or "fragment thereof" refers to a portion of a full length antibody, generally the antigen binding or variable region thereof. Examples of an immunologically effective fragment thereof include Fab, Fab', F(ab')$_2$ and Fv fragments, diabodies, linear antibodies, single-chain molecules, and multispecific antibodies formed from antibody fragments. In some contexts herein, fragments will be mentioned specifically for emphasis; nevertheless, it will be understood that regardless of whether fragments are specified, the term "antibody" includes such fragments.

Also included within the definition "antibody" for example are single chain forms, generally designated Fv, regions, of antibodies with this specificity. These scFvs are comprised of the heavy and light chain variable regions connected by a linker. In most instances, but not all, the linker may be a peptide. A linker peptide is preferably from about 10 to 25 amino acids in length. Preferably, a linker peptide is rich in glycine, as well as serine or threonine. ScFvs can be used to facilitate phage display or can be used for flow cytometry, immunohistochemistry, or as targeting domains. Methods of making and using scFvs are known in the art. In a preferred embodiment, the scFvs of the present disclosure are conjugated to a human constant domain. In some embodiments, the heavy constant domain is derived from an IgG domain, such as IgG1, IgG2, IgG3, or IgG4. In other embodiments, the heavy chain constant domain may be derived from IgA, IgM, or IgE.

The term "antibody" also includes bispecific monoclonal antibodies (i.e. a protein that comprises fragments of two different monoclonal antibodies and consequently binds two different antigens). A specific example of a bispecific monoclonal antibody may be a Bi-specific T-cell Engager (BiTE) which is a fusion protein consisting of two single-chain variable fragments (scFvs) of different antibodies. In certain embodiments, BiTEs from a link between T cells and infected cells. Accordingly, one scFv is a specific for Zika virus and one scFv binds a T cell. Additionally, an antibody of the disclosure may be a chimeric antigen receptor (CAR), also referred to as an artificial T cell receptor, a chimeric T cell receptor, or a chimeric immunoreceptor. CARs are engineered receptors, which graft an arbitrary specificity onto an immune effector cell. Typically, these receptors are used to graft the specificity of a monoclonal antibody onto a T cell. Additionally, included within the definition "antibody" are single-domain antibodies, generally designated sdAb, which is an antibody fragment consisting of a single monomeric variable antibody domain. A sdAb antibody may be derived from camelids ($V_HH$ fragments) or cartilaginous fishes ($V_{NAR}$ fragments). As long as the protein retains the ability specifically to bind its intended target, it is included within the term "antibody."

Preferably, but not necessarily, the antibodies useful in the discovery are produced recombinantly, as manipulation of the typically murine or other non-human antibodies with the appropriate specificity is required in order to convert them to humanized form. Antibodies may or may not be glycosylated, though glycosylated antibodies are preferred. Antibodies are properly cross-linked via disulfide bonds, as is known.

The basic antibody structural unit of an antibody useful herein comprises a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acid sequences primarily responsible for antigen recognition. The carboxy-terminal portion of each chain defines a constant region primarily responsible for effector function.

Light chains are classified as gamma, mu, alpha, and lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acid sequences, with the heavy chain also including a "D" region of about 10 more amino acid sequences.

The variable regions of each light/heavy chain pair form the antibody binding site. Thus, an intact antibody has two binding sites, although recombinant versions can be of higher valency. The chains exhibit the same general structure of relatively conserved framework regions (FR) joined by three hypervariable regions, also called complementarity determining regions (hereinafter referred to as "CDRs"). The CDRs from the two chains are aligned by the framework regions, enabling binding to a specific epitope. From N-terminal to C-terminal, both light and heavy chains comprise the domains FR1, CDR1, FR2, CDR2, FR3, CDR3 and FR4 respectively. The assignment of amino acid sequences to each domain is in accordance with known conventions (See, Kabat "Sequences of Proteins of Immunological Interest" National Institutes of Health, Bethesda, Md., 1987 and 1991; Chothia, et al, J. Mol. Bio. (1987) 196:901-917; Chothia, et al., Nature (1989) 342:878-883). For example, Kabat, Chothia, combinations thereof, or other known methods of determining CDRs may be used.

In addition to the specific CDRs, one or more FR regions may also make contact with an antigen as evidenced by the crystal structures disclosed herein. For instance, the tryptophan and/or hisitidine at position 33 and 35, respectively, relative to SEQ ID NO:3 or SEQ ID NO:5 may make contact with the CC' epitope. Also, the methionine at position 50 relative to SEQ ID NO:3 or SEQ ID NO:5 may make contact with the CC' epitope. Additionally, the tyrosine at position 58 relative to SEQ ID NO:7 or SEQ ID NO:9 may make contact with the LR epitope. Further, the arginine at position 94 relative to SEQ ID NO:1 may make contact with the ABDE sheet epitope. Still further, the arginine at position 94 relative to SEQ ID NO:3 may make contact with the CC' epitope. Alternatively, the leucine and/or tyrosine at position 46 and 49, respectively, relative to SEQ ID NO:8 or SEQ ID NO:10 may make contact with the LR epitope.

Additionally, an antibody of the disclosure can be modified to optimize or minimize effector function. Further, an antibody of the disclosure can be modified to extend half-life. Still further, an antibody of the disclosure can be modified to improve binding affinity. Methods of modifying an antibody to improve the aforementioned characteristics are known in the art. For example, the crystal structures disclosed herein may be used to rationally alter amino acids to optimize contact with the antibody and antigen.

In an aspect, monoclonal anti-ZIKV antibodies are generated with appropriate specificity by standard techniques of immunization of mammals, forming hybridomas from the antibody-producing cells of said mammals or otherwise immortalizing them, and culturing the hybridomas or immortalized cells to assess them for the appropriate specificity. In the present case, such antibodies could be generated by immunizing a human, rabbit, rat or mouse, for example, with a peptide representing an epitope encompassing a region of the E protein coding sequence or an appropriate subregion thereof. Specifically, such antibodies could be generated by immunizing a human, rabbit, rat or mouse, for example, with a peptide comprising DIII of the E protein. More specifically, such antibodies could be generated by immunizing a human, rabbit, rat or mouse, for example, with a peptide comprising SEQ ID NO:37 or SEQ ID NO:38. Materials for recombinant manipulation can be obtained by retrieving the nucleotide sequences encoding the desired antibody from the hybridoma or other cell that produces it. These nucleotide sequences can then be manipulated and isolated, characterized, purified and, recovered to provide them in humanized form, for use herein if desired.

As used herein "humanized antibody" includes an anti-ZIKV antibody that is composed partially or fully of amino acid sequences derived from a human antibody germ line by altering the sequence of an antibody having non-human complementarity determining regions ("CDR"). The simplest such alteration may consist simply of substituting the constant region of a human antibody for the murine constant region, thus resulting in a human/murine chimera which may have sufficiently low immunogenicity to be acceptable for pharmaceutical use. Preferably, however, the variable region of the antibody and even the CDR is also humanized by techniques that are by now well known in the art. The framework regions of the variable regions are substituted by the corresponding human framework regions leaving the non-human CDR substantially intact, or even replacing the CDR with sequences derived from a human genome. CDRs may also be randomly mutated such that binding activity and affinity for ZIKV is maintained or enhanced in the context of fully human germline framework regions or framework regions that are substantially human. Substantially human frameworks have at least 90%, 95%, or 99% sequence identity with a known human framework sequence. Fully useful human antibodies are produced in genetically modified mice whose immune systems have been altered to correspond to human immune systems. As mentioned above, it is sufficient for use in the methods of this discovery, to employ an immunologically specific fragment of the antibody, including fragments representing single chain forms.

Further, as used herein the term "humanized antibody" refers to an anti-ZIKV antibody comprising a human framework, at least one CDR from a nonhuman antibody, and in which any constant region present is substantially identical to a human immunoglobulin constant region, i.e., at least about 85-90%, preferably at least 95% identical. Hence, all parts of a humanized antibody, except possibly the CDRs, are substantially identical to corresponding pairs of one or more native human immunoglobulin sequences.

If desired, the design of humanized immunoglobulins may be carried out as follows. When an amino acid sequence falls under the following category, the framework amino acid sequence of a human immunoglobulin to be used (acceptor immunoglobulin) is replaced by a framework amino acid sequence from a CDR-providing nonhuman immunoglobulin (donor immunoglobulin): (a) the amino acid sequence in the human framework region of the acceptor immunoglobulin is unusual for human immunoglobulin at that position, whereas the corresponding amino acid sequence in the donor immunoglobulin is typical for human immunoglobulin at that position; (b) the position of the amino acid sequence is immediately adjacent to one of the CDRs; or (c) any side chain atom of a framework amino acid sequence is within about 5-6 angstroms (center-to-center) of any atom of a CDR amino acid sequence in a three dimensional immunoglobulin model (Queen, et al., op. cit., and Co, ct al, Proc. Natl. Acad. Sci. USA (1991) 88:2869). When each of the amino acid sequences in the human framework region of the acceptor immunoglobulin and a corresponding amino acid sequence in the donor immunoglobulin is unusual for human immunoglobulin at that position, such an amino acid sequence is replaced by an amino acid sequence typical for human immunoglobulin at that position.

The antibodies of the present disclosure may also be conjugated to a payload, such as a therapeutic agent, a detectable, and/or a delivery device (including, but not limited to, a liposome or a nanoparticle) containing the drug or detectable label. Methods of conjugating an antibody to a therapeutic agent, a detectable label, a liposome, a nanoparticle or other delivery device are known in the art. Generally speaking, the conjugation should not interfere with the antibody recognizing its target, and should not interfere with the active site of the target. In some instances, an antibody may be generated with a cleavable linkage between the antibody and the payload. Such a linker may allow release of the payload at a specific cellular location. Suitable linkers include, but are not limited to, amino acid chains and alkyl chains functionalized with reactive groups for conjugating to both the antibody of the disclosure and the detectable label and/or therapeutic agent.

A preferred antibody is a humanized form of mouse antibody derived from a hybridoma designated ZV-2, ZV-48, ZV-64, ZV-67, or ZV-54. As used herein, the term "derived from" means that the "derived" antibody comprises at least one CDR region from the antibody produced by ZV-2, ZV-48, ZV-64, ZV-67, or ZV-54. Stated another way, the "derived antibody" comprises at least one amino acid sequence selected from the group consisting of SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:50, Thr-Ser/Thr-Tyr, or Asn-Tyr-Gly. In a specific embodiment, the "derived antibody" comprises at least one amino acid sequence selected from the group consisting of SEQ ID NO:14, SEQ ID NO:15, SEQ ID NO:19, SEQ ID NO:23, SEQ ID NO:27, SEQ ID NO:31, SEQ ID NO:35, SEQ ID NO:36, SEQ ID NO:50, Thr-Ser/Thr-Tyr, or Asn-Tyr-Gly.

In one embodiment, an antibody of the disclosure may be derived from the hybridoma ZV-2, and may comprise an amino acid sequence with 90, 91, 92, 93, 94, 95, 96, 97, 98, or 99% identity to the heavy chain variable region of SEQ ID NO:1, and/or may comprise an amino acid sequence with 90, 91, 92, 93, 94, 95, 96, 97, 98, or 99% identity to the light chain variable region of SEQ ID NO:2. In another embodiment, an antibody of the disclosure may be derived from the hybridoma ZV-48, and may comprise an amino acid sequence with 90, 91, 92, 93, 94, 95, 96, 97, 98, or 99% identity to the heavy chain variable region of SEQ ID NO:3, and/or may comprise an amino acid sequence with 90, 91, 92, 93, 94, 95, 96, 97, 98, or 99% identity to the light chain variable region of SEQ ID NO:4. In still another embodiment, an antibody of the disclosure may be derived from the hybridoma ZV-64, and may comprise an amino acid sequence with 90, 91, 92, 93, 94, 95, 96, 97, 98, or 99% identity to the heavy chain variable region of SEQ ID NO:5, and/or may comprise an amino acid sequence with 90, 91, 92, 93, 94, 95, 96, 97, 98, or 99% identity to the light chain variable region of SEQ ID NO:6. In still another embodiment, an antibody of the disclosure may be derived from the hybridoma ZV-67, and may comprise an amino acid sequence with 90, 91, 92, 93, 94, 95, 96, 97, 98, or 99% identity to the heavy chain variable region of SEQ ID NO:7, and/or may comprise an amino acid sequence with 90, 91, 92, 93, 94, 95, 96, 97, 98, or 99% identity to the light chain variable region of SEQ ID NO:8. In still yet another embodiment, an antibody of the disclosure may be derived from the hybridoma ZV-54, and may comprise an amino acid sequence with 90, 91, 92, 93, 94, 95, 96, 97, 98, or 99% identity to the heavy chain variable region of SEQ ID NO:9, and/or may comprise an amino acid sequence with 90, 91, 92, 93, 94, 95, 96, 97, 98, or 99% identity to the light chain variable region of SEQ ID NO:10. In each of the above embodiments, the antibody may be humanized.

In an exemplary embodiment, an antibody of the disclosure that binds to DIII of the E protein of Zika virus comprises the heavy chain amino acid sequence of SEQ ID NO:1 and the light chain amino acid sequence of SEQ ID NO:2 [i.e. the monoclonal antibody referred to as ZV-2]. In another exemplary embodiment, an antibody of the disclosure that binds to DIII of the E protein of Zika virus comprises the heavy chain amino acid sequence of SEQ ID NO:3 and the light chain amino acid sequence of SEQ ID NO:4 [i.e. the monoclonal antibody referred to as ZV-48]. In still another exemplary embodiment, an antibody of the disclosure that binds to DIII of the E protein of Zika virus comprises the heavy chain amino acid sequence of SEQ ID NO:5 and the light chain amino acid sequence of SEQ ID NO:6 [i.e. the monoclonal antibody referred to as ZV-64]. In still yet another exemplary embodiment, an antibody of the disclosure that binds to DIII of the E protein of Zika virus comprises the heavy chain amino acid sequence of SEQ ID NO:7 and the light chain amino acid sequence of SEQ ID NO:8 [i.e. the monoclonal antibody referred to as ZV-67]. In a different exemplary embodiment, an antibody of the disclosure that binds to DIII of the E protein of Zika virus comprises the heavy chain amino acid sequence of SEQ ID NO:9 and the light chain amino acid sequence of SEQ ID NO:10 [i.e. the monoclonal antibody referred to as ZV-67].

In one embodiment, an antibody of the disclosure may comprise a light chain CDR1, such as antibody 1, 49, 97, and 146 of Table A. In another embodiment, an antibody of the disclosure may comprise a light chain CDR2, such as antibody 4, 52, 100, and 149 of Table A. In yet another embodiment, an antibody of the disclosure may comprise a light chain CDR3, such as antibody 6, 54, 102, 151, and 196 of Table A. In an alternative embodiment, an antibody of the disclosure may comprise a combination of two or three light chain CDRs, such as the antibodies 2, 3, 5, 50, 51, 53, 98, 99, 101, 147, 148, 150, 194, and 195 of Table A.

Similarly, in one embodiment, an antibody of the disclosure may comprise a heavy chain CDR1, such as antibody 7, 55, 103, 152, 197, and 227 of Table A. In another embodiment, an antibody of the disclosure may comprise a heavy chain CDR2, such as antibody 10, 58, 106, 155, and 230 of Table A. In yet another embodiment, an antibody of the disclosure may comprise a heavy chain CDR3, such as antibody 12, 60, 108, 157, and 232 of Table A. In an alternative embodiment, an antibody of the disclosure may comprise a combination of two or three heavy chain CDRs, such as the antibodies 8, 9, 11, 56, 57, 59, 104, 105, 107, 153, 154, 156, 198, 199, 228, 229, and 231 of Table A.

Alternatively, an antibody of the disclosure may comprise one or more light chain CDRs and one or more heavy chain CDRs, such as the antibodies 13-48, 61-96, 109-145, 158-193, 200-226, and 233-286 of Table A.

TABLE A

| Antibody | Light Chain | | | Heavy Chain | | |
|---|---|---|---|---|---|---|
| | CDR1 | CDR2 | CDR3 | CDR1 | CDR2 | CDR3 |
| 1 | SEQ ID NO: 24 | | | | | |
| 2 | SEQ ID NO: 24 | SEQ ID NO: 28 | | | | |
| 3 | SEQ ID NO: 24 | SEQ ID NO: 28 | SEQ ID NO: 32 | | | |
| 4 | | SEQ ID NO: 28 | | | | |
| 5 | | SEQ ID NO: 28 | SEQ ID NO: 32 | | | |
| 6 | | | SEQ ID NO: 32 | | | |
| 7 | | | | SEQ ID NO: 11 | | |
| 8 | | | | SEQ ID NO: 11 | SEQ ID NO: 16 | |
| 9 | | | | SEQ ID NO: 11 | SEQ ID NO: 16 | SEQ ID NO: 20 |
| 10 | | | | | SEQ ID NO: 16 | |
| 11 | | | | | SEQ ID NO: 16 | SEQ ID NO: 20 |
| 12 | | | | | | SEQ ID NO: 20 |
| 13 | SEQ ID NO: 24 | | | SEQ ID NO: 11 | | |
| 14 | SEQ ID NO: 24 | | | SEQ ID NO: 11 | SEQ ID NO: 16 | |
| 15 | SEQ ID NO: 24 | | | SEQ ID NO: 11 | SEQ ID NO: 16 | SEQ ID NO: 20 |
| 16 | SEQ ID NO: 24 | | | | SEQ ID NO: 16 | |
| 17 | SEQ ID NO: 24 | | | | SEQ ID NO: 16 | SEQ ID NO: 20 |
| 18 | SEQ ID NO: 24 | | | | | SEQ ID NO: 20 |
| 19 | SEQ ID NO: 24 | SEQ ID NO: 28 | | SEQ ID NO: 11 | | |
| 20 | SEQ ID NO: 24 | SEQ ID NO: 28 | | SEQ ID NO: 11 | SEQ ID NO: 16 | |
| 21 | SEQ ID NO: 24 | SEQ ID NO: 28 | | SEQ ID NO: 11 | SEQ ID NO: 16 | SEQ ID NO: 20 |
| 22 | SEQ ID NO: 24 | SEQ ID NO: 28 | | | SEQ ID NO: 16 | |
| 23 | SEQ ID NO: 24 | SEQ ID NO: 28 | | | SEQ ID NO: 16 | SEQ ID NO: 20 |
| 24 | SEQ ID NO: 24 | SEQ ID NO: 28 | | | | SEQ ID NO: 20 |
| 25 | SEQ ID NO: 24 | SEQ ID NO: 28 | SEQ ID NO: 32 | SEQ ID NO: 11 | | |
| 26 | SEQ ID NO: 24 | SEQ ID NO: 28 | SEQ ID NO: 32 | SEQ ID NO: 11 | SEQ ID NO: 16 | |
| 27 | SEQ ID NO: 24 | SEQ ID NO: 28 | SEQ ID NO: 32 | SEQ ID NO: 11 | SEQ ID NO: 16 | SEQ ID NO: 20 |
| 28 | SEQ ID NO: 24 | SEQ ID NO: 28 | SEQ ID NO: 32 | | SEQ ID NO: 16 | |
| 29 | SEQ ID NO: 24 | SEQ ID NO: 28 | SEQ ID NO: 32 | | SEQ ID NO: 16 | SEQ ID NO: 20 |
| 30 | SEQ ID NO: 24 | SEQ ID NO: 28 | SEQ ID NO: 32 | | | SEQ ID NO: 20 |
| 31 | | SEQ ID NO: 28 | | SEQ ID NO: 11 | | |
| 32 | | SEQ ID NO: 28 | | SEQ ID NO: 11 | SEQ ID NO: 16 | |
| 33 | | SEQ ID NO: 28 | | SEQ ID NO: 11 | SEQ ID NO: 16 | SEQ ID NO: 20 |
| 34 | | SEQ ID NO: 28 | | | SEQ ID NO: 16 | |
| 35 | | SEQ ID NO: 28 | | | SEQ ID NO: 16 | SEQ ID NO: 20 |
| 36 | | SEQ ID NO: 28 | | | | SEQ ID NO: 20 |
| 37 | | SEQ ID NO: 28 | SEQ ID NO: 32 | SEQ ID NO: 11 | | |
| 38 | | SEQ ID NO: 28 | SEQ ID NO: 32 | SEQ ID NO: 11 | SEQ ID NO: 16 | |
| 39 | | SEQ ID NO: 28 | SEQ ID NO: 32 | SEQ ID NO: 11 | SEQ ID NO: 16 | SEQ ID NO: 20 |
| 40 | | SEQ ID NO: 28 | SEQ ID NO: 32 | | SEQ ID NO: 16 | |
| 41 | | SEQ ID NO: 28 | SEQ ID NO: 32 | | SEQ ID NO: 16 | SEQ ID NO: 20 |
| 42 | | SEQ ID NO: 28 | SEQ ID NO: 32 | | | SEQ ID NO: 20 |
| 43 | | | SEQ ID NO: 32 | SEQ ID NO: 11 | | |
| 44 | | | SEQ ID NO: 32 | SEQ ID NO: 11 | SEQ ID NO: 16 | |
| 45 | | | SEQ ID NO: 32 | SEQ ID NO: 11 | SEQ ID NO: 16 | SEQ ID NO: 20 |
| 46 | | | SEQ ID NO: 32 | | SEQ ID NO: 16 | |
| 47 | | | SEQ ID NO: 32 | | SEQ ID NO: 16 | SEQ ID NO: 20 |
| 48 | | | SEQ ID NO: 32 | | | SEQ ID NO: 20 |
| 49 | SEQ ID NO: 25 | | | | | |
| 50 | SEQ ID NO: 25 | SEQ ID NO: 29 | | | | |
| 51 | SEQ ID NO: 25 | SEQ ID NO: 29 | SEQ ID NO: 33 | | | |
| 52 | | SEQ ID NO: 29 | | | | |
| 53 | | SEQ ID NO: 29 | SEQ ID NO: 33 | | | |

TABLE A-continued

| Anti-body | Light Chain CDR1 | CDR2 | CDR3 | Heavy Chain CDR1 | CDR2 | CDR3 |
|---|---|---|---|---|---|---|
| 54 | | | SEQ ID NO: 33 | | | |
| 55 | | | | SEQ ID NO: 12 | | |
| 56 | | | | SEQ ID NO: 12 | SEQ ID NO: 17 | |
| 57 | | | | SEQ ID NO: 12 | SEQ ID NO: 17 | SEQ ID NO: 21 |
| 58 | | | | | SEQ ID NO: 17 | |
| 59 | | | | | SEQ ID NO: 17 | SEQ ID NO: 21 |
| 60 | | | | | | SEQ ID NO: 21 |
| 61 | SEQ ID NO: 25 | | | SEQ ID NO: 12 | | |
| 62 | SEQ ID NO: 25 | | | SEQ ID NO: 12 | SEQ ID NO: 17 | |
| 63 | SEQ ID NO: 25 | | | SEQ ID NO: 12 | SEQ ID NO: 17 | SEQ ID NO: 21 |
| 64 | SEQ ID NO: 25 | | | | SEQ ID NO: 17 | |
| 65 | SEQ ID NO: 25 | | | | SEQ ID NO: 17 | SEQ ID NO: 21 |
| 66 | SEQ ID NO: 25 | | | | | SEQ ID NO: 21 |
| 67 | SEQ ID NO: 25 | SEQ ID NO: 29 | | SEQ ID NO: 12 | | |
| 68 | SEQ ID NO: 25 | SEQ ID NO: 29 | | SEQ ID NO: 12 | SEQ ID NO: 17 | |
| 69 | SEQ ID NO: 25 | SEQ ID NO: 29 | | SEQ ID NO: 12 | SEQ ID NO: 17 | SEQ ID NO: 21 |
| 70 | SEQ ID NO: 25 | SEQ ID NO: 29 | | | SEQ ID NO: 17 | |
| 71 | SEQ ID NO: 25 | SEQ ID NO: 29 | | | SEQ ID NO: 17 | SEQ ID NO: 21 |
| 72 | SEQ ID NO: 25 | SEQ ID NO: 29 | | | | SEQ ID NO: 21 |
| 73 | SEQ ID NO: 25 | SEQ ID NO: 29 | SEQ ID NO: 33 | SEQ ID NO: 12 | | |
| 74 | SEQ ID NO: 25 | SEQ ID NO: 29 | SEQ ID NO: 33 | SEQ ID NO: 12 | SEQ ID NO: 17 | |
| 75 | SEQ ID NO: 25 | SEQ ID NO: 29 | SEQ ID NO: 33 | SEQ ID NO: 12 | SEQ ID NO: 17 | SEQ ID NO: 21 |
| 76 | SEQ ID NO: 25 | SEQ ID NO: 29 | SEQ ID NO: 33 | | SEQ ID NO: 17 | |
| 77 | SEQ ID NO: 25 | SEQ ID NO: 29 | SEQ ID NO: 33 | | SEQ ID NO: 17 | SEQ ID NO: 21 |
| 78 | SEQ ID NO: 25 | SEQ ID NO: 29 | SEQ ID NO: 33 | | | SEQ ID NO: 21 |
| 79 | | SEQ ID NO: 29 | | SEQ ID NO: 12 | | |
| 80 | | SEQ ID NO: 29 | | SEQ ID NO: 12 | SEQ ID NO: 17 | |
| 81 | | SEQ ID NO: 29 | | SEQ ID NO: 12 | SEQ ID NO: 17 | SEQ ID NO: 21 |
| 82 | | SEQ ID NO: 29 | | | SEQ ID NO: 17 | |
| 83 | | SEQ ID NO: 29 | | | SEQ ID NO: 17 | SEQ ID NO: 21 |
| 84 | | SEQ ID NO: 29 | | | | SEQ ID NO: 21 |
| 85 | | SEQ ID NO: 29 | SEQ ID NO: 33 | SEQ ID NO: 12 | | |
| 86 | | SEQ ID NO: 29 | SEQ ID NO: 33 | SEQ ID NO: 12 | SEQ ID NO: 17 | |
| 87 | | SEQ ID NO: 29 | SEQ ID NO: 33 | SEQ ID NO: 12 | SEQ ID NO: 17 | SEQ ID NO: 21 |
| 88 | | SEQ ID NO: 29 | SEQ ID NO: 33 | | SEQ ID NO: 17 | |
| 89 | | SEQ ID NO: 29 | SEQ ID NO: 33 | | SEQ ID NO: 17 | SEQ ID NO: 21 |
| 90 | | SEQ ID NO: 29 | SEQ ID NO: 33 | | | SEQ ID NO: 21 |
| 91 | | | SEQ ID NO: 33 | SEQ ID NO: 12 | | |
| 92 | | | SEQ ID NO: 33 | SEQ ID NO: 12 | SEQ ID NO: 17 | |
| 93 | | | SEQ ID NO: 33 | SEQ ID NO: 12 | SEQ ID NO: 17 | SEQ ID NO: 21 |
| 94 | | | SEQ ID NO: 33 | | SEQ ID NO: 17 | |
| 95 | | | SEQ ID NO: 33 | | SEQ ID NO: 17 | SEQ ID NO: 21 |
| 96 | | | SEQ ID NO: 33 | | | SEQ ID NO: 21 |
| 97 | SEQ ID NO: 26 | | | | | |
| 98 | SEQ ID NO: 26 | SEQ ID NO: 30 | | | | |
| 99 | SEQ ID NO: 26 | SEQ ID NO: 30 | SEQ ID NO: 34 | | | |
| 100 | | SEQ ID NO: 30 | | | | |
| 101 | | SEQ ID NO: 30 | SEQ ID NO: 34 | | | |
| 102 | | | SEQ ID NO: 34 | | | |
| 103 | | | | SEQ ID NO: 13 | | |
| 104 | | | | SEQ ID NO: 13 | SEQ ID NO: 18 | |
| 105 | | | | SEQ ID NO: 13 | SEQ ID NO: 18 | SEQ ID NO: 22 |
| 106 | | | | | SEQ ID NO: 18 | |
| 107 | | | | | SEQ ID NO: 18 | SEQ ID NO: 22 |
| 108 | | | | | | SEQ ID NO: 22 |
| 109 | SEQ ID NO: 26 | | | SEQ ID NO: 13 | | |
| 110 | SEQ ID NO: 26 | | | SEQ ID NO: 13 | SEQ ID NO: 18 | |
| 111 | SEQ ID NO: 26 | | | SEQ ID NO: 13 | SEQ ID NO: 18 | SEQ ID NO: 22 |
| 112 | SEQ ID NO: 26 | | | | SEQ ID NO: 18 | |
| 113 | SEQ ID NO: 26 | | | | SEQ ID NO: 18 | SEQ ID NO: 22 |
| 114 | SEQ ID NO: 26 | | | | | SEQ ID NO: 22 |
| 115 | SEQ ID NO: 26 | SEQ ID NO: 30 | | SEQ ID NO: 13 | | |
| 116 | SEQ ID NO: 26 | SEQ ID NO: 30 | | SEQ ID NO: 13 | SEQ ID NO: 18 | |
| 117 | SEQ ID NO: 26 | SEQ ID NO: 30 | | SEQ ID NO: 13 | SEQ ID NO: 18 | SEQ ID NO: 22 |
| 118 | SEQ ID NO: 26 | SEQ ID NO: 30 | | | SEQ ID NO: 18 | |
| 119 | SEQ ID NO: 26 | SEQ ID NO: 30 | | | SEQ ID NO: 18 | SEQ ID NO: 22 |
| 120 | SEQ ID NO: 26 | SEQ ID NO: 30 | | | | SEQ ID NO: 22 |
| 121 | SEQ ID NO: 26 | SEQ ID NO: 30 | SEQ ID NO: 34 | SEQ ID NO: 13 | | |
| 123 | SEQ ID NO: 26 | SEQ ID NO: 30 | SEQ ID NO: 34 | SEQ ID NO: 13 | SEQ ID NO: 18 | |
| 124 | SEQ ID NO: 26 | SEQ ID NO: 30 | SEQ ID NO: 34 | SEQ ID NO: 13 | SEQ ID NO: 18 | SEQ ID NO: 22 |
| 125 | SEQ ID NO: 26 | SEQ ID NO: 30 | SEQ ID NO: 34 | | SEQ ID NO: 18 | |
| 126 | SEQ ID NO: 26 | SEQ ID NO: 30 | SEQ ID NO: 34 | | SEQ ID NO: 18 | SEQ ID NO: 22 |
| 127 | SEQ ID NO: 26 | SEQ ID NO: 30 | SEQ ID NO: 34 | | | SEQ ID NO: 22 |
| 128 | | SEQ ID NO: 30 | | SEQ ID NO: 13 | | |
| 129 | | SEQ ID NO: 30 | | SEQ ID NO: 13 | SEQ ID NO: 18 | |
| 130 | | SEQ ID NO: 30 | | SEQ ID NO: 13 | SEQ ID NO: 18 | SEQ ID NO: 22 |

TABLE A-continued

| Antibody | Light Chain CDR1 | CDR2 | CDR3 | Heavy Chain CDR1 | CDR2 | CDR3 |
|---|---|---|---|---|---|---|
| 131 | | SEQ ID NO: 30 | | | SEQ ID NO: 18 | |
| 132 | | SEQ ID NO: 30 | | | SEQ ID NO: 18 | SEQ ID NO: 22 |
| 133 | | SEQ ID NO: 30 | | | | SEQ ID NO: 22 |
| 134 | | SEQ ID NO: 30 | SEQ ID NO: 34 | SEQ ID NO: 13 | | |
| 135 | | SEQ ID NO: 30 | SEQ ID NO: 34 | SEQ ID NO: 13 | SEQ ID NO: 18 | |
| 136 | | SEQ ID NO: 30 | SEQ ID NO: 34 | SEQ ID NO: 13 | SEQ ID NO: 18 | SEQ ID NO: 22 |
| 137 | | SEQ ID NO: 30 | SEQ ID NO: 34 | | SEQ ID NO: 18 | |
| 138 | | SEQ ID NO: 30 | SEQ ID NO: 34 | | SEQ ID NO: 18 | SEQ ID NO: 22 |
| 139 | | SEQ ID NO: 30 | SEQ ID NO: 34 | | | SEQ ID NO: 22 |
| 140 | | | SEQ ID NO: 34 | SEQ ID NO: 13 | | |
| 141 | | | SEQ ID NO: 34 | SEQ ID NO: 13 | SEQ ID NO: 18 | |
| 142 | | | SEQ ID NO: 34 | SEQ ID NO: 13 | SEQ ID NO: 18 | SEQ ID NO: 22 |
| 143 | | | SEQ ID NO: 34 | | SEQ ID NO: 18 | |
| 144 | | | SEQ ID NO: 34 | | SEQ ID NO: 18 | SEQ ID NO: 22 |
| 145 | | | SEQ ID NO: 34 | | | SEQ ID NO: 22 |
| 146 | SEQ ID NO: 27 | | | | | |
| 147 | SEQ ID NO: 27 | SEQ ID NO: 31 | | | | |
| 148 | SEQ ID NO: 27 | SEQ ID NO: 31 | SEQ ID NO: 35 | | | |
| 149 | | SEQ ID NO: 31 | | | | |
| 150 | | SEQ ID NO: 31 | SEQ ID NO: 35 | | | |
| 151 | | | SEQ ID NO: 35 | | | |
| 152 | | | | SEQ ID NO: 14 | | |
| 153 | | | | SEQ ID NO: 14 | SEQ ID NO: 19 | |
| 154 | | | | SEQ ID NO: 14 | SEQ ID NO: 19 | SEQ ID NO: 23 |
| 155 | | | | | SEQ ID NO: 19 | |
| 156 | | | | | SEQ ID NO: 19 | SEQ ID NO: 23 |
| 157 | | | | | | SEQ ID NO: 23 |
| 158 | SEQ ID NO: 27 | | | SEQ ID NO: 14 | | |
| 159 | SEQ ID NO: 27 | | | SEQ ID NO: 14 | SEQ ID NO: 19 | |
| 160 | SEQ ID NO: 27 | | | SEQ ID NO: 14 | SEQ ID NO: 19 | SEQ ID NO: 23 |
| 161 | SEQ ID NO: 27 | | | | SEQ ID NO: 19 | |
| 162 | SEQ ID NO: 27 | | | | SEQ ID NO: 19 | SEQ ID NO: 23 |
| 163 | SEQ ID NO: 27 | | | | | SEQ ID NO: 23 |
| 164 | SEQ ID NO: 27 | SEQ ID NO: 31 | | SEQ ID NO: 14 | | |
| 165 | SEQ ID NO: 27 | SEQ ID NO: 31 | | SEQ ID NO: 14 | SEQ ID NO: 19 | |
| 166 | SEQ ID NO: 27 | SEQ ID NO: 31 | | SEQ ID NO: 14 | SEQ ID NO: 19 | SEQ ID NO: 23 |
| 167 | SEQ ID NO: 27 | SEQ ID NO: 31 | | | SEQ ID NO: 19 | |
| 168 | SEQ ID NO: 27 | SEQ ID NO: 31 | | | SEQ ID NO: 19 | SEQ ID NO: 23 |
| 169 | SEQ ID NO: 27 | SEQ ID NO: 31 | | | | SEQ ID NO: 23 |
| 170 | SEQ ID NO: 27 | SEQ ID NO: 31 | SEQ ID NO: 35 | SEQ ID NO: 14 | | |
| 171 | SEQ ID NO: 27 | SEQ ID NO: 31 | SEQ ID NO: 35 | SEQ ID NO: 14 | SEQ ID NO: 19 | |
| 172 | SEQ ID NO: 27 | SEQ ID NO: 31 | SEQ ID NO: 35 | SEQ ID NO: 14 | SEQ ID NO: 19 | SEQ ID NO: 23 |
| 173 | SEQ ID NO: 27 | SEQ ID NO: 31 | SEQ ID NO: 35 | | SEQ ID NO: 19 | |
| 174 | SEQ ID NO: 27 | SEQ ID NO: 31 | SEQ ID NO: 35 | | SEQ ID NO: 19 | SEQ ID NO: 23 |
| 175 | SEQ ID NO: 27 | SEQ ID NO: 31 | SEQ ID NO: 35 | | | SEQ ID NO: 23 |
| 176 | | SEQ ID NO: 31 | | SEQ ID NO: 14 | | |
| 177 | | SEQ ID NO: 31 | | SEQ ID NO: 14 | SEQ ID NO: 19 | |
| 178 | | SEQ ID NO: 31 | | SEQ ID NO: 14 | SEQ ID NO: 19 | SEQ ID NO: 23 |
| 179 | | SEQ ID NO: 31 | | | SEQ ID NO: 19 | |
| 180 | | SEQ ID NO: 31 | | | SEQ ID NO: 19 | SEQ ID NO: 23 |
| 181 | | SEQ ID NO: 31 | | | | SEQ ID NO: 23 |
| 182 | | SEQ ID NO: 31 | SEQ ID NO: 35 | SEQ ID NO: 14 | | |
| 183 | | SEQ ID NO: 31 | SEQ ID NO: 35 | SEQ ID NO: 14 | SEQ ID NO: 19 | |
| 184 | | SEQ ID NO: 31 | SEQ ID NO: 35 | SEQ ID NO: 14 | SEQ ID NO: 19 | SEQ ID NO: 23 |
| 185 | | SEQ ID NO: 31 | SEQ ID NO: 35 | | SEQ ID NO: 19 | |
| 186 | | SEQ ID NO: 31 | SEQ ID NO: 35 | | SEQ ID NO: 19 | SEQ ID NO: 23 |
| 187 | | SEQ ID NO: 31 | SEQ ID NO: 35 | | | SEQ ID NO: 23 |
| 188 | | | SEQ ID NO: 35 | SEQ ID NO: 14 | | |
| 189 | | | SEQ ID NO: 35 | SEQ ID NO: 14 | SEQ ID NO: 19 | |
| 190 | | | SEQ ID NO: 35 | SEQ ID NO: 14 | SEQ ID NO: 19 | SEQ ID NO: 23 |
| 191 | | | SEQ ID NO: 35 | | SEQ ID NO: 19 | |
| 192 | | | SEQ ID NO: 35 | | SEQ ID NO: 19 | SEQ ID NO: 23 |
| 193 | | | SEQ ID NO: 35 | | | SEQ ID NO: 23 |
| 194 | SEQ ID NO: 27 | SEQ ID NO: 31 | SEQ ID NO: 36 | | | |
| 195 | | SEQ ID NO: 31 | SEQ ID NO: 36 | | | |
| 196 | | | SEQ ID NO: 36 | | | |
| 197 | | | | SEQ ID NO: 15 | | |
| 198 | | | | SEQ ID NO: 15 | SEQ ID NO: 19 | |
| 199 | | | | SEQ ID NO: 15 | SEQ ID NO: 19 | SEQ ID NO: 23 |
| 200 | SEQ ID NO: 27 | | | SEQ ID NO: 15 | | |
| 201 | SEQ ID NO: 27 | | | SEQ ID NO: 15 | SEQ ID NO: 19 | |
| 202 | SEQ ID NO: 27 | | | SEQ ID NO: 15 | SEQ ID NO: 19 | SEQ ID NO: 23 |
| 203 | SEQ ID NO: 27 | SEQ ID NO: 31 | | SEQ ID NO: 15 | | |
| 204 | SEQ ID NO: 27 | SEQ ID NO: 31 | | SEQ ID NO: 15 | SEQ ID NO: 19 | |
| 205 | SEQ ID NO: 27 | SEQ ID NO: 31 | | SEQ ID NO: 15 | SEQ ID NO: 19 | SEQ ID NO: 23 |
| 206 | SEQ ID NO: 27 | SEQ ID NO: 31 | SEQ ID NO: 36 | SEQ ID NO: 15 | | |

TABLE A-continued

| Anti-body | Light Chain | | | Heavy Chain | | |
|---|---|---|---|---|---|---|
| | CDR1 | CDR2 | CDR3 | CDR1 | CDR2 | CDR3 |
| 207 | SEQ ID NO: 27 | SEQ ID NO: 31 | SEQ ID NO: 36 | SEQ ID NO: 15 | SEQ ID NO: 19 | |
| 208 | SEQ ID NO: 27 | SEQ ID NO: 31 | SEQ ID NO: 36 | SEQ ID NO: 15 | SEQ ID NO: 19 | SEQ ID NO: 23 |
| 209 | SEQ ID NO: 27 | SEQ ID NO: 31 | SEQ ID NO: 36 | | SEQ ID NO: 19 | |
| 210 | SEQ ID NO: 27 | SEQ ID NO: 31 | SEQ ID NO: 36 | | SEQ ID NO: 19 | SEQ ID NO: 23 |
| 211 | SEQ ID NO: 27 | SEQ ID NO: 31 | SEQ ID NO: 36 | | | SEQ ID NO: 23 |
| 212 | | SEQ ID NO: 31 | | SEQ ID NO: 15 | | |
| 213 | | SEQ ID NO: 31 | | SEQ ID NO: 15 | SEQ ID NO: 19 | |
| 214 | | SEQ ID NO: 31 | | SEQ ID NO: 15 | SEQ ID NO: 19 | SEQ ID NO: 23 |
| 215 | | SEQ ID NO: 31 | SEQ ID NO: 36 | SEQ ID NO: 15 | | |
| 216 | | SEQ ID NO: 31 | SEQ ID NO: 36 | SEQ ID NO: 15 | SEQ ID NO: 19 | |
| 217 | | SEQ ID NO: 31 | SEQ ID NO: 36 | SEQ ID NO: 15 | SEQ ID NO: 19 | SEQ ID NO: 23 |
| 218 | | SEQ ID NO: 31 | SEQ ID NO: 36 | | SEQ ID NO: 19 | |
| 219 | | SEQ ID NO: 31 | SEQ ID NO: 36 | | SEQ ID NO: 19 | SEQ ID NO: 23 |
| 220 | | SEQ ID NO: 31 | SEQ ID NO: 36 | | | SEQ ID NO: 23 |
| 221 | | | SEQ ID NO: 36 | SEQ ID NO: 15 | | |
| 222 | | | SEQ ID NO: 36 | SEQ ID NO: 15 | SEQ ID NO: 19 | |
| 223 | | | SEQ ID NO: 36 | SEQ ID NO: 15 | SEQ ID NO: 19 | SEQ ID NO: 23 |
| 224 | | | SEQ ID NO: 36 | | SEQ ID NO: 19 | |
| 225 | | | SEQ ID NO: 36 | | SEQ ID NO: 19 | SEQ ID NO: 23 |
| 226 | | | SEQ ID NO: 36 | | | SEQ ID NO: 23 |
| 227 | | | | Thr-Ser/Thr-Tyr | | |
| 228 | | | | Thr-Ser/Thr-Tyr | SEQ ID NO: 50 | |
| 229 | | | | Thr-Ser/Thr-Tyr | SEQ ID NO: 50 | Asn-Tyr-Gly |
| 230 | | | | | SEQ ID NO: 50 | |
| 231 | | | | | SEQ ID NO: 50 | Asn-Tyr-Gly |
| 232 | | | | | | Asn-Tyr-Gly |
| 233 | SEQ ID NO: 27 | | | Thr-Ser/Thr-Tyr | | |
| 234 | SEQ ID NO: 27 | | | Thr-Ser/Thr-Tyr | SEQ ID NO: 50 | |
| 235 | SEQ ID NO: 27 | | | Thr-Ser/Thr-Tyr | SEQ ID NO: 50 | Asn-Tyr-Gly |
| 236 | SEQ ID NO: 27 | | | | SEQ ID NO: 50 | |
| 237 | SEQ ID NO: 27 | | | | SEQ ID NO: 50 | Asn-Tyr-Gly |
| 238 | SEQ ID NO: 27 | | | | | Asn-Tyr-Gly |
| 239 | SEQ ID NO: 27 | SEQ ID NO: 31 | | Thr-Ser/Thr-Tyr | | |
| 240 | SEQ ID NO: 27 | SEQ ID NO: 31 | | Thr-Ser/Thr-Tyr | SEQ ID NO: 50 | |
| 241 | SEQ ID NO: 27 | SEQ ID NO: 31 | | Thr-Ser/Thr-Tyr | SEQ ID NO: 50 | Asn-Tyr-Gly |
| 242 | SEQ ID NO: 27 | SEQ ID NO: 31 | | | SEQ ID NO: 50 | |
| 243 | SEQ ID NO: 27 | SEQ ID NO: 31 | | | SEQ ID NO: 50 | Asn-Tyr-Gly |
| 244 | SEQ ID NO: 27 | SEQ ID NO: 31 | | | | Asn-Tyr-Gly |
| 245 | SEQ ID NO: 27 | SEQ ID NO: 31 | SEQ ID NO: 35 | Thr-Ser/Thr-Tyr | | |
| 246 | SEQ ID NO: 27 | SEQ ID NO: 31 | SEQ ID NO: 35 | Thr-Ser/Thr-Tyr | SEQ ID NO: 50 | |
| 247 | SEQ ID NO: 27 | SEQ ID NO: 31 | SEQ ID NO: 35 | Thr-Ser/Thr-Tyr | SEQ ID NO: 50 | Asn-Tyr-Gly |
| 248 | SEQ ID NO: 27 | SEQ ID NO: 31 | SEQ ID NO: 35 | | SEQ ID NO: 50 | |
| 249 | SEQ ID NO: 27 | SEQ ID NO: 31 | SEQ ID NO: 35 | | SEQ ID NO: 50 | Asn-Tyr-Gly |
| 250 | SEQ ID NO: 27 | SEQ ID NO: 31 | SEQ ID NO: 35 | | | Asn-Tyr-Gly |
| 251 | | SEQ ID NO: 31 | | Thr-Ser/Thr-Tyr | | |
| 252 | | SEQ ID NO: 31 | | Thr-Ser/Thr-Tyr | SEQ ID NO: 50 | |
| 253 | | SEQ ID NO: 31 | | Thr-Ser/Thr-Tyr | SEQ ID NO: 50 | Asn-Tyr-Gly |
| 254 | | SEQ ID NO: 31 | | | SEQ ID NO: 50 | |
| 255 | | SEQ ID NO: 31 | | | SEQ ID NO: 50 | Asn-Tyr-Gly |
| 256 | | SEQ ID NO: 31 | | | | Asn-Tyr-Gly |
| 257 | | SEQ ID NO: 31 | SEQ ID NO: 35 | Thr-Ser/Thr-Tyr | | |
| 258 | | SEQ ID NO: 31 | SEQ ID NO: 35 | Thr-Ser/Thr-Tyr | SEQ ID NO: 50 | |
| 259 | | SEQ ID NO: 31 | SEQ ID NO: 35 | Thr-Ser/Thr-Tyr | SEQ ID NO: 50 | Asn-Tyr-Gly |
| 260 | | SEQ ID NO: 31 | SEQ ID NO: 35 | | SEQ ID NO: 50 | |
| 261 | | SEQ ID NO: 31 | SEQ ID NO: 35 | | SEQ ID NO: 50 | Asn-Tyr-Gly |
| 262 | | SEQ ID NO: 31 | SEQ ID NO: 35 | | | Asn-Tyr-Gly |
| 263 | | | SEQ ID NO: 35 | Thr-Ser/Thr-Tyr | | |
| 264 | | | SEQ ID NO: 35 | Thr-Ser/Thr-Tyr | SEQ ID NO: 50 | |
| 265 | | | SEQ ID NO: 35 | Thr-Ser/Thr-Tyr | SEQ ID NO: 50 | Asn-Tyr-Gly |
| 266 | | | SEQ ID NO: 35 | | SEQ ID NO: 50 | |
| 267 | | | SEQ ID NO: 35 | | SEQ ID NO: 50 | Asn-Tyr-Gly |
| 268 | | | SEQ ID NO: 35 | | | Asn-Tyr-Gly |
| 269 | SEQ ID NO: 27 | SEQ ID NO: 31 | SEQ ID NO: 36 | Thr-Ser/Thr-Tyr | | |
| 270 | SEQ ID NO: 27 | SEQ ID NO: 31 | SEQ ID NO: 36 | Thr-Ser/Thr-Tyr | SEQ ID NO: 50 | |
| 271 | SEQ ID NO: 27 | SEQ ID NO: 31 | SEQ ID NO: 36 | Thr-Ser/Thr-Tyr | SEQ ID NO: 50 | Asn-Tyr-Gly |
| 272 | SEQ ID NO: 27 | SEQ ID NO: 31 | SEQ ID NO: 36 | | SEQ ID NO: 50 | |
| 273 | SEQ ID NO: 27 | SEQ ID NO: 31 | SEQ ID NO: 36 | | SEQ ID NO: 50 | Asn-Tyr-Gly |
| 274 | SEQ ID NO: 27 | SEQ ID NO: 31 | SEQ ID NO: 36 | | | Asn-Tyr-Gly |
| 275 | | SEQ ID NO: 31 | SEQ ID NO: 36 | Thr-Ser/Thr-Tyr | | |
| 276 | | SEQ ID NO: 31 | SEQ ID NO: 36 | Thr-Ser/Thr-Tyr | SEQ ID NO: 50 | |
| 277 | | SEQ ID NO: 31 | SEQ ID NO: 36 | Thr-Ser/Thr-Tyr | SEQ ID NO: 50 | Asn-Tyr-Gly |
| 278 | | SEQ ID NO: 31 | SEQ ID NO: 36 | | SEQ ID NO: 50 | |
| 279 | | SEQ ID NO: 31 | SEQ ID NO: 36 | | SEQ ID NO: 50 | Asn-Tyr-Gly |
| 280 | | SEQ ID NO: 31 | SEQ ID NO: 36 | | | Asn-Tyr-Gly |
| 281 | | | SEQ ID NO: 36 | Thr-Ser/Thr-Tyr | | |
| 282 | | | SEQ ID NO: 36 | Thr-Ser/Thr-Tyr | SEQ ID NO: 50 | |

TABLE A-continued

| Anti- body | Light Chain | | | Heavy Chain | | |
|---|---|---|---|---|---|---|
| | CDR1 | CDR2 | CDR3 | CDR1 | CDR2 | CDR3 |
| 283 | | | SEQ ID NO: 36 | Thr-Ser/Thr-Tyr | SEQ ID NO: 50 | Asn-Tyr-Gly |
| 284 | | | SEQ ID NO: 36 | | SEQ ID NO: 50 | |
| 285 | | | SEQ ID NO: 36 | | SEQ ID NO: 50 | Asn-Tyr-Gly |
| 286 | | | SEQ ID NO: 36 | | | Asn-Tyr-Gly |

In various embodiments, an antibody of the disclosure is humanized. For instance, in one embodiment, a humanized antibody of the disclosure may comprise a light chain variable region comprising SEQ ID NO:24 with zero to two amino acid substitutions, SEQ ID NO:28 with zero to two amino acid substitutions, and SEQ ID NO:32 with zero to two amino acid substitutions, and/or may comprise a heavy chain variable region comprising SEQ ID NO:11 with zero to two amino acid substitutions, SEQ ID NO:16 with zero to two amino acid substitutions, and SEQ ID NO:20 with zero to two amino acid substitutions. In a preferred embodiment, a humanized antibody of the disclosure may comprise a light chain variable region SEQ ID NO:24 with zero to two amino acid substitutions, SEQ ID NO:28 with zero to two amino acid substitutions, SEQ ID NO:32 with zero to two amino acid substitutions, a heavy chain variable region comprising SEQ ID NO:11 with zero to two amino acid substitutions, SEQ ID NO:16 with zero to two amino acid substitutions, and SEQ ID NO:20 with zero to two amino acid substitutions. In an exemplary embodiment, a humanized antibody of the disclosure may comprise a light chain variable region comprising SEQ ID NO:24, SEQ ID NO:28, SEQ ID NO:32, and a heavy chain variable region comprising SEQ ID NO:11, SEQ ID NO:16, and SEQ ID NO:20. The disclosure also encompasses the corresponding nucleic acid sequences of SEQ ID NO:24, SEQ ID NO:28, SEQ ID NO:32, SEQ ID NO:11, SEQ ID NO:16, and SEQ ID NO:20, which can readily be determined by one of skill in the art, and may be incorporated into a vector or other large DNA molecule, such as a chromosome, in order to express an antibody of the disclosure.

In another embodiment, a humanized antibody of the disclosure may comprise a light chain variable region comprising SEQ ID NO:25 with zero to two amino acid substitutions, SEQ ID NO:29 with zero to two amino acid substitutions, and SEQ ID NO:33 with zero to two amino acid substitutions, and/or may comprise a heavy chain variable region comprising SEQ ID NO:12 with zero to two amino acid substitutions, SEQ ID NO:17 with zero to two amino acid substitutions, and SEQ ID NO:21 with zero to two amino acid substitutions. In a preferred embodiment, a humanized antibody of the disclosure may comprise a light chain variable region SEQ ID NO:25 with zero to two amino acid substitutions, SEQ ID NO:29 with zero to two amino acid substitutions, SEQ ID NO:33 with zero to two amino acid substitutions, a heavy chain variable region comprising SEQ ID NO:12 with zero to two amino acid substitutions, SEQ ID NO:17 with zero to two amino acid substitutions, and SEQ ID NO:21 with zero to two amino acid substitutions. In an exemplary embodiment, a humanized antibody of the disclosure may comprise a light chain variable region comprising SEQ ID NO:25, SEQ ID NO:29, SEQ ID NO:33, and a heavy chain variable region comprising SEQ ID NO:12, SEQ ID NO:17, and SEQ ID NO:21. The disclosure also encompasses the corresponding nucleic acid sequences of SEQ ID NO:25, SEQ ID NO:29, SEQ ID NO:33, SEQ ID NO:12, SEQ ID NO:17, and SEQ ID NO:21, which can readily be determined by one of skill in the art, and may be incorporated into a vector or other large DNA molecule, such as a chromosome, in order to express an antibody of the disclosure.

In still another embodiment, a humanized antibody of the disclosure may comprise a light chain variable region comprising SEQ ID NO:26 with zero to two amino acid substitutions, SEQ ID NO:30 with zero to two amino acid substitutions, and SEQ ID NO:34 with zero to two amino acid substitutions, and/or may comprise a heavy chain variable region comprising SEQ ID NO:13 with zero to two amino acid substitutions, SEQ ID NO:18 with zero to two amino acid substitutions, and SEQ ID NO:22 with zero to two amino acid substitutions. In a preferred embodiment, a humanized antibody of the disclosure may comprise a light chain variable region SEQ ID NO:26 with zero to two amino acid substitutions, SEQ ID NO:30 with zero to two amino acid substitutions, SEQ ID NO:34 with zero to two amino acid substitutions, a heavy chain variable region comprising SEQ ID NO:13 with zero to two amino acid substitutions, SEQ ID NO:18 with zero to two amino acid substitutions, and SEQ ID NO:22 with zero to two amino acid substitutions. In an exemplary embodiment, a humanized antibody of the disclosure may comprise a light chain variable region comprising SEQ ID NO:26, SEQ ID NO:30, SEQ ID NO:34, and a heavy chain variable region comprising SEQ ID NO:13, SEQ ID NO:18, and SEQ ID NO:22. The disclosure also encompasses the corresponding nucleic acid sequences of SEQ ID NO:26, SEQ ID NO:30, SEQ ID NO:34, SEQ ID NO:13, SEQ ID NO:18, and SEQ ID NO:22, which can readily be determined by one of skill in the art, and may be incorporated into a vector or other large DNA molecule, such as a chromosome, in order to express an antibody of the disclosure.

In still yet another embodiment, a humanized antibody of the disclosure may comprise a light chain variable region comprising SEQ ID NO:27 with zero to two amino acid substitutions, SEQ ID NO:31 with zero to two amino acid substitutions, and SEQ ID NO:35 with zero to two amino acid substitutions, and/or may comprise a heavy chain variable region comprising SEQ ID NO:14 with zero to two amino acid substitutions, SEQ ID NO:19 with zero to two amino acid substitutions, and SEQ ID NO:23 with zero to two amino acid substitutions. In a preferred embodiment, a humanized antibody of the disclosure may comprise a light chain variable region SEQ ID NO:27 with zero to two amino acid substitutions, SEQ ID NO:31 with zero to two amino acid substitutions, SEQ ID NO:35 with zero to two amino acid substitutions, a heavy chain variable region comprising SEQ ID NO:14 with zero to two amino acid substitutions, SEQ ID NO:19 with zero to two amino acid substitutions, and SEQ ID NO:23 with zero to two amino acid substitutions. In an exemplary embodiment, a humanized antibody of the disclosure may comprise a light chain variable region comprising SEQ ID NO:27, SEQ ID NO:31, SEQ ID NO:35, and a heavy chain variable region comprising SEQ ID NO:14, SEQ ID NO:19, and SEQ ID NO:23. The disclosure also encompasses the corresponding nucleic acid sequences of SEQ ID NO:27, SEQ ID NO:31, SEQ ID NO:35, SEQ ID NO:14, SEQ ID NO:19, and SEQ ID NO:23, which can readily be determined by one of skill in the art, and may be incorporated into a vector or other large DNA molecule, such as a chromosome, in order to express an antibody of the disclosure.

In other embodiments, a humanized antibody of the disclosure may comprise a light chain variable region comprising SEQ ID NO:27 with zero to two amino acid substitutions, SEQ ID NO:31 with zero to two amino acid substitutions, and SEQ ID NO:35 with zero to two amino acid substitutions, and/or may comprise a heavy chain variable region comprising SEQ ID NO:15 with zero to two amino acid substitutions, SEQ ID NO:19 with zero to two amino acid substitutions, and SEQ ID NO:23 with zero to two amino acid substitutions. In a preferred embodiment, a humanized antibody of the disclosure may comprise a light chain variable region SEQ ID NO:27 with zero to two amino acid substitutions, SEQ ID NO:31 with zero to two amino acid substitutions, SEQ ID NO:36 with zero to two amino acid substitutions, a heavy chain variable region comprising SEQ ID NO:15 with zero to two amino acid substitutions, SEQ ID NO:19 with zero to two amino acid substitutions, and SEQ ID NO:23 with zero to two amino acid substitutions. In an exemplary embodiment, a humanized antibody of the disclosure may comprise a light chain variable region comprising SEQ ID NO:27, SEQ ID NO:31, SEQ ID NO:36, and a heavy chain variable region comprising SEQ ID NO:15, SEQ ID NO:19, and SEQ ID NO:23. The disclosure also encompasses the corresponding nucleic acid sequences of SEQ ID NO:27, SEQ ID NO:31, SEQ ID NO:36, SEQ ID NO:15, SEQ ID NO:19, and SEQ ID NO:23, which can readily be determined by one of skill in the art, and may be incorporated into a vector or other large DNA molecule, such as a chromosome, in order to express an antibody of the disclosure.

In a different embodiment, a humanized antibody of the disclosure may comprise a light chain variable region comprising SEQ ID NO:27 with zero to two amino acid substitutions, SEQ ID NO:31 with zero to two amino acid substitutions, and SEQ ID NO:35 with zero to two amino acid substitutions, and/or may comprise a heavy chain variable region comprising Thr-Ser/Thr-Tyr, SEQ ID NO:50 (Tyr-X-Arg-XX-Asn, wherein X is any amino acid), and Asn-Tyr-Gly. In a preferred embodiment, a humanized antibody of the disclosure may comprise a light chain variable region SEQ ID NO:27 with zero to two amino acid substitutions, SEQ ID NO:31 with zero to two amino acid substitutions, SEQ ID NO:35 with zero to two amino acid substitutions, a heavy chain variable region comprising Thr-Ser/Thr-Tyr, SEQ ID NO:50 (Tyr-X-Arg-XX-Asn, wherein X is any amino acid), and Asn-Tyr-Gly. In an exemplary embodiment, a humanized antibody of the disclosure may comprise a light chain variable region comprising SEQ ID NO:27, SEQ ID NO:31, SEQ ID NO:35, and a heavy chain variable region comprising Thr-Ser/Thr-Tyr, SEQ ID NO:50 (Tyr-X-Arg-XX-Asn, wherein X is any amino acid), and Asn-Tyr-Gly. The disclosure also encompasses the corresponding nucleic acid sequences of SEQ ID NO:27, SEQ ID NO:31, SEQ ID NO:35, Thr-Ser/Thr-Tyr, SEQ ID NO:50 (Tyr-X-Arg-XX-Asn, wherein X is any amino acid), and Asn-Tyr-Gly, which can readily be determined by one of skill in the art, and may be incorporated into a vector or other large DNA molecule, such as a chromosome, in order to express an antibody of the disclosure.

In another different embodiment, a humanized antibody of the disclosure may comprise a light chain variable region comprising SEQ ID NO:27 with zero to two amino acid substitutions, SEQ ID NO:31 with zero to two amino acid substitutions, and SEQ ID NO:36 with zero to two amino acid substitutions, and/or may comprise a heavy chain variable region comprising Thr-Ser/Thr-Tyr, SEQ ID NO:50 (Tyr-X-Arg-XX-Asn, wherein X is any amino acid), and Asn-Tyr-Gly. In a preferred embodiment, a humanized antibody of the disclosure may comprise a light chain variable region SEQ ID NO:27 with zero to two amino acid substitutions, SEQ ID NO:31 with zero to two amino acid substitutions, SEQ ID NO:36 with zero to two amino acid substitutions, a heavy chain variable region comprising Thr-Ser/Thr-Tyr, SEQ ID NO:50 (Tyr-X-Arg-XX-Asn, wherein X is any amino acid), and Asn-Tyr-Gly. In an exemplary embodiment, a humanized antibody of the disclosure may comprise a light chain variable region comprising SEQ ID NO:27, SEQ ID NO:31, SEQ ID NO:36, and a heavy chain variable region comprising Thr-Ser/Thr-Tyr, SEQ ID NO:50 (Tyr-X-Arg-XX-Asn, wherein X is any amino acid), and Asn-Tyr-Gly. The disclosure also encompasses the corresponding nucleic acid sequences of SEQ ID NO:27, SEQ ID NO:31, SEQ ID NO:36, Thr-Ser/Thr-Tyr, SEQ ID NO:50 (Tyr-X-Arg-XX-Asn, wherein X is any amino acid), and Asn-Tyr-Gly, which can readily be determined by one of skill in the art, and may be incorporated into a vector or other large DNA molecule, such as a chromosome, in order to express an antibody of the disclosure.

The disclosure also encompasses a vector comprising a nucleic acid sequence capable of encoding an antibody of the disclosure. As used herein, a "vector" is defined as a nucleic acid molecule used as a vehicle to transfer genetic material. Vectors include but are not limited to, plasmids, phasmids, cosmids, transposable elements, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus, herpes virus vectors, vaccinia virus vectors, Harvey murine sarcoma virus vectors, murine mammary tumor virus vectors, Rous sarcoma virus vectors. An expression vector encoding an antibody of the disclosure may be delivered to the cell using a viral vector or via a non-viral method of transfer. Viral vectors suitable for introducing nucleic acids into cells include retroviruses, adenoviruses, adeno-associated viruses, rhabdoviruses, and herpes viruses. Non-viral methods of nucleic acid transfer include naked nucleic acid, liposomes, and protein/nucleic acid conjugates. An expression construct encoding an antibody of the disclosure that is introduced to the cell may be linear or circular, may be single-stranded or double-stranded, and may be DNA, RNA, or any modification or combination thereof. The disclosure also encompasses a cell line comprising a vector comprising a nucleic acid sequence capable of encoding an antibody of the disclosure. In certain embodiment, a cell line comprises a vector comprising a nucleic acid sequence capable of encoding one or more sequences selected from the group consisting of SEQ ID NO:51, SEQ ID NO:52, SEQ ID NO:53, SEQ ID NO:54, SEQ ID NO:55, and SEQ ID NO:56. SEQ ID NO:51, SEQ ID NO:52, SEQ ID NO:53, SEQ ID NO:54, SEQ ID NO:55 and SEQ ID NO:56 are germ line sequences and thus may be used to generate an antibody of the disclosure. In certain embodiments, a method of generating an antibody of the disclosure comprises, in part, a cell line comprising a vector comprising a nucleic acid sequence capable of encoding SEQ ID NO:51 and SEQ ID NO:52. In other embodiments, a method of generating an antibody of the disclosure comprises, in part, a cell line comprising a vector comprising a nucleic acid sequence capable of encoding SEQ ID NO:53 and SEQ ID NO:54. In still other embodiments, a method of generating an antibody of the disclosure comprises, in part, a cell line comprising a vector comprising a nucleic acid sequence capable of encoding SEQ ID NO:55 and SEQ ID NO:56. In some embodiments, the cell line is an immortalized cell line. In preferred embodiments, the cell line is a hybridoma. Methods of generating hybridomas capable of producing antibodies are known in the art.

II. Methods

In an aspect, the present disclosure provides anti-ZIKV antigen binding proteins to detect Zika virus in vitro and/or in vivo. For example, anti-ZIKV antigen binding proteins may be used to detect and measure the amount of Zika virus in a biological sample. Alternatively, anti-ZIKV antigen binding proteins may be used to detect and measure the amount of Zika virus in a subject. In another aspect, the present disclosure provides anti-ZIKV antigen binding proteins that can be used to reduce viremia or viral burden in tissues due to Zika virus in a subject. In still another aspect, the present disclosure provides anti-ZIKV antigen binding proteins that can be used to treat a Zika virus infection in a subject. In still yet another aspect, the present disclosure provides anti-ZIKV antigen binding proteins that can be used to protect against a Zika virus infection in a subject.

(a) Methods to Detect and Measure the Amount of Zika Virus

In an aspect, the disclosure provides means to detect Zika virus in a biological sample obtained form a subject. In another aspect, the disclosure provides means to measure the amount of Zika virus in a biological sample obtained from a subject. The method generally comprises (i) detecting and/or measuring the amount of Zika virus in a biological sample obtained from a subject using an antigen binding protein that specifically binds DIII of the E protein or Zika virus. Suitable antigen binding proteins are described above in Section I.

As used herein, the term "biological sample" refers to a sample obtained from a subject. Any biological sample containing Zika virus is suitable. Numerous types of biological samples are known in the art. Suitable biological sample may include, but are not limited to, tissue samples or bodily fluids. Non-limiting examples of suitable bodily fluids include blood, plasma, serum, lung aspirate, pleural fluid, sputum, and amniotic fluid. The fluid may be used "as is", the cellular components may be isolated from the fluid, or a protein fraction may be isolated from the fluid using standard techniques. In other embodiments, the biological sample is a tissue sample such as a tissue biopsy. The biopsied tissue may be fixed, embedded in paraffin or plastic, and sectioned, or the biopsied tissue may be frozen and cryosectioned. Alternatively, the biopsied tissue may be processed into individual cells or an explant, or processed into a homogenate, a cell extract, a membranous fraction, or a protein extract.

Suitable subjects include, but are not limited to, a human, a livestock animal, a companion animal, a lab animal, and a zoological animal. A subject may or may not be known to be infected with Zika virus. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the animal is a laboratory animal. Non-limiting examples of a laboratory animal may include rodents, canines, felines, and non-human primates. In another preferred embodiment, the subject is a human.

As will be appreciated by a skilled artisan, the method of collecting a biological sample can and will vary depending upon the nature of the biological sample and the type of analysis to be performed. Any of a variety of methods generally known in the art may be utilized to collect a biological sample. Generally speaking, the method preferably maintains the integrity of the sample such that Zika virus can be accurately detected and the amount measured according to the disclosure.

Once a sample is obtained, it is processed in vitro to detect and measure the amount of Zika virus using an anti-ZIKV antigen binding protein. All suitable methods for detecting and measuring an amount of protein using an antigen binding protein known to one of skill in the art are contemplated within the scope of the disclosure. Methods for detecting and measuring an amount of protein using an antigen binding protein (i.e. "antibody-based methods") are well known in the art. Non-limiting examples include an ELISA, an immunoassay, a competitive immunoassay, a sandwich immunoassay, a radioimmunoassay, an immunoblot or Western blot, flow cytometry, immunohistochemistry, Microfluidic chip based assays, and an array.

In general, an antibody-based method of detecting and measuring an amount of Zika virus comprises contacting some of the sample, or all of the sample, comprising Zika virus with an anti-ZIKV antigen binding protein under conditions effective to allow for formation of a complex between the antigen binding protein and the E protein of Zika virus. Typically, the entire sample is not needed, allowing one skilled in the art to repeatedly detect and measure the amount of Zika virus in the sample. The method may occur in solution, or the antigen binding protein or Zika virus E protein comprising the sample may be immobilized on a solid surface. Non-limiting examples of suitable surfaces may include microtitre plates, test tubes, slides, beads, resins, and other polymers. Attachment to the substrate may occur in a wide variety of ways, as will be appreciated by those in the art. For example, the substrate and the antigen binding protein may be derivatized with chemical functional groups for subsequent attachment of the two. For example, the substrate may be derivatized with a chemical functional group including, but not limited to, amino groups, carboxyl groups, oxo groups or thiol groups. Using these functional groups, the antigen binding protein may be attached directly using the functional groups or indirectly using linkers. An anti-ZIKV antigen binding protein may also be attached to the substrate non-covalently. For example, a biotinylated anti-ZIKV antigen binding protein may be prepared, which may bind to surfaces covalently coated with streptavidin, resulting in attachment. Alternatively, an antigen binding protein may be synthesized on the surface using techniques such as photopolymerization and photolithography.

Contacting the sample with an antigen binding protein under effective conditions for a period of time sufficient to allow formation of a complex generally involves adding the anti-ZIKV antigen binding protein composition to the sample and incubating the mixture for a period of time long enough for the anti-ZIKV antigen binding protein to bind to any antigen present. After this time, the complex will be washed and the complex may be detected and the amount measured by any method well known in the art. Methods of detecting and measuring an amount of an antigen binding protein-polypeptide complex are generally based on the detection of a label or marker. The term "label", as used herein, refers to any substance attached to an antibody, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, stretpavidin, protein A, protein G, antibodies or fragments thereof, polyhistidine, $Ni^{2+}$, Flag tags, myc tags, heavy metals, and enzymes (including alkaline phosphatase, peroxidase, glucose oxidase, and luciferase). Methods of detecting and measuring an amount of an antigen binding protein-polypeptide complex based on the detection of a label or marker are well known in the art.

In some embodiments, an antibody-based method is an immunoassay. Immunoassays can be run in a number of different formats. Generally speaking, immunoassays can be divided into two categories: competitive immunoassays and non-competitive immunoassays. In a competitive immunoassay, an unlabeled analyte in a sample competes with labeled analyte to bind an antigen binding protein. Unbound analyte is washed away and the bound analyte is measured. In a non-competitive immunoassay, the antigen binding protein is labeled, not the analyte. Non-competitive immunoassays may use one antigen binding protein (e.g. the capture antibody is labeled) or more than one antigen binding protein (e.g. at least one capture antibody which is unlabeled and at least one "capping" or detection antibody which is labeled.) Suitable labels are described above.

In other embodiments, an antibody-based method is an immunoblot or Western blot. In yet other embodiments, an antibody-based method is flow cytometry. In different embodiments, an antibody-based method is immunohistochemistry (IHC). IHC uses an antigen binding protein to detect and quantify antigens in intact tissue samples. The tissue samples may be fresh-frozen and/or formalin-fixed, paraffin-embedded (or plastic-embedded) tissue blocks prepared for study by IHC. Methods of preparing tissue block for study by IHC, as well as methods of performing IHC are well known in the art.

(b) Methods to Treat or Protect against Zika Virus

In other aspects, the disclosure provides a method of treating a Zika virus infection in a subject. The method comprises administering an effective amount of an antigen binding protein of the disclosure to the subject. The term "infection" as used herein includes presence of virus in or on a subject, which, if its replication were inhibited, would result in a benefit to the subject. The term "treat", "treating" or "treatment" as used herein refers to administering an antigen binding protein of the disclosure for prophylactic and/or therapeutic purposes. The term "prophylactic treatment" refers to treating a subject who is not yet infected, but who is susceptible to, or otherwise at a risk of infection. The term "therapeutic treatment" refers to administering treatment to a subject already suffering from infection. The term "treat", "treating" or "treatment" as used herein also refers to administering an antigen binding protein of the disclosure in order to: (i) reduce or eliminate either a viral infection or one or more symptoms of the viral infection, or (ii) retard the progression of a viral infection or of one or more symptoms of the viral infection, or (iii) reduce the severity of a viral infection or of one or more symptoms of the viral infection, or (iv) suppress the clinical manifestation of a viral infection, or (v) suppress the manifestation of adverse symptoms of the viral infection. Accordingly, in a specific embodiment, the disclosure provides a method of reducing viremia or viral burden in tissues due to Zika virus in a subject comprising administering an effective amount of an antigen binding protein of the disclosure to the subject. In another specific embodiment, the disclosure provides a method of protecting against a Zika virus infection in a subject comprising administering an effective amount of an antigen binding protein of the disclosure to the subject. The subject and antigen binding protein are described above. In certain embodiments, the pregnant or plans to become pregnant.

In certain aspects, a pharmacologically effective amount of an antigen binding protein of the disclosure, including immunologically reactive fragments, may be administered to a subject. Administration is performed using standard effective techniques, including peripherally (i.e. not by administration into the central nervous system) or locally to the central nervous system. Peripheral administration includes but is not limited to intravenous, intraperitoneal, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners. It may be particularly useful to alter the solubility characteristics of the antigen binding proteins useful in this disclosure, making them more lipophilic, for example, by encapsulating them in liposomes or by blocking polar groups.

Effective peripheral systemic delivery by intravenous or intraperitoneal or subcutaneous injection is a preferred method of administration to a living patient. Suitable vehicles for such injections are straightforward. In addition, however, administration may also be effected through the mucosal membranes by means of nasal aerosols or suppositories. Suitable formulations for such modes of administration are well known and typically include surfactants that facilitate cross-membrane transfer. Such surfactants are often derived from steroids or are cationic lipids, such as N-[1-(2,3-dioleoyl)propyl]-N,N,N-trimethyl ammonium chloride (DOTMA) or various compounds such as cholesterol hemisuccinate, phosphatidyl glycerols and the like.

The concentration of antigen binding protein in formulations to be administered is an effective amount and ranges from as low as about 0.1% by weight to as much as about 15 or about 20% by weight and will be selected primarily based on fluid volumes, viscosities, and so forth, in accordance with the particular mode of administration selected if desired. A typical composition for injection to a living patient could be made up to contain 1 mL sterile buffered water of phosphate buffered saline and about 1-1000 mg of any one of or a combination of the humanized antigen binding protein of the present disclosure. In a specific embodiment, the antigen binding protein composition may have 100-300 mg of antigen binding protein per administration. The formulation could be sterile filtered after making the formulation, or otherwise made microbiologically acceptable. A typical composition for intravenous infusion could have volumes between 1-250 mL of fluid, such as sterile Ringer's solution, and 1-100 mg per ml, or more in anti-ZIKV antigen binding protein concentration. Therapeutic agents of the discovery can be frozen or lyophilized for storage and reconstituted in a suitable sterile carrier prior to use. Lyophilization and reconstitution may lead to varying degrees of antigen binding protein activity loss (e.g. with conventional immune globulins, IgM antibodies tend to have greater activity loss than IgG antibodies). Dosages administered are effective dosages and may have to be adjusted to compensate. The pH of the formulations generally pharmaceutical grade quality, will be selected to balance antigen binding protein stability (chemical and physical) and comfort to the patient when administered. Generally, a pH between 4 and 8 is tolerated. Doses will vary from individual to individual based on size, weight, and other physiobiological characteristics of the individual receiving the successful administration.

The term "effective amount" as used herein refers to an amount, which has a therapeutic effect or is the amount required to produce a therapeutic effect in a subject. For example, a therapeutically or pharmaceutically effective amount of a composition of the disclosure is the amount of antigen binding protein required to produce a desired therapeutic effect as may be judged by clinical trial results, model animal infection studies, and/or in vitro studies (e.g. cell lines). The effective or pharmaceutically effective amount depends on several factors, including but not limited to, the virus involved, characteristics of the subject (for example height, weight, sex, age and medical history), severity of infection, and the composition used. For prophylactic treatments, a therapeutically or prophylactically effective amount is that amount which would be effective to prevent an infection or prevent an interferon-induced immune response. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine. In an aspect, a typical dose contains from about 0.01 mg/kg to about 100 mg/kg of an anti-ZIKV antigen binding protein described herein. Doses can range from about 0.05 mg/kg to about 50 mg/kg, more preferably from about 0.1 mg/kg to about 25 mg/kg.

The frequency of dosing may be daily or once, twice, three times or more per week or per month, as needed as to effectively treat the symptoms. The timing of administration of the treatment relative to the infection and duration of treatment will be determined by the circumstances surrounding the case. Treatment could begin immediately. Treatment could begin in a hospital or clinic itself, or at a later time after discharge from the hospital or after being seen in an outpatient clinic. Duration of treatment could range from a single dose administered on a one-time basis to a life-long course of therapeutic treatments.

Although the foregoing methods appear the most convenient and most appropriate and effective for administration of proteins such as humanized antigen binding proteins, by suitable adaptation, other effective techniques for administration, such as intraventricular administration, transdermal administration and oral administration may be employed provided proper formulation is utilized herein. In addition, it may be desirable to employ controlled release formulations using biodegradable films and matrices, or osmotic mini-pumps, or delivery systems based on dextran beads, alginate, or collagen.

Additionally, the antigen binding proteins disclosed herein may be used in combination with standard treatment for Zika virus infection or standard treatment for symptoms associated with viral infections.

In a different aspect, the disclosure provides a method of immunizing a subject against Zika virus. The method generally comprises administering to the subject an effective amount of a composition comprising a peptide comprising domain III (DIII) of the E protein of Zika virus. In certain embodiments, the composition comprises a peptide comprising SEQ ID NO:37 or SEQ ID NO:38. In other embodiments, the composition comprises a peptide comprising the lateral ridge (LR), the CC' loop or the ABDE sheet within domain III (DIII) of the E protein of Zika virus. In an embodiment, the composition comprises a peptide comprising the lateral ridge (LR) or the CC' loop within domain III (DIII) of the E protein of Zika virus. In another embodiment, the composition comprises a peptide comprising the lateral ridge (LR) within domain III (DIII) of the E protein of Zika virus. Specifically, the composition comprises a peptide comprising the A-strand, B-C loop, D-E loop and F-G loop within domain III (DIII) of the E protein of Zika virus. More specifically, the composition comprises a peptide comprising one or more sequences selected from the group consisting of SEQ ID NO:45 (TAAFTF), SEQ ID NO:46 (QYAGTDG), SEQ ID NO:47 (SXEN), SEQ ID NO:48 (EKKIT), and SEQ ID NO:49 (DKKIT). The subject, administration and composition may be as described above. Following administering of the composition a subject is protected from Zika virus infection. Protection may mean that the subject is not infected with Zika virus. Alternatively, protection may mean that the subject can be infected; however, the severity of a viral infection or of one or more symptoms of the viral infection is reduced. Further, protection may mean that the subject can be infected with Zika virus; however, the manifestation of adverse symptoms of the viral infection is suppressed. Accordingly, the disclosure provided a peptide-based vaccine comprising one or more peptides within domain III (DIII) of the E protein of Zika virus as described above. The peptide can comprise consecutive amino acids from DIII or the peptide can comprise immunogenic regions of DIII pieced together. Methods known in the art may be used to efficiently display the relavent regions of the peptide to elicit a substantiative immune response.

TABLE B

| SEQ ID NO: | Description | SEQUENCE |
|---|---|---|
| 1 | ZIKV-2H | QVQLQESGAELMKPGASVKLSCKTSGYTFIG YWIEWLKQRPGHGLEWVGEIFPGSGRTKYNE KFKGRATFTADTSSNMAYMQLSSLTTEDSAI YYCARYYYGSYYALDYWGQGTSVTVSS |

TABLE B-continued

| SEQ ID NO: | Description | SEQUENCE |
|---|---|---|
| 2 | ZIKV-2L | DIVMTQSPSSLSVSAGEKVTLSCKSSQSLLH SGNQKNYLAWYQQKPGQAPKLLIYGASTRES GVPDRFTGSGSGTDFTLTISSVQAEDLAVYY CQNDHSYPLTFGAGTKLELK |
| 3 | ZIKV-48H | QVQLQQPGAELLKPGASVKLSCKASGYSFSN YWMHWVKQRPGQGPEWIGMIHPNSGNTKYNE KFKNKATLTVDKSSSMVYMQLSSLTSEDSAV FYCARLGNDMDYWGQGTSVTVSS |
| 4 | ZIKV-48L | DIVMSQSPSSLAVSVGEKITMSCKSSQSLLY SNNEKNYLAWYQQKPGQSPKLLIYWASARDS GVPDRFTGSGSGTDFTLTISSVKAEDLAVFY CQQYYSYPYTFGGGTKLEIK |
| 5 | ZIKV-64H | QVQLQQPGAELVKPGASVKLSCKASGYTFTS SWMHWVKQRPGQGLEWIGMIHPNSGSTNYNE KFKNKATLTVDKSSSTAYMQLSSLTSEDSAV YYCARYYYDYDGMDYWGQGTSVTVSS |
| 6 | ZIKV-64L | DIVMSQSPSSLAVSVGEKVTMSCKSSQSLLY SSNQKNYLAWYQQKPGQSPKLLIYWASTRES GVPDRFTGSGSGTDFTLTISSVKAEDLAVYY CQQYYTYPYTFGGGTKLEIN |
| 7 | ZIKV-67H | QAQLQQSGTGLARPGASVKLSCKASGYTFTS YGISWVTQRAGQGLEWIGVIYPRSGNTYYNE KFRGKATLTADKSSSSAYMELRGLTAEDSAV YFCARENYGSVYWGQGTTLTVSS |
| 8 | ZIKV-67L | DIVMTQSQKFMSTVGDRVSITCKASQNVGT AVAWYQQKPGQSPKLLIYSASNRYTGVPDRF TGSGSGTDFTLTISNMQSEDLADYFCQQFSS YPYTFGGGTKLEIK |
| 9 | ZIKV-54H | QVQLQQSGVGLARPGTSVKLSCKASGYSFTT YGISWVTQRPGQGLEWIGVIYPRSNNTYYNE RFRGKATLTADKSSSSAYLELRGLTAEDSAV YFCARENYGSVYWGQGTTLTVSS |
| 10 | ZIKV-54L | DIVMTQSQKFMSTVGDRVTITCKASQSVGT AVAWYQKPGQSPKLLIYSASNRYTGVPDRF TGSGSGTDFTLTITYMQSEDLADYFCQQFSN YPFTFGGGTKLEIK |
| 11 | 2H-CDR1 | GYTFIGY |
| 12 | 48H-CDR1 | GYSFSNY |
| 13 | 64H-CDR1 | GYTFTSS |
| 14 | 67H-CDR1 | GYTFTSY |
| 15 | 54H-CDR1 | GYSFTTY |
| 16 | 2H-CDR2 | FPGSGR |
| 17 | 48H-CDR2 | HPNSGN |
| 18 | 64H-CDR2 | HPNSGS |
| 19 | 67H-CDR2 54H-CDR2 | YPRSXN, wherein X is G or N |
| 20 | 2H-CDR3 | YYYGSYYALDY |
| 21 | 48H-CDR3 | LGNDMDY |
| 22 | 64H-CDR3 | YYYDYDGMDY |
| 23 | 67H-CDR3 54H-CDR3 | ENYGSVY |
| 24 | 2L-CDR1 | KSSQSLLHSGNQKNYLA |
| 25 | 48L-CDR1 | KSSQSLLYSNNEKNYLA |
| 26 | 64L-CDR1 | KSSQSLLYSSNQKNYLA |
| 27 | 67L-CDR1 54L-CDR1 | KASQXVGTAVA, wherein X is N or S |
| 28 | 2L-CDR2 | GASTRES |
| 29 | 48L-CDR2 | WASARDS |
| 30 | 64L-CDR2 | WASTRES |
| 31 | 67L-CDR2 54L-CDR2 | SASNRYT |
| 32 | 2L-CDR3 | QNDHSYPLT |
| 33 | 48L-CDR3 | QQYYSYPYT |
| 34 | 64L-CDR3 | QQYYTYPYT |
| 35 | 67L-CDR3 | QQFSSYPYT |
| 36 | 54L-CDR3 | QQFSNYPFT |
| 37 | Zika_FP | KGVSYSLCTAAFTFTKIPAETLHGTVTVEVQ YAGTDGPCKVPAQMAVDMQTLTPVGRLITAN PVITESTENSKMMLELDPPFGDSYIVIGVGE KKITHHWHRSG |
| 38 | Zika_MR766 | KGVSYSLCTAAFTFTKVPAETLHGTVTVEVQ YAGTDGPCKIPVQMAVDMQTLTPVGRLITAN PVITESTENSKMMLELDPPFGDSYIVIGVGD KKITHHWHRSG |
| 39 | WNV_E16 (1ZTX) | KGTTYGVCSKAFKFLGTPADTGHGTVVLELQ YTGTDGPCKVPISSVASLNDLTPVGRLVTVN PFVSVATANAKVLIELEPPFGDSYIVVGRGE QQINHHWHKSG |
| 40 | DV1_E106 (4L5F) | KGMSYVMCTGSFKLEKEVAETQHGTVLVQVK YEGTDAPCKIPFSTQDEKGATQNGRLITANP IVTDKEKPVNIEAEPPFGESYIVVGAGEKAL KLSWFKKG |
| 41 | DV1_E111 (4FFZ) | KGMSYVMCTGSFKLEKEVAETQHGTVLVQVK YEGTDAPCKIPFSSQDEKGVTQNGRLITANP IVTDKEKPVNIEAEPPFGESYIVVGAGEKAL KLSWFKKG |
| 42 | DV2_1A1D-2 (2R29) | KGMSYSMCTGKFKVVKEIAETQHGTIVIRVQ YEGDGSPCKIPFEIMDLEKRHVLGRLITVNP IVTEKDSPVNIEAEPPFGDSYIIIGVEPGQL KLNWFKKG |
| 43 | DV3_2H12 (4ALA) | KGMSYAMCLNTFVLKKEVSETQHGTILIKVE YKGEDAPCKIPFSTEDGQGKAHNGRLITANP VVTKKEEPVNIEAEPPFGESNIVIGIGDKAL KINWYRKG |
| 44 | DV4_4E11 (3UYP) | KGMSYTMCSGKFSIDKEMAETQHGTTVVKVK YEGAGAPCKVPIEIRDVNKEKVVGRIISSTP FAENTNSVTNIELEPPFGDSYIVIGVGDSAL TLHWFRKG |
| 45 | LR epitiope 1 | TAAFTF |
| 46 | LR epitope 2 | QYAGTDG |
| 47 | LR epitope 3 | SXEN, wherein X is any amino acid |
| 48 | LR epitope 4 | EKKIT |

TABLE B-continued

| SEQ ID NO: | Description | SEQUENCE |
|---|---|---|
| 49 | LR epitope 4 | DKKIT |
| 50 | 67H & 54H-CDR2 consensus | YXRXXN, wherein X is any amino acid |
| 51 | J558.6.96/ JH4-2H | QVQLQQSGAELMKPGASVKLSCKATGYTFTG YWIEWVKQRPGHGLEWIGEILPGSGSTNYNE KFKGKATFTADTSSNTAYMQLSSLTTEDSAI YYCARYYYGSYAMDYWGQGTSVTVSS |
| 52 | 8-28/JK5-2L | DIVMTQSPSSLSVSAGEKVTMSCKSSQSLLN SGNQKNYLAWYQQKPGQPPKLLIYGASTRES GVPDRFTGSGSGTDFTLTISSVQAEDLAVYY CQNDHSYPLTFGAGTKLELK |
| 53 | J558.67.166/ JH4-48 & 64H | QVQLQQPGAELVKPGASVKLSCKASGYTFTS YWMHWVKQRPGQGLEWIGMIHPNSGSTNYNE KFKSKATLTVDKSSSTAYMQLSSLTSEDSAV FYCARYYDYDMDYWGQGTSVTVSS |
| 54 | 8-24/JK2-48 & 64L | DIVMTQSPSSLAMSVGQKVTMSCKSSQSLLN SSNQKNYLAWYQQKPGQSPKLLVYFASTRES GVPDRFIGSGSGTDFTLTISSVQAEDLADYF CQQHYSTPYTFGGGTKLEIK |
| 55 | J558.84.190/ JH2-54 & 67H | QVQLQQSGAELARPGASVKLSCKASGYTFTS YGISWVKQRTGQGLEWIGEIYPRSGNTYYNE KFKGKATLTADKSSSTAYMELRSLTSEDSAV YFCARNYGSYWGQGTTLTVSS |
| 56 | 19-23/JK2-54 & 67L | DIVMTQSHKFMSTSVGDRVSITCKASQDVGT AVAWYQQKPGQSPKLLIYWASTRHTGVPDRF TGSGSGTDFTLTISNVQSEDLADYFCQQYSS YPYTFGGGTKLEIK |

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Introduction to the Examples

Zika virus (ZIKV) is a flavivirus of the Flaviviridae family that is transmitted by *Aedes* species mosquitoes. ZIKV was originally identified in 1947 in the Zika forest of Uganda from a sentinel rhesus monkey (Dick, 1952; Dick et al., 1952). ZIKV is closely related to the four serotypes of dengue (DENV) as well as other globally relevant viruses including yellow fever (YFV), West Nile (WNV), and Japanese encephalitis (JEV) viruses (Lazear and Diamond, 2016). Since its identification almost 70 years ago, there were few studies of ZIKV until this past year, when large epidemics in the Americas were accompanied by unexpectedly severe clinical manifestations. Although in most instances ZIKV infection results in a mild febrile illness associated with rash and conjunctivitis, severe neurological phenotypes have been described including Guillain-Barré syndrome and meningoencephalitis (Carteaux et al., 2016; Oehler et al., 2014). Moreover, infection in pregnant women (Brasil et al., 2016) and mice (Cugola et al., 2016; Li et al., 2016; Miner et al., 2016) is now linked causally to fetal abnormalities including microcephaly, spontaneous abortion, and intrauterine growth restriction due to placental insufficiency.

ZIKV is a positive-sense single-stranded RNA virus with a ~11 kilobase open reading frame that is flanked by 5' and 3' non-coding regions. The genome encodes a single polyprotein that is post-translationally cleaved by host and viral proteases into three structural proteins (capsid (C), pre-membrane (prM), and envelope (E)) and seven non-structural proteins. C forms a nucleocapsid when bound to viral RNA, prM complexes with E shortly after synthesis to facilitate folding and prevent premature fusion to host membranes during virion release, and E mediates viral assembly, attachment, entry, and fusion (Lindenbach et al., 2013). Similar to other flaviviruses, the ZIKV E protein can be divided into three domains: a central β-barrel domain (domain I, DI), an extended dimerization domain (DII), and an immunoglobulin-like segment (DIII) (Dai et al., 2016). The distal end of DII contains the fusion loop (FL), a hydrophobic sequence that penetrates the host cell endosomal membrane during the pH-dependent conformational changes that drive fusion. Two high-resolution cryo-electron microscopic structures show that similar to other flaviviruses, mature ZIKV virions are smooth particles that incorporate 180 copies each of the E and cleaved M proteins (Kostyuchenko et al., 2016; Sirohi et al., 2016). Analogous to DENV (Kuhn et al., 2002; Zhang et al., 2013), the E protein of ZIKV is arranged as antiparallel dimers in a herringbone pattern that lie relatively flat against the lipid envelope.

Neutralizing antibodies have important roles in the protection against infection by many flaviviruses (Heinz and Stiasny, 2012; Pierson and Diamond, 2008) and are considered correlates of protection for licensed YFV and tick-borne encephalitis virus (TBEV) vaccines (Belmusto-Worn et al., 2005; Heinz et al., 2007). The E protein is a primary antigenic target of neutralizing antibodies, which bind epitopes in all three structural domains, with many type-specific protective antibodies recognizing determinants in DIII (Beasley and Barrett, 2002; Oliphant et al., 2005; Shrestha et al., 2010; Sukupolvi-Petty et al., 2010). Potently neutralizing anti-flavivirus antibodies also recognize complex quaternary epitopes composed of more than one domain or E protein (de Alwis et al., 2012; Fibriansah et al., 2014; Kaufmann et al., 2010; Rouvinski et al., 2015). In comparison, antibodies that recognize the fusion loop in DII are more cross-reactive and neutralize flaviviruses less efficiently (Pierson et al., 2008), although they may still have protective activity in vivo (Dai et al., 2016; Vogt et al., 2011; Williams et al., 2013).

In this study, we developed six mouse mAbs against ZIKV after immunizing with live virus and boosting with infectious virus or recombinant E proteins. Four of the mAbs (ZV-48, ZV-54, ZV-64, and ZV-67) neutralized infection of African, Asian, and American strains of ZIKV whereas two (ZV-2 and ZV-13) inhibited infection poorly. The neutralizing mAbs bound ZIKV subviral particles (SVPs) more avidly and in greater numbers, which likely contributes to their more potent functional activities. Five of the mAbs (ZV-2, ZV-48, ZV-54, ZV-64, and ZV-67) were ZIKV-specific and bound to DIII whereas one (ZV-13) recognized the fusion loop in DII and was cross-reactive with other flaviviruses including DENV, WNV, and JEV. High-resolution crystal structures were determined for three Fabs and one single chain variable fragment (scFv) bound to DIII, defining three non-overlapping conformational epitopes; the lateral ridge (LR) (ZV-54 and ZV-67), the CC' loop (ZV-48 and ZV-64), and the ABDE sheet (ZV-2). In vivo passive transfer studies in a lethal mouse model of ZIKV infection revealed protective activity of neutralizing DIII LR mAbs. Overall, our results suggest that DIII is targeted by several different type-specific antibodies with distinct neutralizing activities.

Example 1. Generation of mAbs Against ZIKV E Protein

To generate a panel of neutralizing antibodies with broadly inhibitory activity against ZIKV, $Irf3^{-/-}$ mice were serially infected 30 days apart with ZIKV MR-766 (Uganda 1947) and ZIKV H/PF/2013 (French Polynesia 2013). $Irf3^{-/-}$ mice were used instead of wild-type (WT) mice, because ZIKV strains are deficient in evading type I interferon-mediated immunity (Lazear et al., 2016; Rossi et al., 2016) due in part to an inability to antagonize mouse Stat2 (Grant et al., 2016). Three days before myeloma-splenocyte fusion, mice were boosted intravenously with ZIKV H/PF/2013 or recombinant DIII (amino acids 299 to 407 of the ZIKV E protein). After screening ~2,000 hybridomas, six mAbs were isolated that recognized ZIKV E protein by ELISA (Table 1).

Figure 1B:
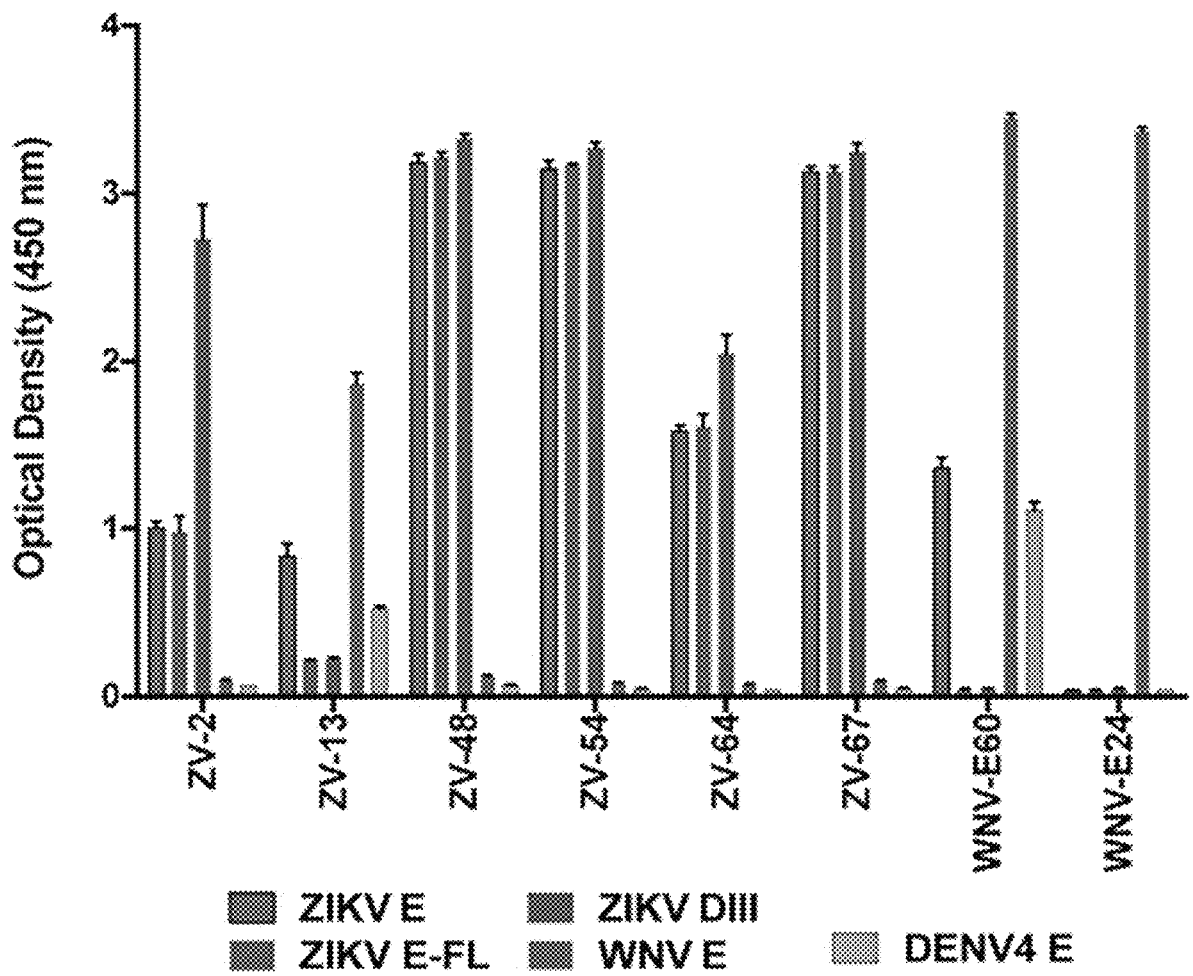

The mAbs were tested for their specificity by evaluating reactivity with cells infected by ZIKV, DENV (all four serotypes), or JEV. Five of the mAbs (ZV-2, ZV-48, ZV-54, ZV-64, and ZV-67) were ZIKV-specific and did not recognize DENV or JEV-infected cells by flow cytometry (FIG. 1A, and data not shown); these mAbs all bound to recombinant ZIKV DIII in a direct ELISA (FIG. 1B). In contrast, one mAb (ZV-13) showed cross-reactivity and bound to cells infected with all serotypes of DENV (FIG. 1A). Consistent with this data, only ZV-13 bound to WNV E protein in an ELISA (FIG. 1B). ZV-13 recognized the highly conserved fusion loop in DII, as binding was lost to a ZIKV E protein with mutations in highly conserved residues within and immediately proximal to the fusion loop (FIG. 1B).

Example 2. Neutralizing Activity Against ZIKV In Vitro

Figure 1C:
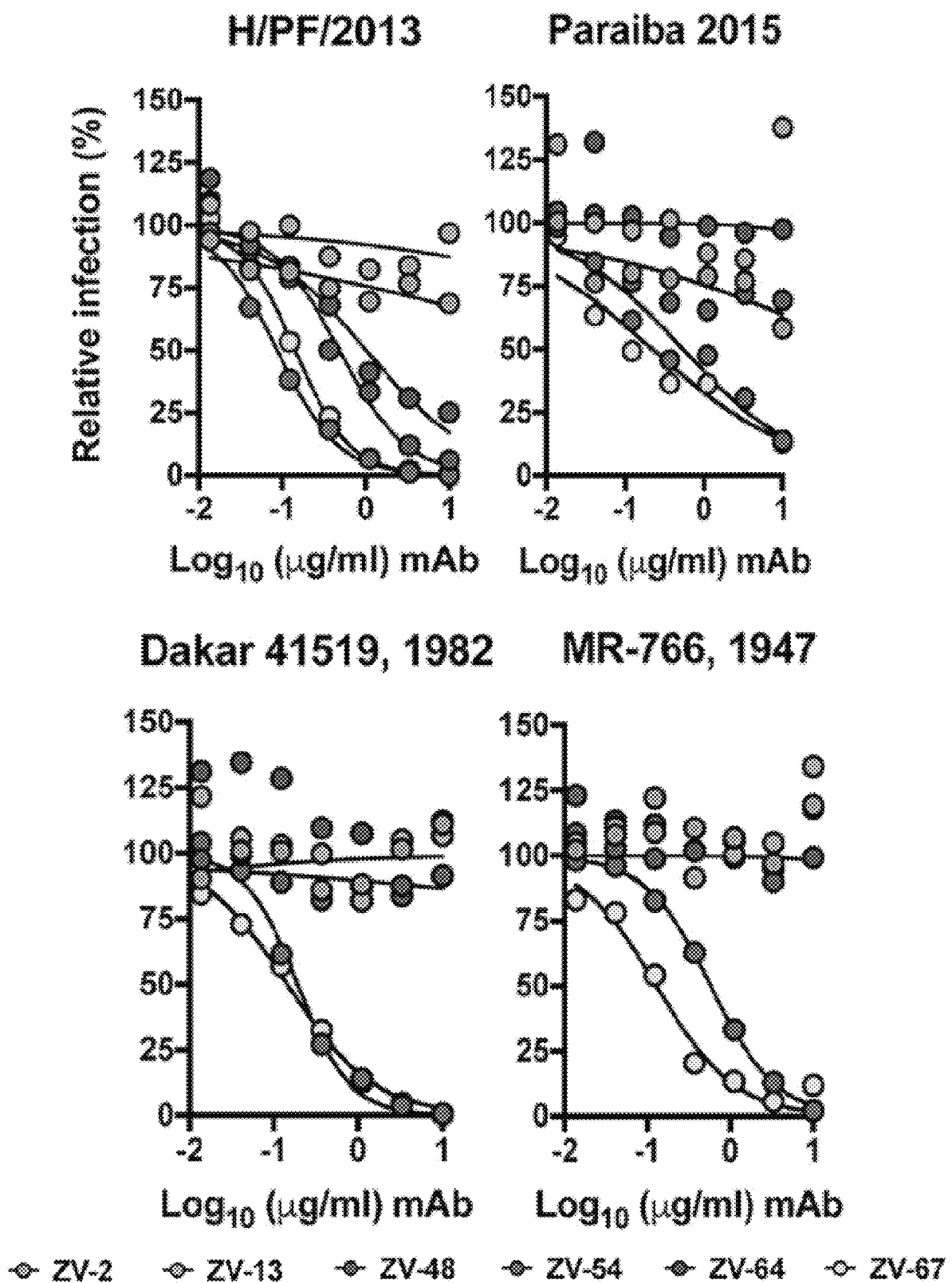

The mAbs were evaluated for their ability to inhibit ZIKV H/PF/2013 infection in Vero cells using a focus reduction neutralization test (FRNT) (Brien et al., 2013). Four (ZV-48, ZV-54, ZV-64, and ZV-67) of the six mAbs had neutralizing activity whereas two (ZV-2 and ZV-13) did not inhibit infection appreciably (FIG. 1C). To determine the breadth of their activity, the mAbs were evaluated for inhibition of infection by three other ZIKV isolates including two African (MR-766, Uganda 1947 and Dakar 41519, Senegal 1982) and an American (Paraiba 2015, Brazil) strain. Whereas ZV-54 and ZV-67 neutralized all four ZIKV strains, ZV-48 and ZV-64 showed reduced inhibitory activity against the other tested strains (FIG. 1C).

Example 3. Binding Characteristics of Anti-ZIKV mAbs

Figure 2A:
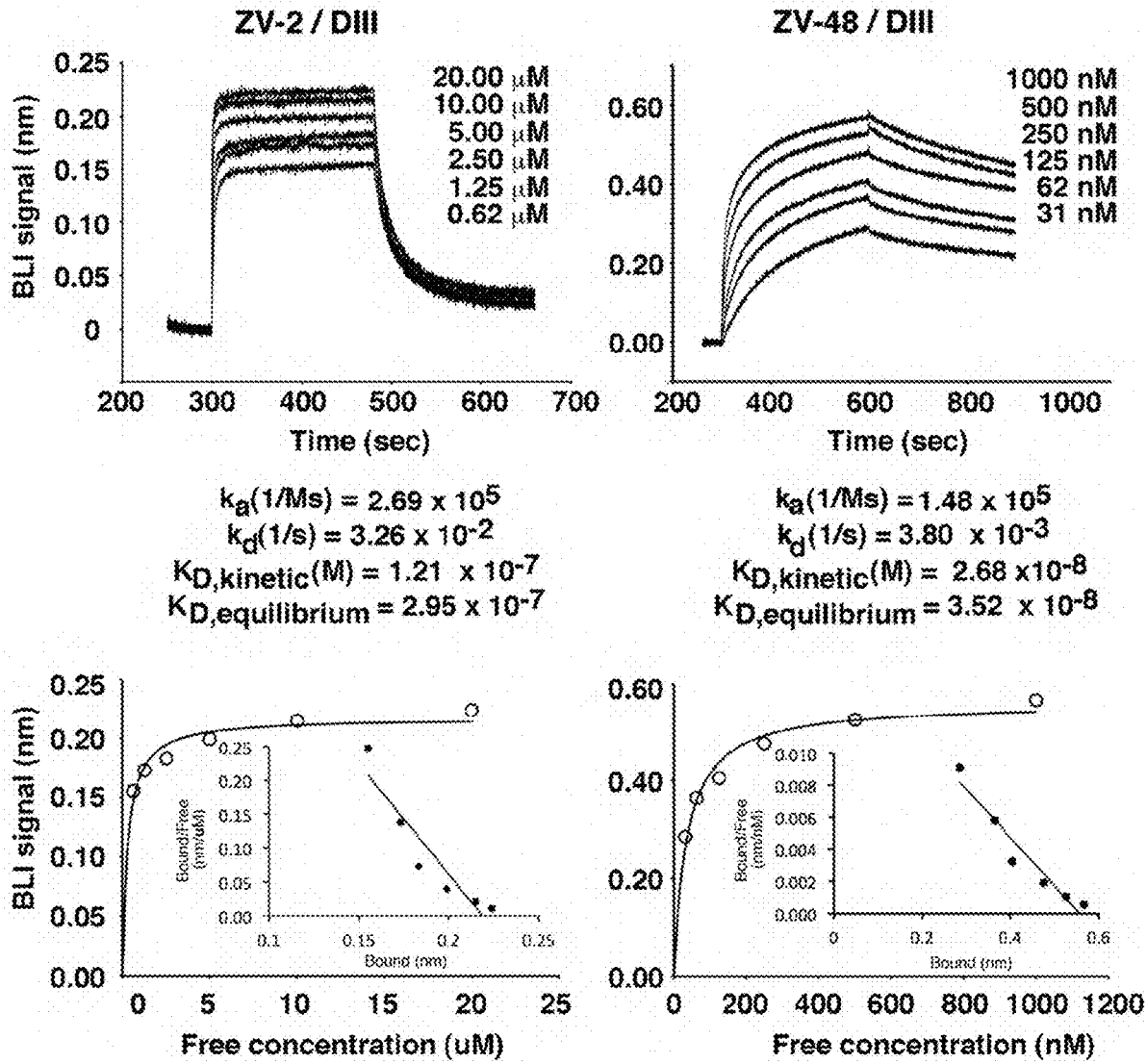
Figure 7:
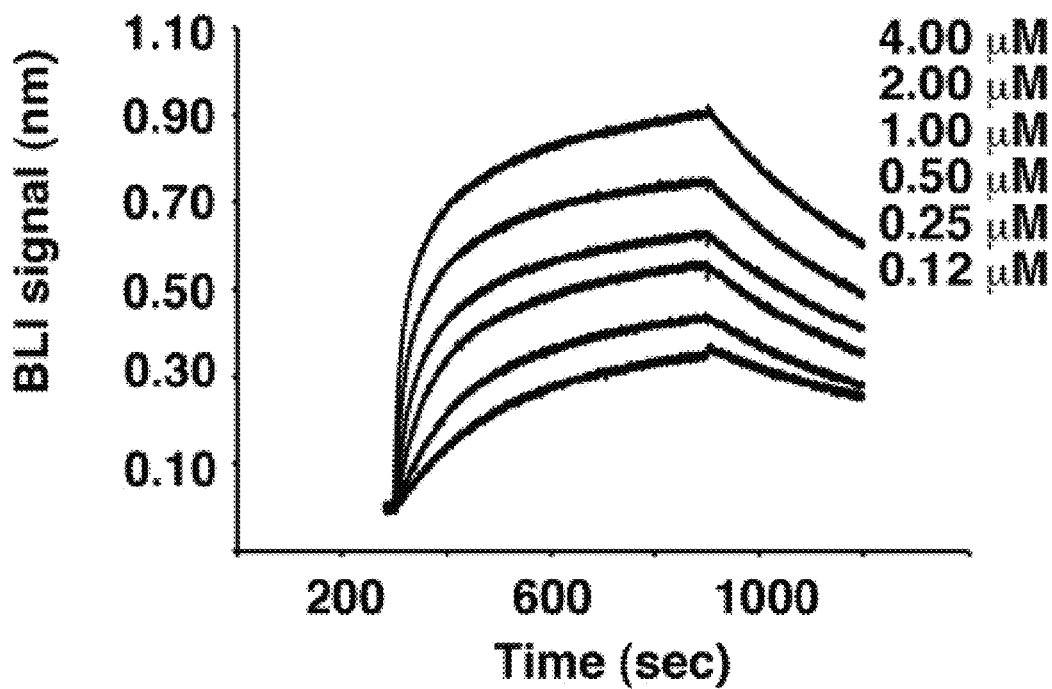
FIG. 7 depicts graphs showing supplemental BLI binding data, related to FIG. 2. ZV-13 mAb binding to recombinant soluble ZIKV E protein as assayed by BLI. Randomly biotinylated ZV-13 mAb was coated onto Streptavidin biosensor pins. The pins were equilibrated in binding buffer alone (HBS-EP+1% BSA) before being plunged into wells containing various concentrations of recombinant ZIKV E ectodomain protein. The association lasted ten minutes before the pins were placed back in binding buffer to allow for dissociation. The real-time data were analyzed using Biaevaluation 4.1 (GE Healthcare). Association and dissociation profiles, as well as steady-state equilibrium concentration curves, were fitted assuming a 1:1 binding model.
Figure 7:
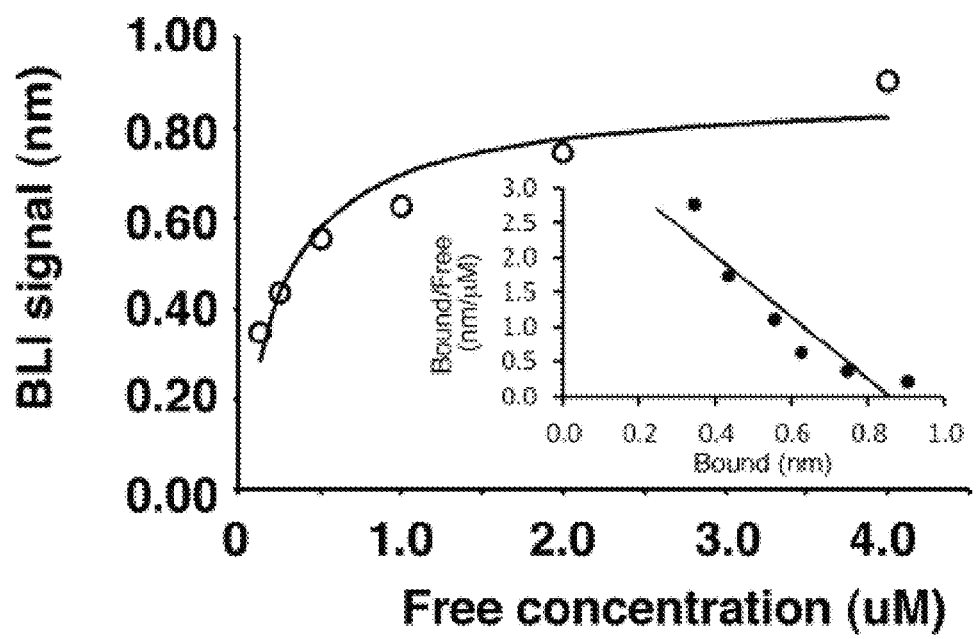
Figure 8A:
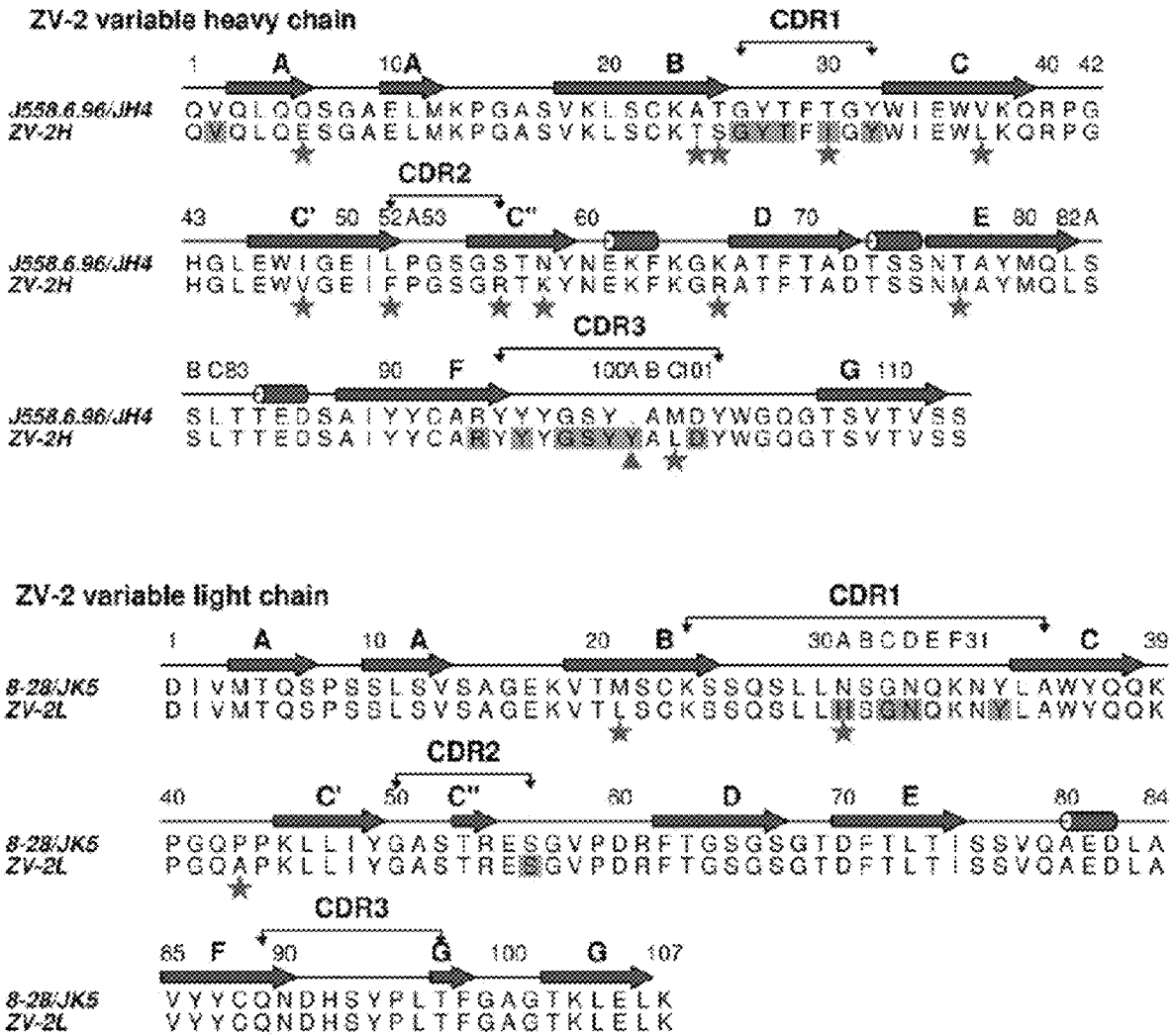
FIG. 8A, FIG. 8B and FIG. 8C depict MAb sequence alignments and antigen contacts, related to FIG. 3 and FIG. 4. Structure-based alignment of the ZV-2 germ line sequence with the variable heavy chain and light chain sequences (FIG. 8A), the ZV-48 and ZV-64 germ line sequence with the variable heavy chain and light chain sequences (FIG. 8B), and the ZV-54 and ZV-67 germ line sequence with the variable heavy chain and light chain sequences (FIG. 8C) of the anti-ZIKV mAbs, with the DIII-contacting amino acids boxed in the color of the epitope they bind: green for the ABDE epitope, cyan for the C-C' epitope, and magenta the for lateral ridge epitope. The numbering is given above the aligned sequences, with insertions as described (Al-Lazikani et al., 1997). Complementarity determining regions (CDR 1-3) are marked at the top of the alignment. The secondary structure elements are indicated in blue (arrows for β-sheet and coil for α-helices).
Figure 8B:
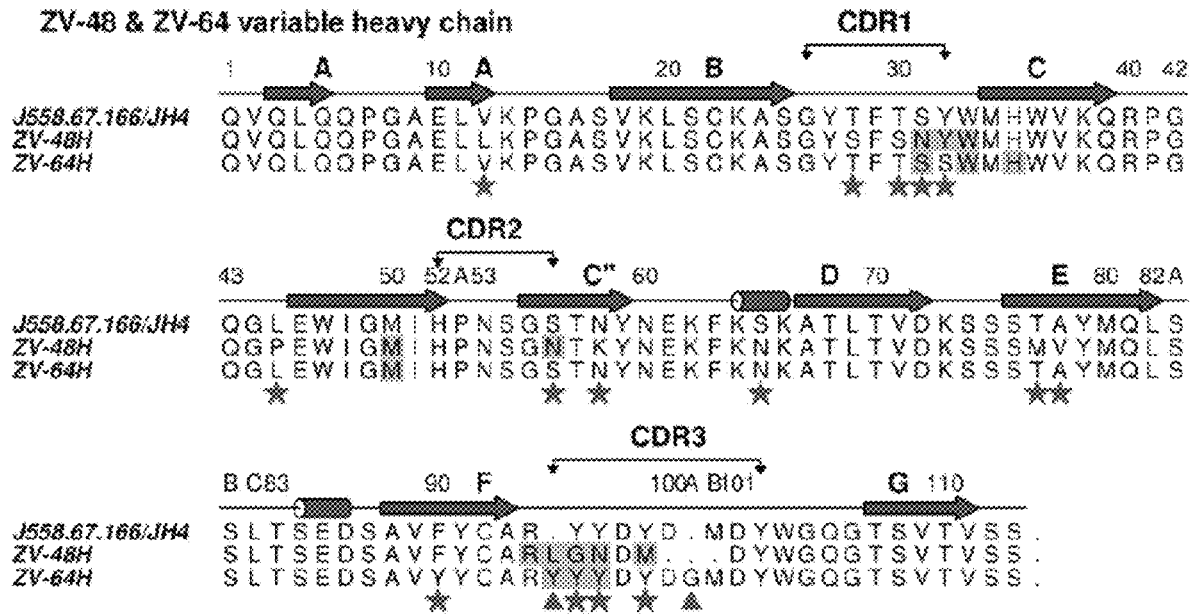
Figure 8B:
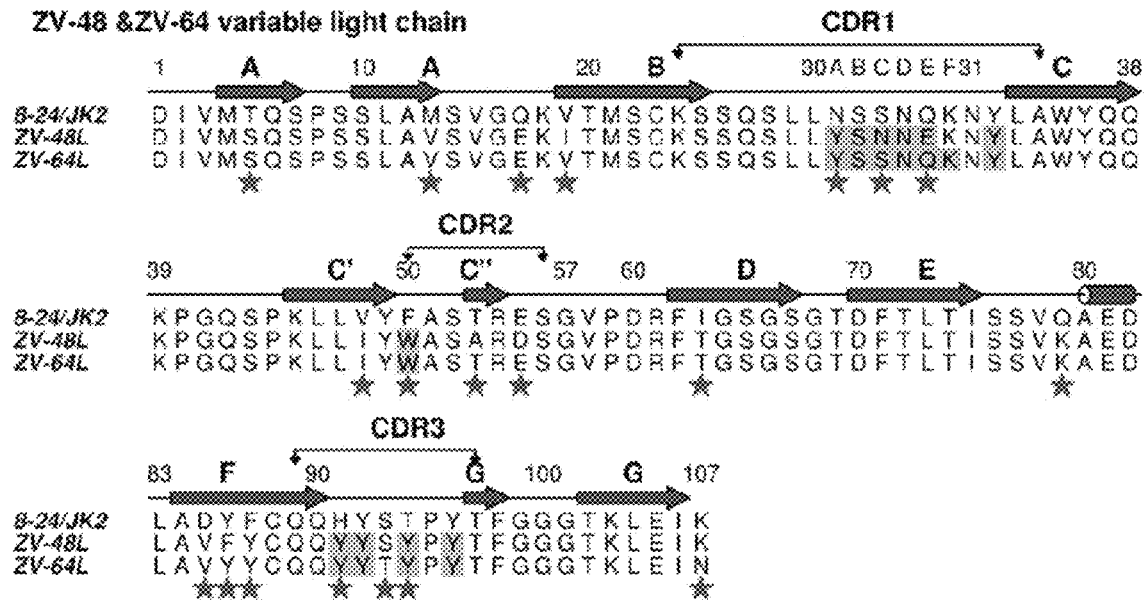
Figure 8C:
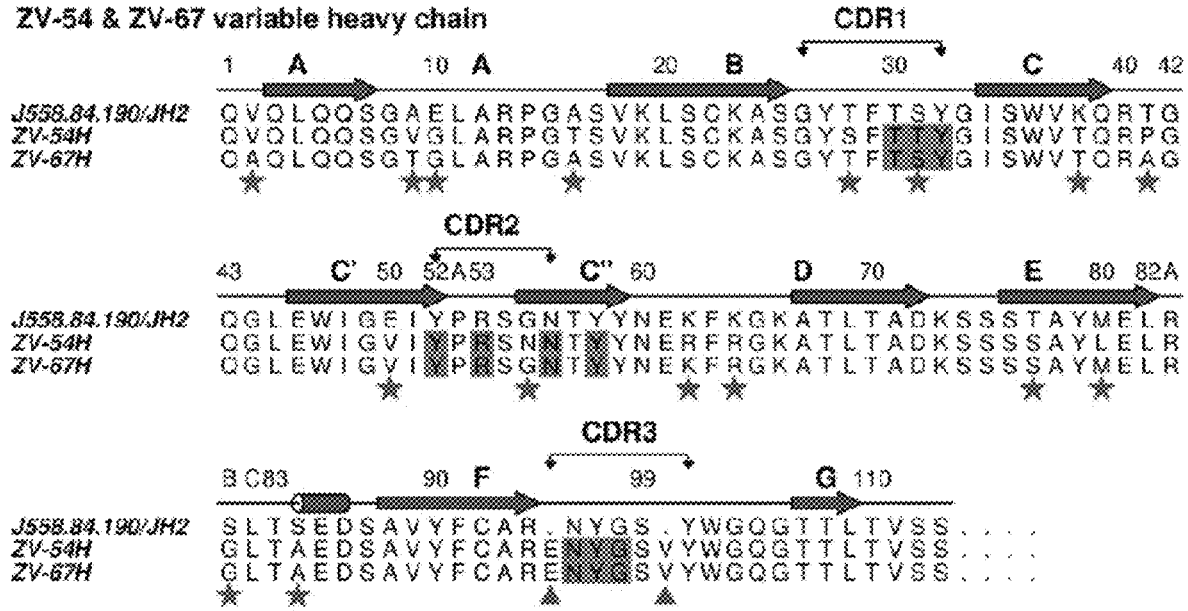
Figure 8C:
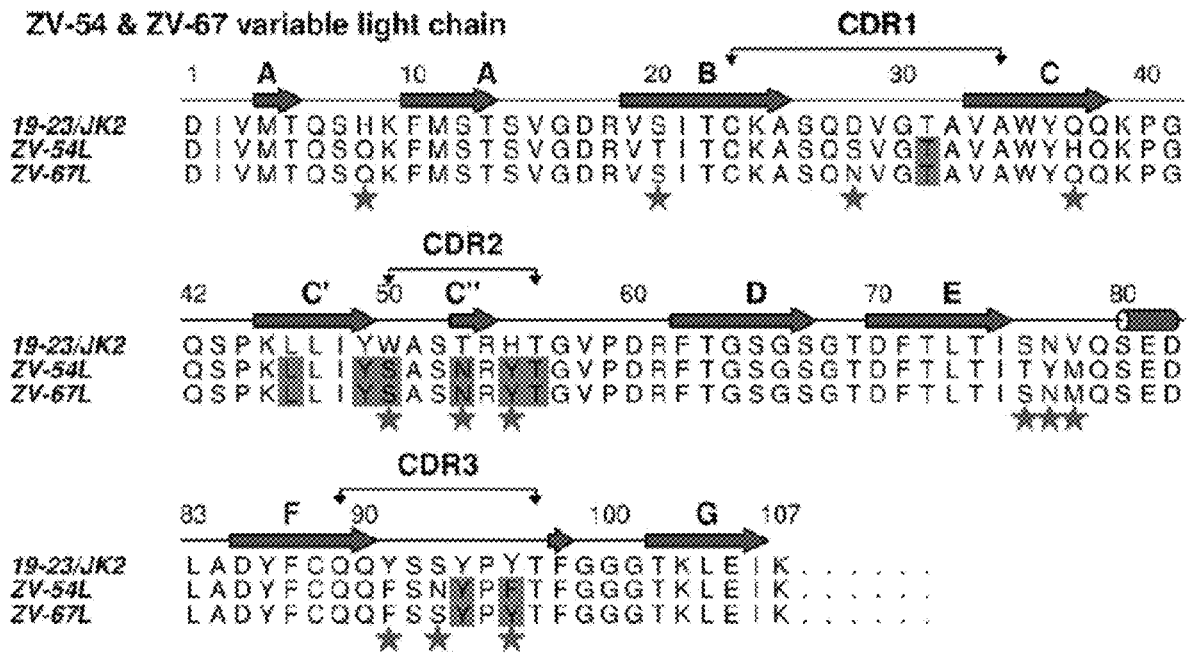

It was next assessed whether the variation in neutralizing activity among the antibodies could be explained by differences in relative binding to the ZIKV E protein derived from H/PF/2013. Based on the ELISA data, the mAbs were tested for binding to a recombinant DIII produced in *E. coli* using biolayer interferometry (BLI) (FIG. 2A and Table 1) or, for the fusion-loop epitope binding ZV-13, the monomeric form of the ectodomain of E expressed in mammalian cells (FIG. 7 and Table 1). These biophysical analyses showed that mAbs with stronger neutralizing capacity had greater binding affinities for recombinant proteins. For example, the best neutralizing antibodies, ZV-54 and ZV-67, had the highest affinities with KD equilibrium values less than 10 nM. These two mAbs also showed the slowest dissociation rates, with half-lives of 33 and 13.8 minutes, respectively. The mAbs with intermediate neutralizing capacity, ZV-64 and ZV-48, had lower affinities, with KD equilibrium values around 35 nM, and more rapid off-rates, having half-lives of 1 and 3.2 minutes, respectively. ZV-2 and ZV-13, which do not inhibit infection appreciably, showed weaker binding, with KD equilibrium values greater than 250 nM.

Figure 2B:
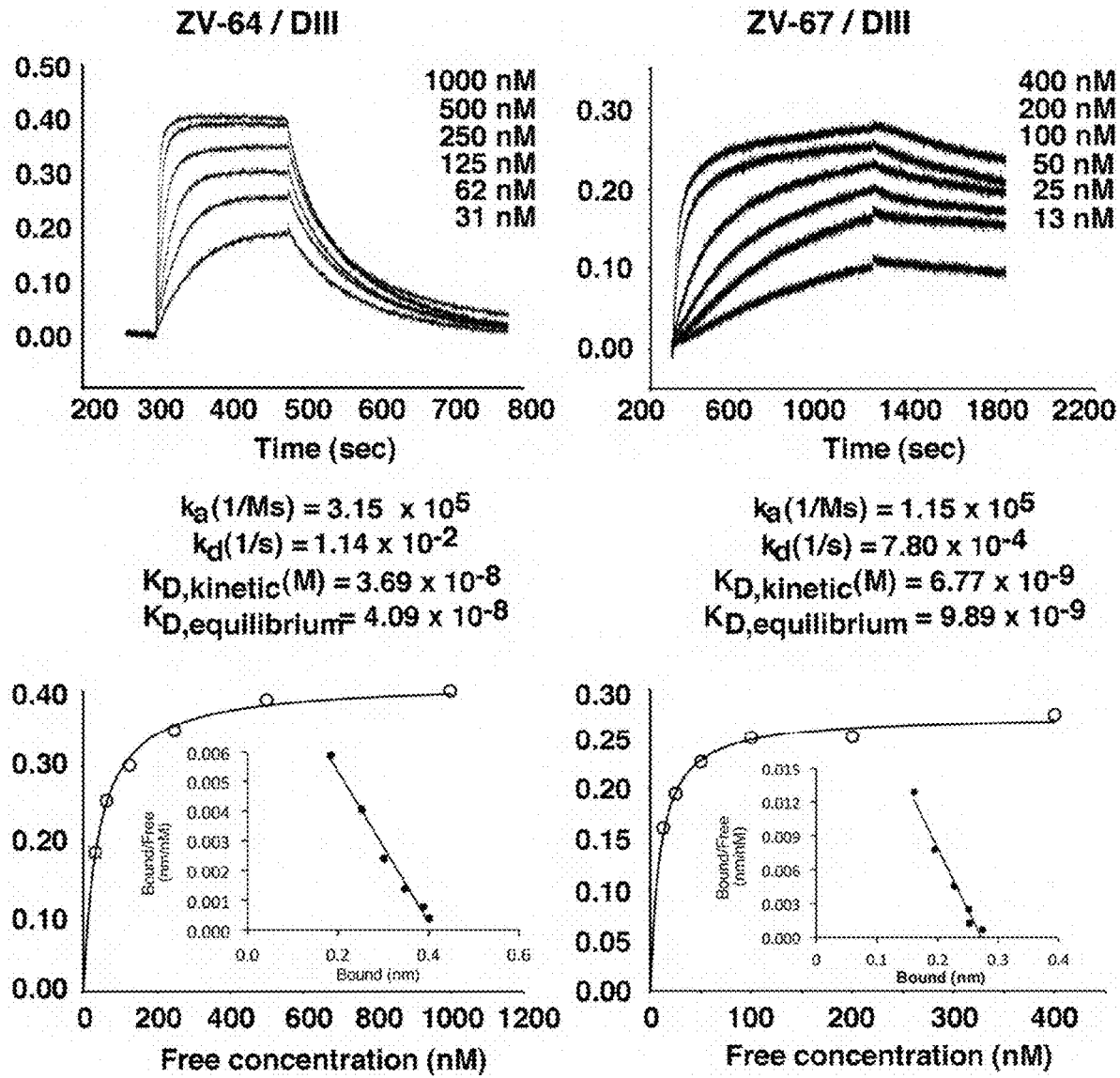

Based on the interactions of individual mAbs with purified ZIKV proteins, it was speculated that differences in the stoichiometry of binding to the viral particle, which also is a function of epitope accessibility (Pierson and Diamond, 2015; Pierson et al., 2007), also might correlate with the neutralization data. To test this idea, purified ZIKV subviral particles (SVPs, prM-E) were captured on 96 well plates and binding of biotinylated detection mAbs (ZV-2, ZV-13, ZV-48, ZV-54, ZV-64, and ZV-67) were analyzed over a range of concentrations. Notably, there was an association between the functional avidity of binding and the ability to neutralize infection: ZV-67 and ZV-54 bound most avidly whereas ZV-2 and ZV-13 bound more weakly (FIG. 2B). This data also showed that even at the highest concentrations tested (i.e., 10 µg/ml) ZV-2 and ZV-13 failed to saturate binding to the SVPs.

Figure 2C:
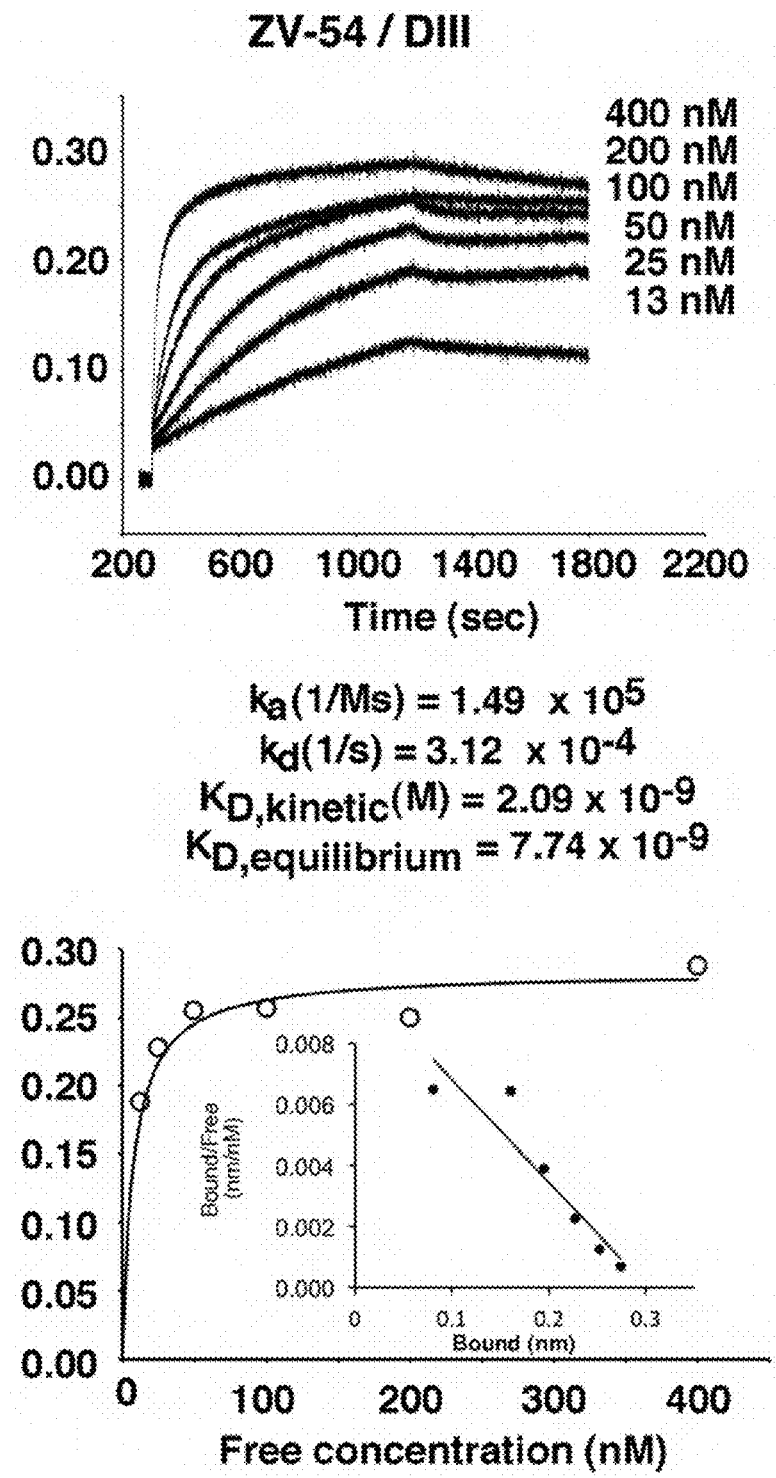
Figure 2D:
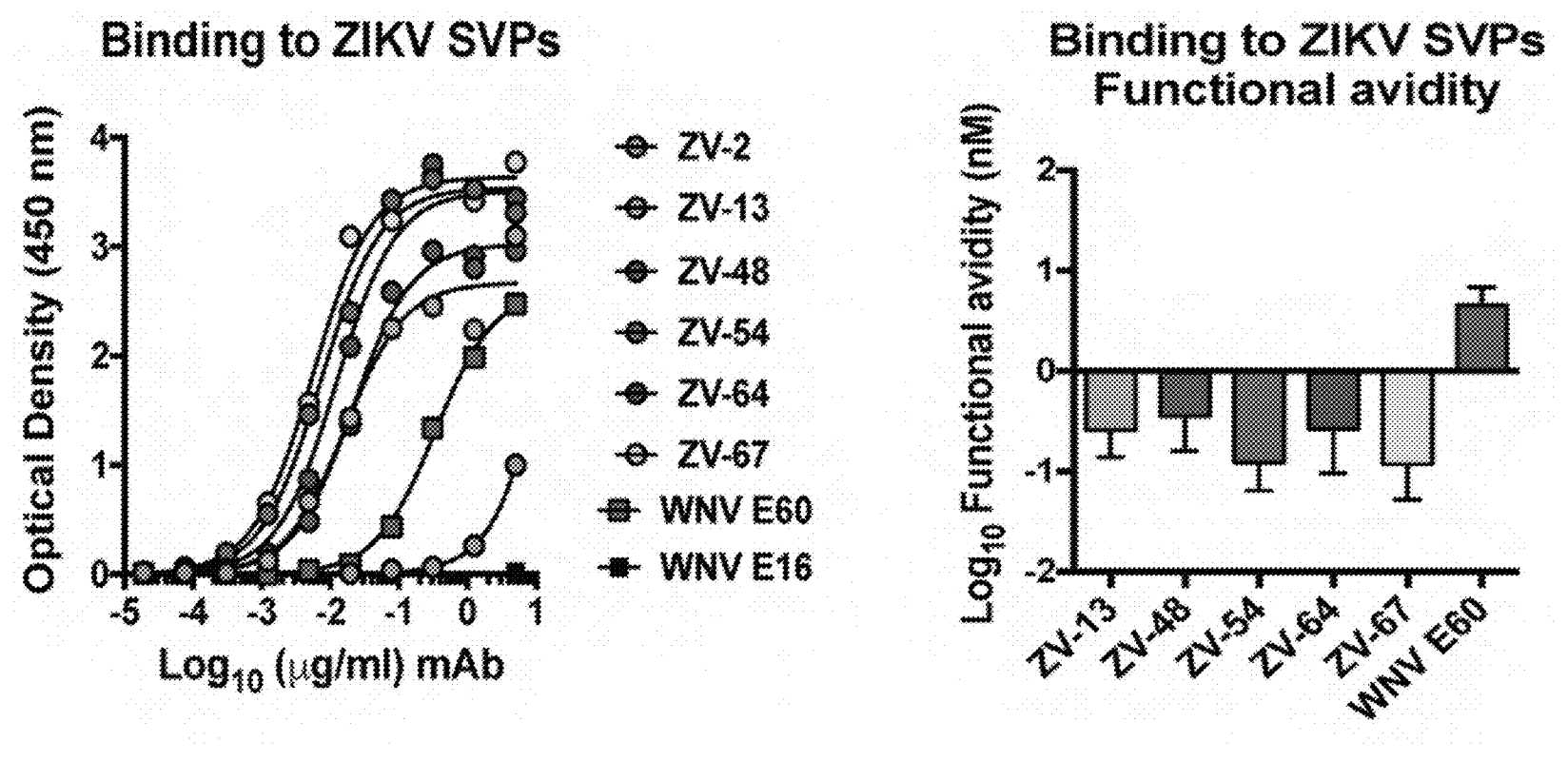
Figure 2E:
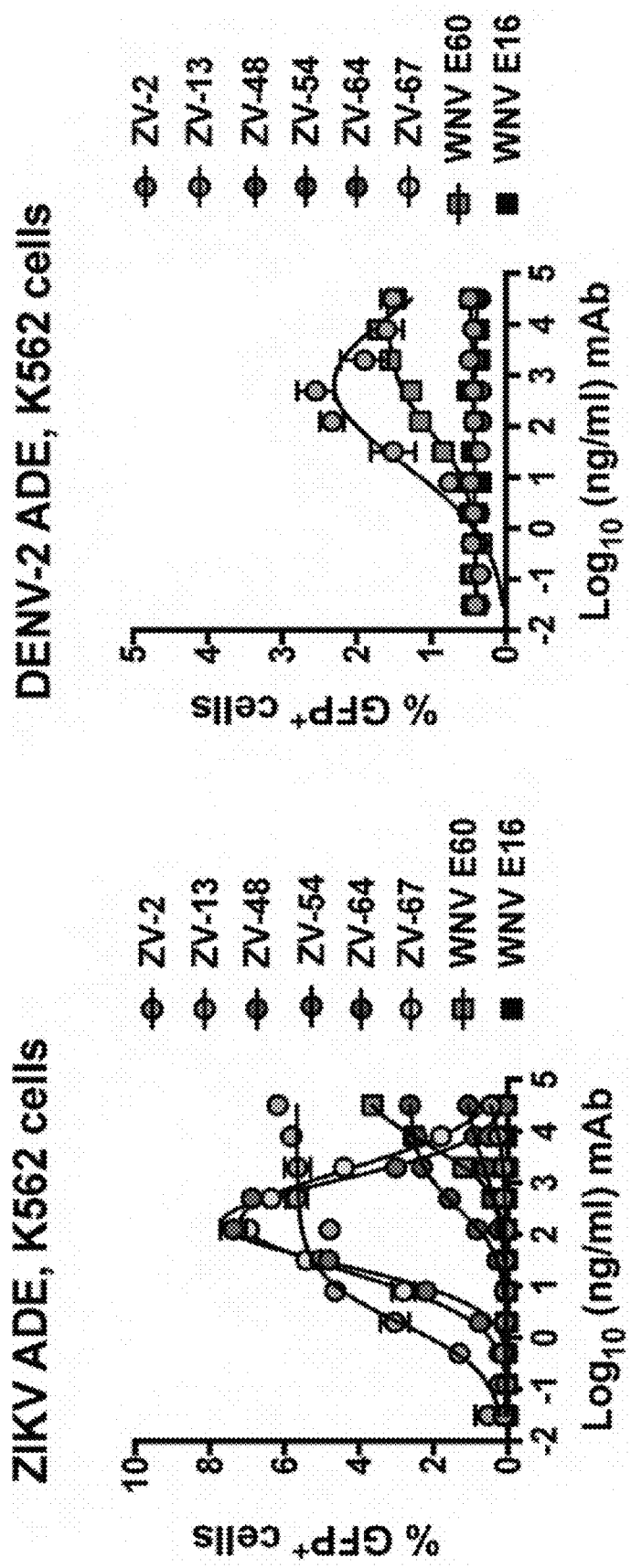

As these binding studies were performed with SVPs, these results were confirmed with pseudo-infectious reporter virus particles (RVPs) in a functional assay. Antibody-mediated neutralization requires engagement of the virions by antibody with a stoichiometry sufficient for neutralization. Antibody-dependent enhancement of infection (ADE) occurs following engagement of the virion by fewer antibody molecules (Pierson and Diamond, 2015), and thus represents a sensitive functional probe for antibody binding to an infectious virion. The antibody concentration dependence and magnitude of ADE of ZIKV and DENV by the anti-ZIKV mAbs was evaluated using an established assay (Pierson et al., 2007) in Fc1 receptor II (Fc1RII, CD32A) expressing human K562 cells. While all ZIKV mAbs enhanced infection to varying degrees, those which bound SVPs weakly (e.g., ZV-2) also minimally supported Fc1RII-mediated infection (FIG. 2C). Reciprocally, as described previously for WNV antibodies (Pierson et al., 2007), the most inhibitory anti-ZIKV mAbs (e.g., ZV-54 and ZV-67) exhibited ADE but this occurred only at sub-neutralizing concentrations. These experiments also corroborated the type-specificity of the mAbs, as only ZV-13 supported ADE of DENV; this latter observation suggests that at least some ZIKV-specific antibodies generated during natural infection are capable of enhancing DENV infection in vitro.

Example 4. Structures of ZIKV Antibodies in Complex with DIII

Figure 3A:
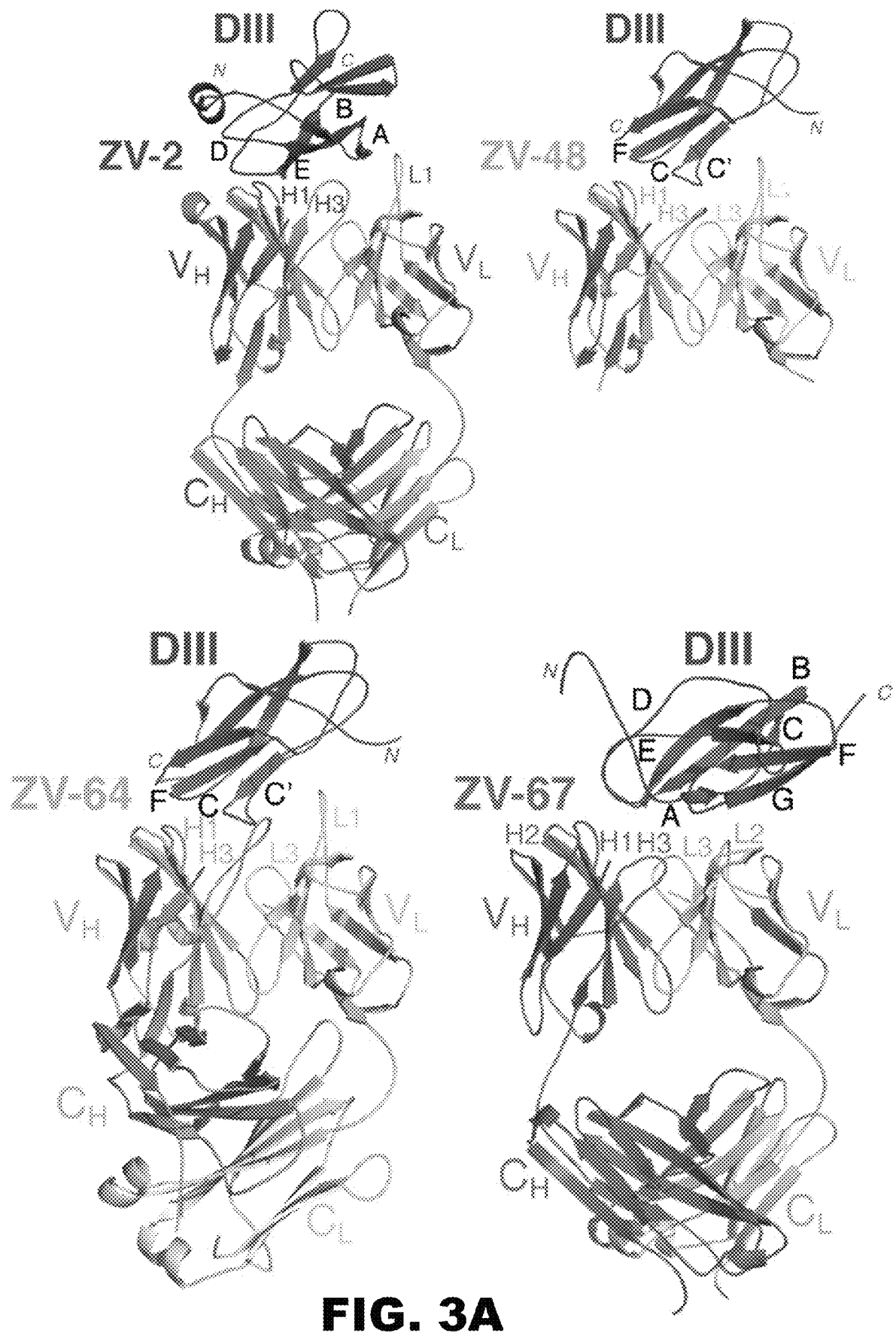
FIG. 3A, FIG. 3B and FIG. 3C depict structures of anti-ZIKV Fabs and scFv complexed with DIII.

To gain insight into the basis for differential binding and neutralization of the ZIKV mAbs, Fab fragments or scFvs were generated and crystal screening using DIII of ZIKV H/PF/2013 was performed. High-resolution X-ray crystal structures were obtained for four antibody complexes with DIII: ZV-2 Fab to 1.7 Å resolution, ZV-48 scFv to 1.7 Å resolution, ZV-64 Fab to 1.4 Å resolution, and ZV-67 Fab to 1.4 Å resolution (FIG. 3A, data collection and refinement statistics in Table 2, antibody-antigen structural analysis in Table 3, Table 4, and Table 5). In all four complexes, ZIKV DIII adopts a highly conserved structure nearly identical to that observed in soluble E dimers (Dai et al., 2016) as well as mature virions (Kostyuchenko et al., 2016; Sirohi et al., 2016) with significant variation observed only at the N and C-terminal regions of the domain. Analysis of antibody contact residues indicates that ZV-2 and ZV-67 binding is dominated by heavy chain complementarity determining region (CDR) usage whereas ZV-48 and ZV-64, which both engage DIII in a similar manner, primarily use light chain CDRs (Table 3, Table 4, and Table 5, and FIG. 8). Notably, 10 of 12 light chain CDR contact residues are identical in ZV-48 and ZV-64 whereas only 2 of 11 heavy chain CDR residues are the same, with the most significant difference in the short CDR-H3 of ZV-48 that makes more contact with DIII than the long CDR-H3 found in ZV-64 (FIG. 1B and FIG. 8). Comparison of the sequences of ZV-67 with ZV-54, the latter of which lacks structural data, suggests that they bind DIII in a highly analogous manner, as only two contact residues differ, CDR-L3 Tyr/Phe$^{L96}$ and CDR-H1 Ser/Thr$^{H31}$.

Example 5. ZIKV mAbs Bind Three Spatially Distinct Epitopes on DIII

Figure 3B:
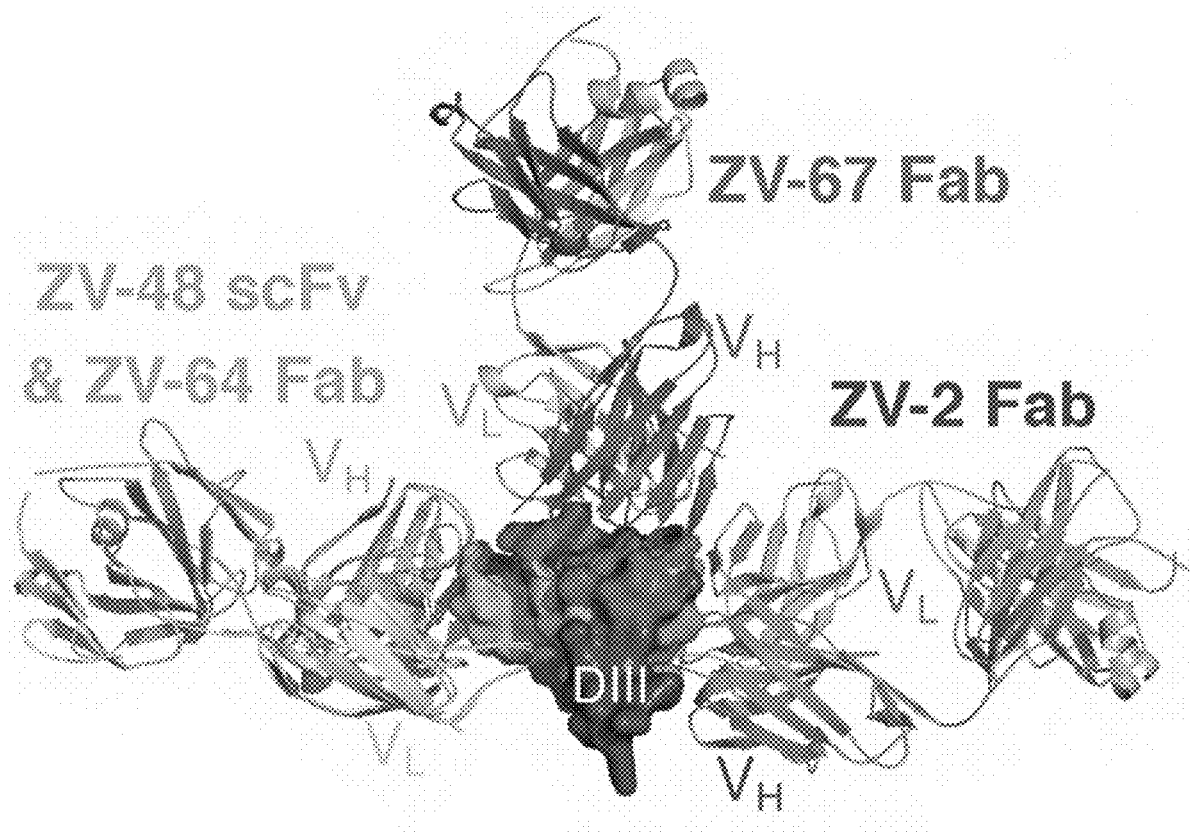
Figure 3C:
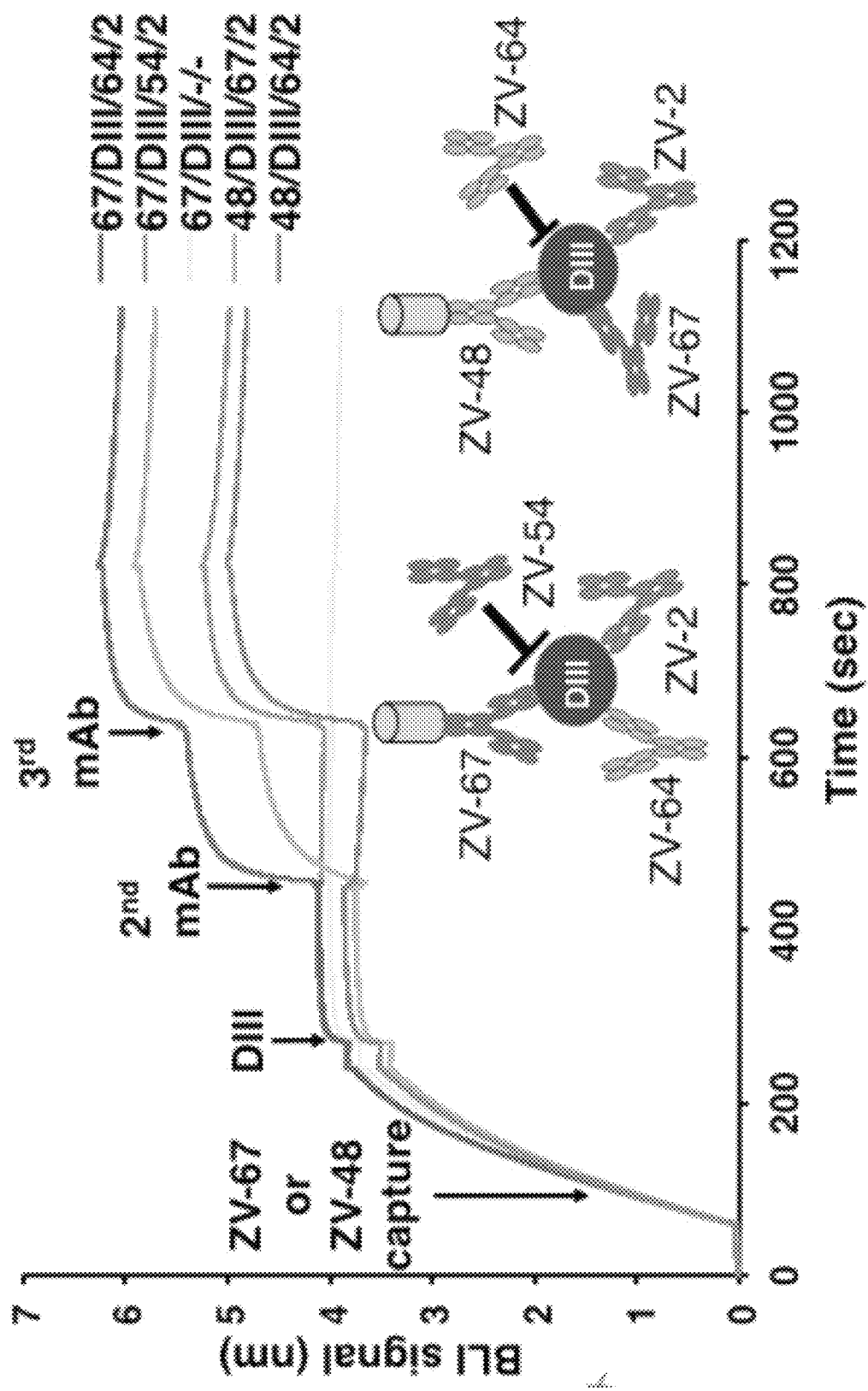

Analysis of the docking of the mAbs onto DIII indicates that ZV-2 and ZV-67 binding should not compete with ZV-48 or ZV-64 binding, whereas ZV-48 and ZV-64 should compete with each other (FIG. 3B). To evaluate this prediction experimentally a competitive BLI assay was conducted (FIG. 3C). When ZV-67 was immobilized, it was observed that both ZV-64 and ZV-2 could bind in a DIII-dependent manner. In contrast, ZV-54 binding was excluded supporting the idea that ZV-67 and ZV-54 recognize that same DIII determinants. Analogously, immobilized ZV-48 allowed for the binding of ZV-67 and ZV-2 after DIII capture, but ZV-64 was blocked competitively. This analysis strongly supports the structural observations and defines three distinct ZIKV type-specific epitopes on DIII.

Example 6. ZIKV DIII Epitope Mapping

Figure 4A:
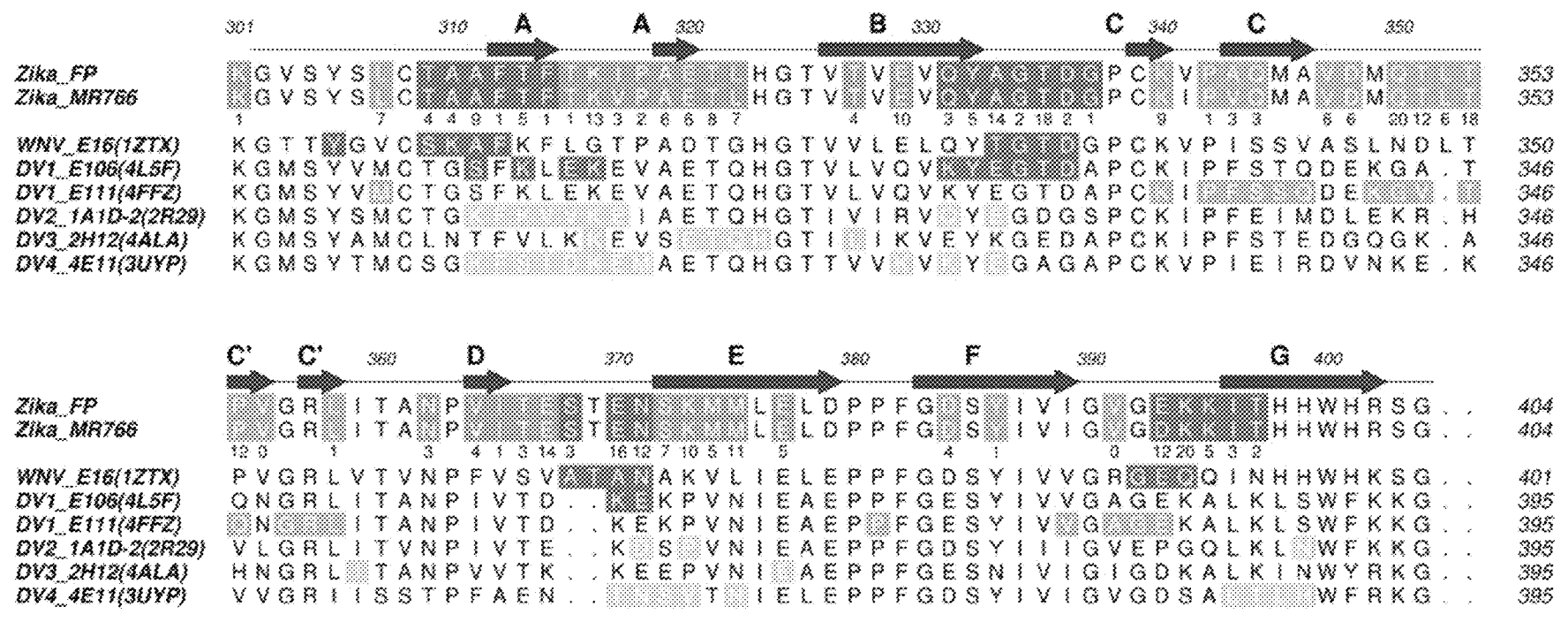
Figure 4B:
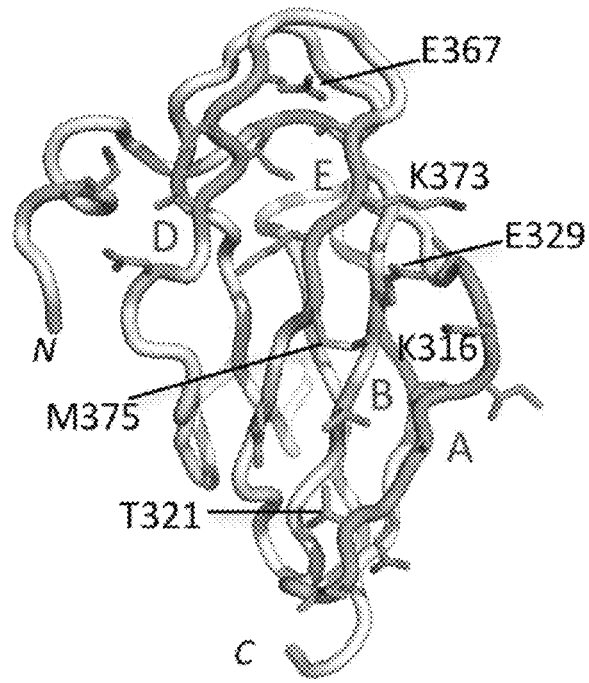
Figure 4B:
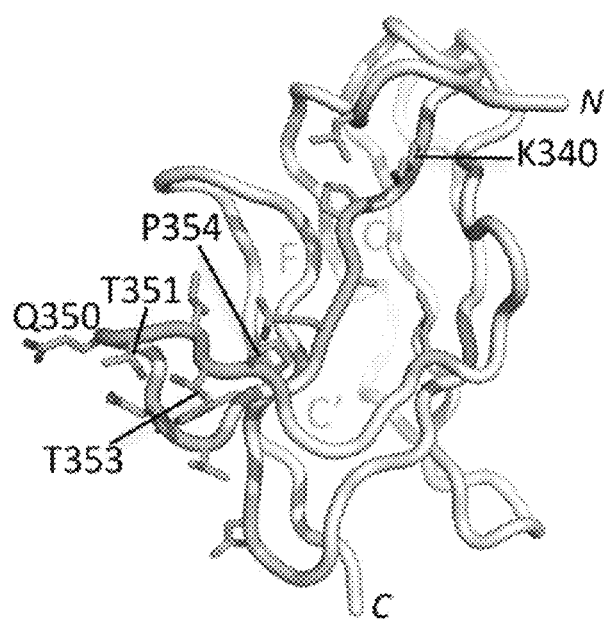
Figure 4B:
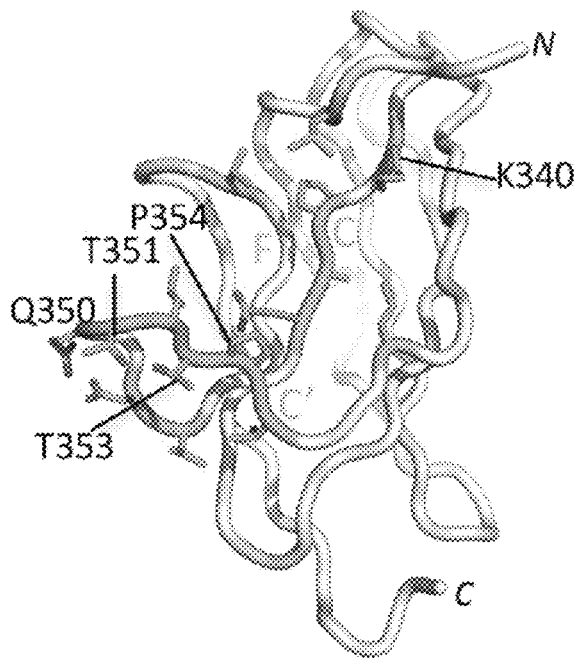
Figure 4B:
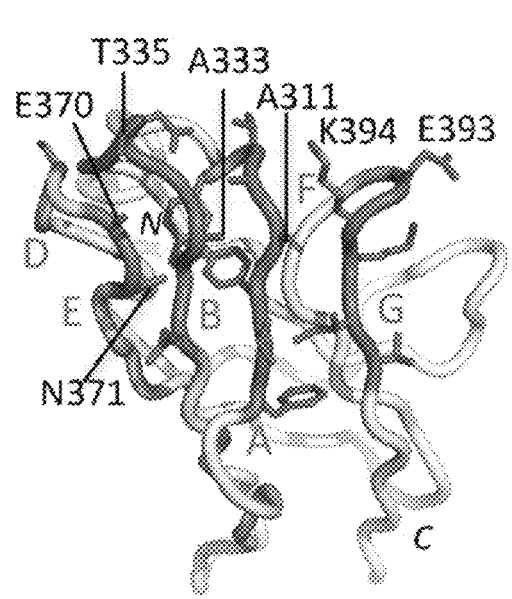

The precise footprints of the mAbs on ZIKV DIII were next examined (FIG. 4A and FIG. 4B). ZV-2 binds to a large, fairly flat surface created by 21 van der Waal contact residues on the exposed face of the ABDE β-sheet of DIII (Table 3). The ABDE sheet epitope is highly conserved among ZIKV sequences but many of the primary contacts diverge in DENV and other flaviviruses. Previous structural studies of the DENV cross-reactive mAb 2H12 revealed that it contacts six of the same residue positions, especially near the A-B loop, with 4 residues conserved in DENV-3 (Midgley et al., 2012). ZV-48 and ZV-64 both primarily engage the C- and C'-β-strands and connecting loop, which project away from the β-sandwich core of DIII. Each of these two antibodies contact a total of 15 residues, with ZV-64 uniquely contacting Val$^{E55}$ and Val$^{E391}$ and ZV-48 uniquely interacting with Asp$^{E384}$ and Val$^{E386}$ using CDR-H1 Asn$^{E131}$ and CDR-H2 Asn$^{H56}$, both of which are Ser residues in ZV-64 that makes no analogous contacts. The C-C' loop epitope recognized by ZV-48 and ZV-64 is remarkably similar to that engaged by the DENV-1 type specific antibody E111 (Austin et al., 2012), with 9 structurally related positions contacted (4 conserved) (FIG. 4A).

The epitope recognized by ZV-67 is created by four discrete secondary structure elements of ZIKV DIII; the A-strand, B-C loop, D-E loop, and F-G loop. A total of 21 residues are contacted by ZV-67, with only one difference between the two ZIKV immunizing strains (E$^{E393}$ in H/PF/2013, D$^{E393}$ in MR-766). This epitope region has been termed the LR, and was described in relation to the binding of the potently neutralizing E16 mAb against WNV DIII (Nybakken et al., 2005). A total of 13 of 16 WNV DIII residue positions contacted by E16 also are contacted by ZV-67, and 7 of these positions share the same sequence on H/PF/2013 DIII (FIG. 4A). DV1-E106 is another mAb recognizing the LR-epitope that has been characterized structurally in complex with DENV1 DIII (Edeling et al., 2014); it shares 10 contact positions with ZV-67, four of which are conserved in the B-C loops of both WNV and ZIKV (Tyr$^{E332}$, Gly$^{E334}$, Thr$^{E335}$, and Asp$^{E336}$). Another related epitope (termed the A-strand) has been described structurally for two DENV complex-specific mAbs, 1A1D-2 (Lok et al., 2008) and 4E11 (Cockburn et al., 2012), both of which make significant contacts with the A-, B-, E-, and G-strands of DIII (FIG. 4A). 1A1D-2 bound to DENV-2 DIII shares 7 contact positions with ZV-67 (2 sequence conserved), whereas 4E11 bound to DENV-4 DIII shares 10 contact positions (3 conserved). Notably, these A-strand epitope binding mAbs do not make significant contact with the B-C or F-G loop residues engaged by LR-epitope mAbs. Collectively, the three distinct DIII epitopes recognized by our mAbs are composed of 59 residues, which represents nearly one half of the total surface area of the domain. Remarkably there was no overlap in the contact residues that constitute the ZIKV ABDE sheet, C-C' loop, and LR epitopes.

Example 7. Exposed and Cryptic ZIKV Epitopes

Figure 5A:
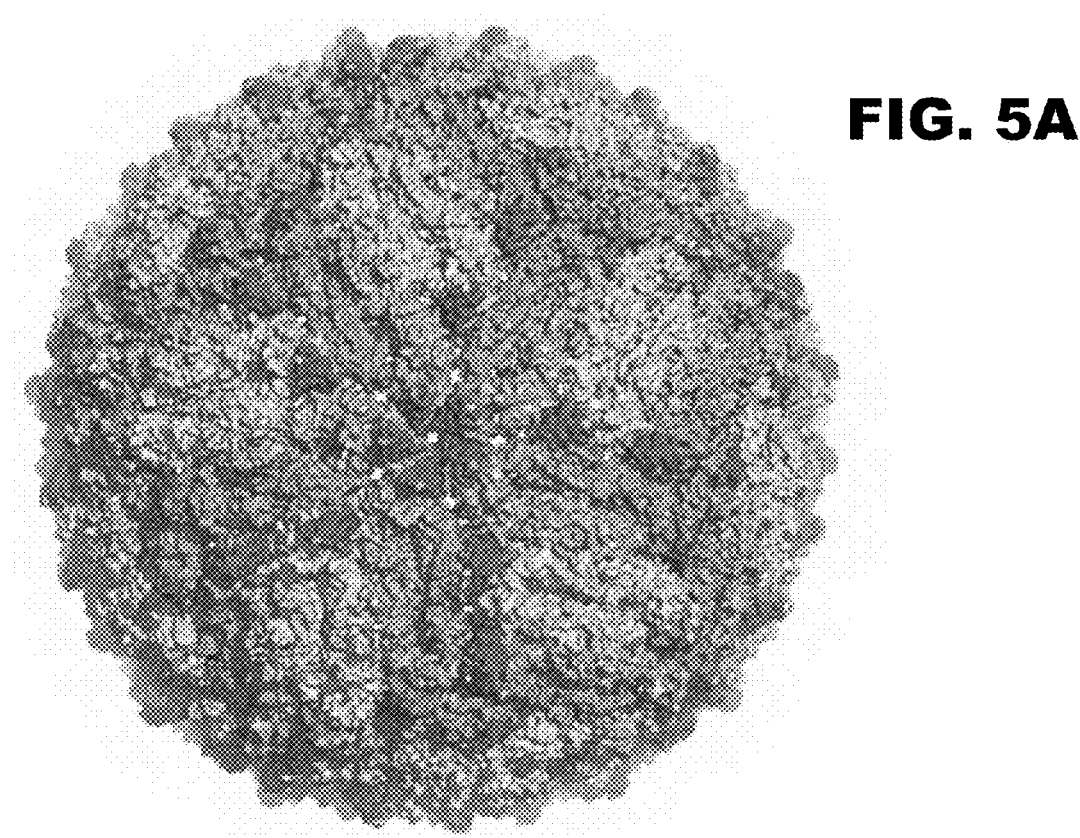
Figure 5B:
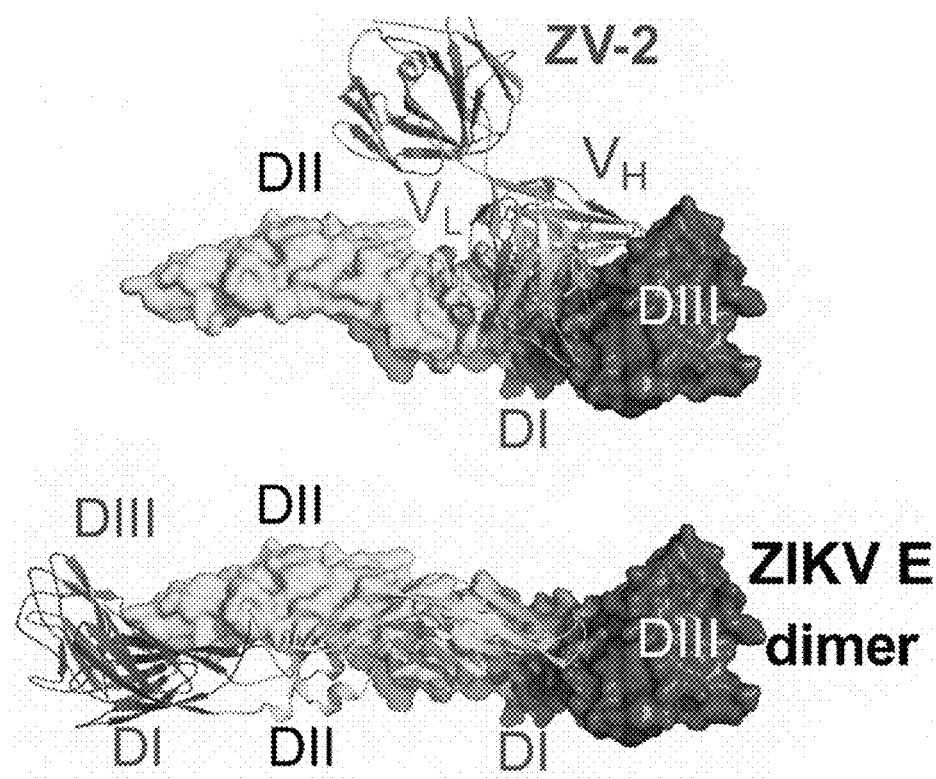
Figures 5C, 5D:
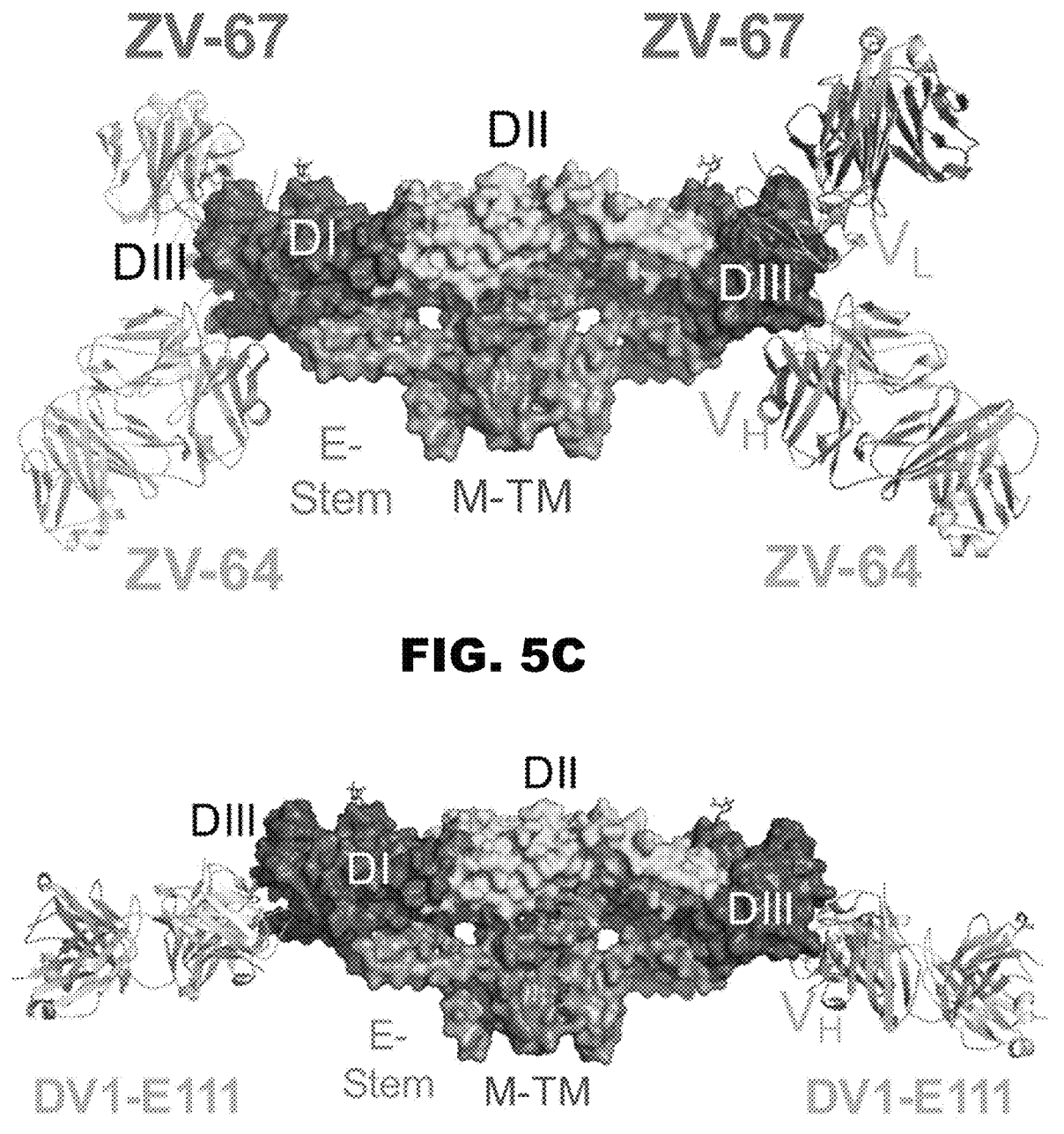
Figures 5E, 5F:
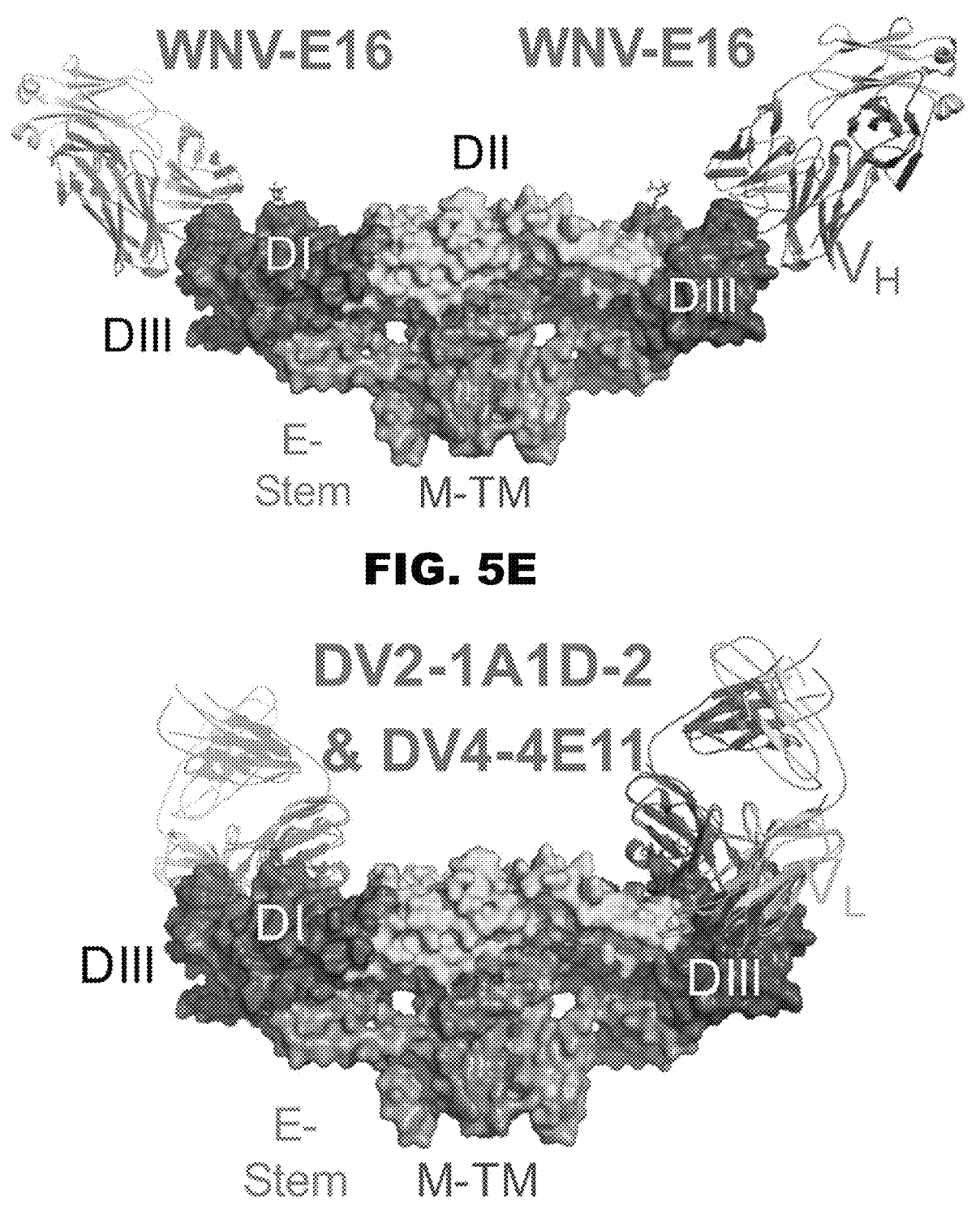

The mAb-DIII structures were docked onto the cryo-EM-derived model of the mature ZIKV virion (Kostyuchenko et al., 2016; Sirohi et al., 2016). With three envelope glycoproteins in the asymmetric unit, there are three potential binding environments for each of the mAbs. Whereas the LR epitope for ZV-67 was readily accessible on the mature virion (FIG. 5A), the C-C' loop and ABDE sheet epitopes were occluded almost completely in all three symmetry environments. We next examined the exposure of the ABDE sheet epitope on the E ectodomain crystal structure (Dai et al., 2016) and found that Fab binding is blocked sterically due to the positioning of DI (FIG. 5B). Furthermore, dimerization of E would preclude ZV-2 mAb binding as its CDR loops contact several of the same DIII residues that are contacted by the DII fusion loop residues in the dimer. Examination of the binding of ZV-64 reveals that it likely engages the cryptic C-C' loop epitope in a manner similar to the DENV-1 specific mAb DV1-E111 (Austin et al., 2012) (FIG. 5C and FIG. 5D). Residues on the C-C' loop are intimately involved in lateral E protein contacts on the mature virion, so their exposure would require substantial reorganization of the particle, which perhaps could occur locally rather than globally. The most potent mAbs, ZV-67 and ZV-54, recognize the LR epitope in manner similar to WNV-E16, which can bind up to 120 of the 180 copies of DIII on the mature virion (Kaufmann et al., 2006; Nybakken et al., 2005) (FIG. 5C and FIG. 5E). This is the same stoichiometry observed for the binding of the A-strand-specific mAb 1A1D-2 (Lok et al., 2008), which like 4E11 (Cockburn et al., 2012), can broadly neutralize multiple DENV serotypes (FIG. 5F). The clustering of DIII LR epitopes around the five-fold axis of symmetry appears to sterically preclude binding at this site (FIG. 5A), although minor repacking of the interface could lead to possible binding (Edeling et al., 2014).

Example 8. In Vivo Protection Studies

Figure 6B:
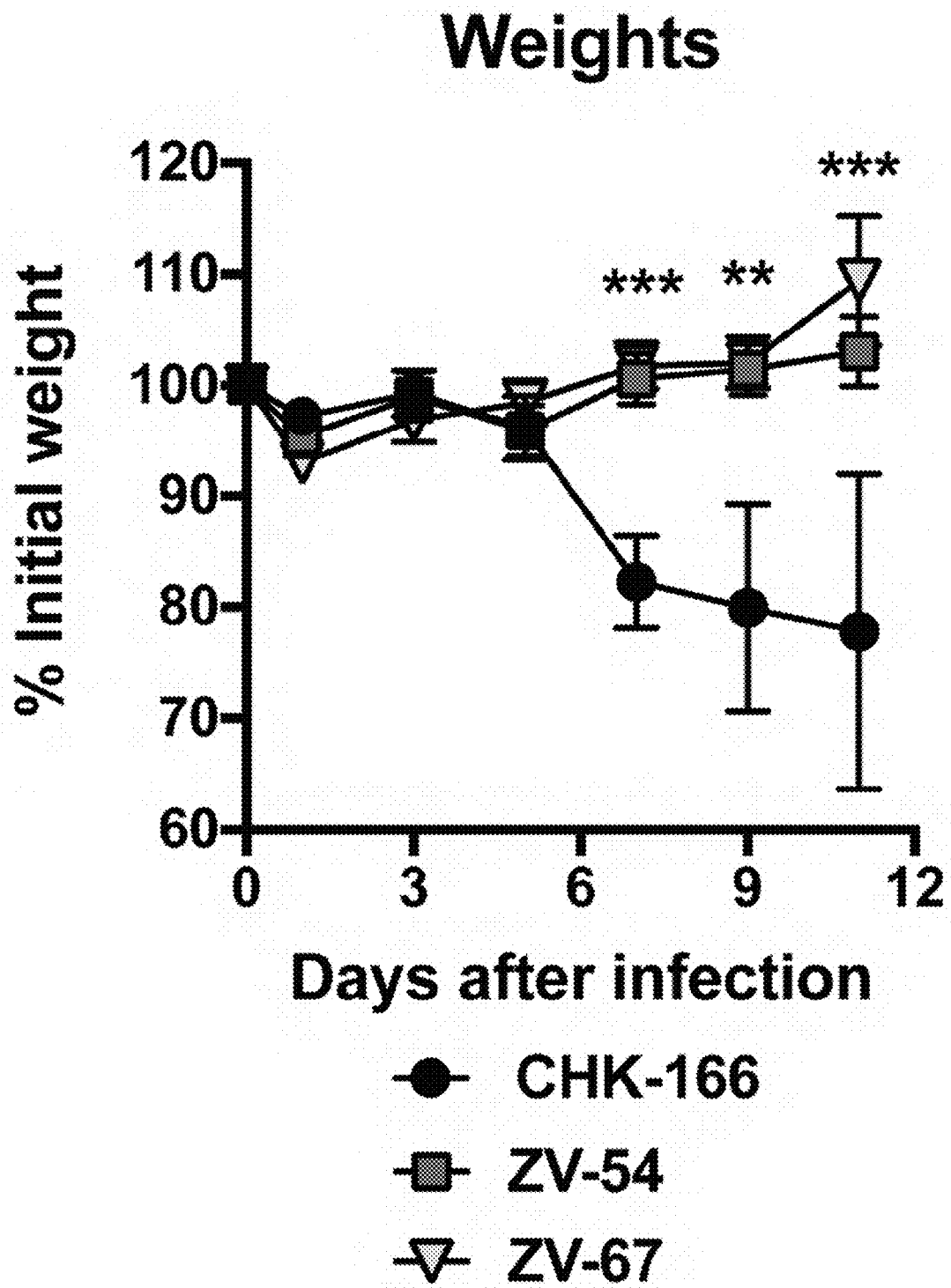
Figure 6C:
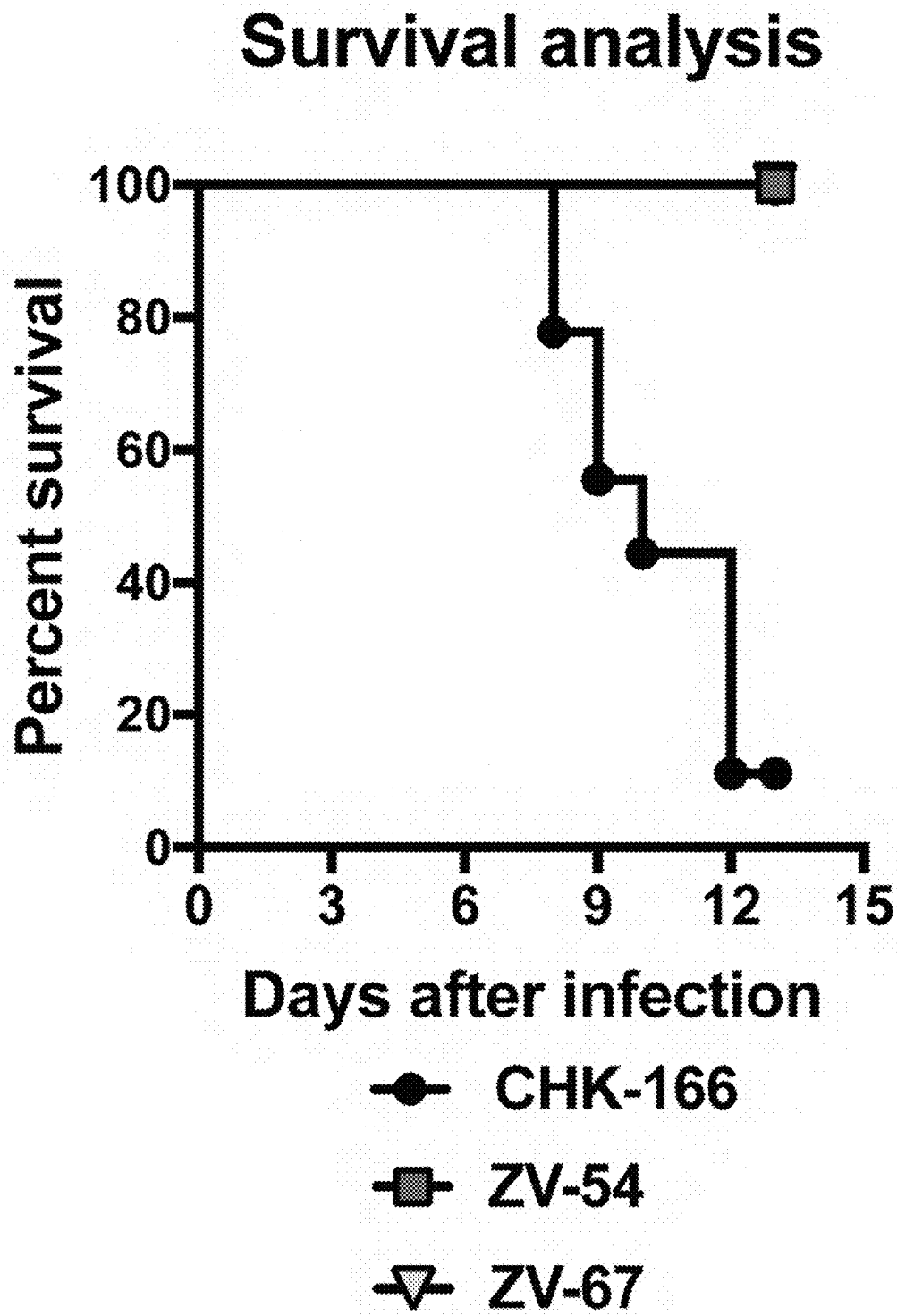

Recently, in vivo models of ZIKV pathogenesis in mice deficient in type I IFN signaling have been generated (Lazear et al., 2016; Rossi et al., 2016). A loss of Ifnar expression or blockade of Ifnar function was necessary because ZIKV does not replicate efficiently in wild-type (WT) mice due in part to a species-specific lack of antagonism of mouse Stat2 (Grant et al., 2016), a key signaling intermediate downstream of type I IFN signaling. To evaluate whether neutralizing mAbs protected against ZIKV infection in vivo, 4 to 5 week-old WT C57BL6 mice were treated at day −1 with anti-Ifnar (2 mg) and anti-ZIKV or isotype control mAbs (250 µg) and then animals were infected at day 0 with an African ZIKV strain that is more pathogenic in mice than isolates from Asia or the Americas (Lazear et al., 2016). Treatment of mice with anti-Ifnar mAb and a non-binding isotype control mAb (CHIKV-166 (Pal et al., 2013)) resulted in high levels of ZIKV RNA in serum at day 3 (FIG. 6A) and significant weight loss and mortality (FIG. 6B and FIG. 6C). In comparison, treatment with anti-Ifnar mAb and the DIII LR mAbs ZIKV-54 or ZIKV-67 resulted in reduced viremia and complete clinical protection. Thus, and consistent with a recent vaccine study that showed antibody-mediated protection against ZIKV viremia in BALB/c mice (Larocca et al., 2016), our neutralizing anti-ZIKV mAbs can protect against lethal ZIKV infection in IFN-deficient C57BL/6 mice; this model is a stringent test of protection since in humans the overwhelming majority of infections do not result in lethality.

Discussion for the Examples

Currently, there is no effective prevention or treatment of ZIKV infection other than avoidance of its mosquito vectors or travel to endemic regions. Given the potential devastating effects of this rapidly emerging infectious disease, the development of therapeutics and vaccines is considered a high priority. Herein, a panel of mAbs against ZIKV was developed that could provide insight into the epitopes that are recognized by neutralizing antibodies. This information could be used to focus vaccine efforts, inform the development of diagnostics with greater specificity, or alternatively, the antibodies themselves could be developed as therapeutics to prevent or mitigate infection during pregnancy. After inoculating mice with infectious ZIKV, a panel of ZIKV-specific mAbs were generated and characterized at both the functional and structural level. Four of the mAbs (ZV-48, ZV-54, ZV-64, and ZV-67) were ZIKV-specific, bound to sites within DIII and neutralized infection of a contemporary Asian strain of ZIKV. Whereas ZV-54 and ZV-67 neutralized other ZIKV strains efficiently, ZV-48 and ZV-64 showed reduced inhibitory activity against American and African ZIKV strains. Sequence analysis of the VL region of ZV-48 and ZV-64 suggest they are sibling clones, although the VH domains of the IgG heavy chains are distinct and make little contact with DIII. In comparison, the functionally related ZV-54 and ZV-67 mAbs have highly similar VL and VH sequences. From these analyses, three spatially distinct type-specific epitopes on ZIKV DIII (LR, C-C' loop, and ABDE sheet) with functionally different properties were identified. Finally, in vivo passive transfer studies revealed protective activity of ZV-54 and ZV-67 against an African ZIKV strain in a lethal challenge model in mice. Collectively, these results suggest that ZIKV DIII is targeted by distinct type-specific antibodies, some of which have neutralizing and protective activity.

Type-specific protective and neutralizing mAbs in DIII have been observed in studies with other flaviviruses including WNV (Beasley and Barrett, 2002; Oliphant et al., 2005; Sanchez et al., 2005), DENV (Brien et al., 2010; Gromowski and Barrett, 2007; Sukupolvi-Petty et al., 2010; Sukupolvi-Petty et al., 2013; Wahala et al., 2010), JEV (Goncalvez et al., 2008; Wu et al., 2003), and TBEV (Zlatkovic et al., 2013). As no other ZIKV-specific mAbs have been described to date, it remains uncertain whether the DIII epitopes reported here are immunodominant in humans. However, antibodies to DIII, which is prominently displayed on the surface of flaviviruses (Pierson and Diamond, 2013), appear less dominant in the human response against other flaviviruses (Beltramello et al., 2010; Jarmer et al., 2014; Smith et al., 2013). The structures of three other antibodies with reactivity against ZIKV have been published recently. Dai et al described the 3.0 Å structure of ZIKV E protein in complex with a cross-reactive murine antibody, 2A10G6 (Dai et al., 2016). This antibody bound the highly conserved fusion loop in DII and was poorly neutralizing (PRNT50 value of 249 µg/ml) yet still protected AG129 mice against lethal ZIKV infection, possibly through Fc effector mechanisms as was reported for fusion loop directed mAbs against WNV (Vogt et al., 2011). ZV-13 had a similar neutralizing profile in vitro and bound to an epitope on DII containing the fusion loop; although ZV-13 has not yet been tested in vivo, other fusion loop-specific mAbs (e.g., WNV E53 and WNV E60 (Oliphant et al., 2006)) showed little protective activity against ZIKV infection in mice (E. Fernandez, J. Govero, and M. Diamond, unpublished observations). In comparison, Barba-Spaeth et al reported 2.4 Å and 2.6 Å structures of ZIKV E protein complexed with mAbs C8 or A11 antibodies (Barba-Spaeth et al., 2016), both of which were generated by DENV-infected patients and recognize the EDE dimer epitopes (Rouvinski et al., 2015). These cross-reactive anti-DENV antibodies neutralized ZIKV infection and thus, identified an unrecognized link of neutralization across multiple flaviviruses. However, in this study, no protection experiments with C8 or A11 and ZIKV were undertaken in animals.

Three of the mAbs recognized cryptic epitopes in the ABDE sheet (ZV-2) and C-C' loop (ZV-48 and ZV-64) on DIII, which are not predicted to be accessible on the mature virion based on the cryo-electron microscopic structures of ZIKV H/PF/2013 (Kostyuchenko et al., 2016; Sirohi et al., 2016). So how were these antibodies generated in vivo? ZV-48 and ZV-64 were the product of serial infections with two different strains of ZIKV (MR-766 and H/PF/2013) and a final three-day boost with purified DIII prior to fusion and hybridoma generation. While it is possible that ZV-48 and ZV-64 were selected against the recombinant protein during the last boost, it seems more likely that (a) viral breathing (Dowd et al., 2011) allows exposure of the C-C' loop, as observed previously for a neutralizing DENV-1 mAb (Austin et al., 2012); or (b) the structure of MR-766 is distinct, and the C-C' loop epitope is more exposed. For ZV-2, it is more difficult to comprehend, as this mAb was a product only of repetitive prime-boosts with infectious ZIKV MR-766 and H/PF/2013. Although further study is warranted, other possible ways to generate antibodies against cryptic epitopes include exposure of the epitope on partially mature viruses (Nelson et al., 2008), SVPs, "broken" viral particles, or cleaved soluble envelope proteins. The binding studies with SVPs suggest that the C-C' loop but not the ABDE sheet epitope is accessible on SVPs.

The two mAbs (ZV-48 and ZV-64) that bound to the C-C' loop showed reduced neutralizing activity against the American and African strains. Sequence alignment of the C-C' loop contact residues in DIII of all four tested strains (FIG. 3 and data not shown) failed to reveal an obvious explanation for the loss of inhibitory activity relative to the Asian H/PF/2013 ZIKV strain. Only a single amino acid change (A343V) in the crystallographic footprint was identified in MR-766 and Dakar 41671, and this substitution was not present in the Paraiba 2015 sequence. So how is this loss of inhibitory activity for ZV-48 and ZV-64 explained? This phenotype is reminiscent of that observed with a neutralizing anti-mAb (DV1-E111) that also bound the C-C' loop of DIII, in this case, of DEW-1. With DV1-E111, a genotype-dependent pattern of neutralization was observed (Austin et al., 2012) that mapped to a single conservative amino acid substitution in DII remote from the footprint of the epitope (Dowd et al., 2015). Thus, the neutralizing activity of anti-flavivirus mAbs binding to the partially 'cryptic' C-C' loop epitope can be altered in an epitope-independent manner by natural strain variation that likely influences the ensembles of structures sampled by the virus.

Protection in vivo by the DIII LR neutralizing mAbs was observed using a model of lethal ZIKV infection in immunosuppressed adult mice receiving a blocking anti-Ifnar mAb. A key question remains whether passive transfer of neutralizing antibodies will protect pregnant women and their developing fetuses from ZIKV infection and congenital malformations, including microcephaly. Although mouse models of infection of pregnant dams with resultant injury to the developing fetus have recently been developed (Cugola et al., 2016; Miner et al., 2016), such protection studies were not performed because mice, in contrast to many other mammalian species, lack expression of the neonatal Fc receptor (FcRn) on their trophoblasts in the chorioallantoic placenta (Kim et al., 2009). Rather, FcRn is expressed in the mouse yolk sac endoderm, and thus, the transfer of IgG in mice is believed to be predominantly postnatal (Pentsuk and van der Laan, 2009). As reduced levels of transport of maternal or exogenous IgG into the fetus occur in mice, protection by a given antibody may be underestimated. Passive transfer studies with neutralizing antibodies during pregnancy may require experiments in mammals with more similar placental anatomy that are susceptible to ZIKV infection and disease (e.g., nonhuman primates).

The utilization of ZIKV type-specific mAb-based therapeutics has a potential advantage compared to cross-reactive mAbs: they would eliminate the risk of ADE associated with DENV infection, which could occur if levels of cross-reactive antibodies (e.g., EDE or fusion-loop antibodies) fell below the stoichiometric threshold of neutralization (Pierson et al., 2007). In studies in mice and nonhuman primates, administration of flavivirus cross-reactive antibodies targeting the fusion loop has resulted in enhanced infection and disease (Balsitis et al., 2010; Goncalvez et al., 2007; Zellweger et al., 2010), although in principle this can be overcome by genetic modification of the Fc region of the antibody (Williams et al., 2013).

These studies identify ZIKV DIII as a potential target of neutralizing antibodies, and thus a possible immunogen for generation of vaccines or boosting agents. DIII, either as recombinant protein or in a DNA plasmid, has been used by several groups in the context of different flavivirus vaccines (Block et al., 2010; Martina et al., 2008; Schneeweiss et al., 2011). Although neutralizing and protective antibodies are generated in several animal species, the titers have been lower than expected, possibly because of immunodominant sites on regions of DIII that normally are inaccessible on the viral particle. There structural analysis herein provides a hierarchy of neutralization efficacy associated with distinct epitopes on DIII. Masking of epitopes that fail to elicit neutralizing antibodies could be combined with epitope-focused vaccine design approaches (Correia et al., 2014) to generate DIII variants that induce more protective responses.

In summary, a panel of type-specific ZIKV mAbs were identified, several of which bind to distinct regions on DIII and have disparate functional activities that are related to the accessibility of their epitopes on the virion. The extensive characterization of these mAbs provide a path forward for developing prophylactic antibodies for use in pregnancy, therapeutic antibodies to potentially prevent viral persistence, or the design of domain and minimal epitope-specific vaccines against ZIKV. Such interventions might mitigate disease, and possibly minimize the risk of vaccine-associated Guillain-Barré syndrome, which likely occurs in the setting of humoral responses to an as yet unidentified ZIKV protein (Lucchese and Kanduc, 2016).

Methods for the Examples

Ethics statement. This study was carried out in accordance with the recommendations in the Guide for the Care and Use of Laboratory Animals of the National Institutes of Health. The protocols were approved by the Institutional Animal Care and Use Committee at the Washington University School of Medicine (Assurance no. A3381-01). Inoculations were performed under anesthesia that was induced and maintained with ketamine hydrochloride and xylazine, and all efforts were made to minimize animal suffering.

Cells. Vero cells (African green monkey kidney epithelial cells) and C6/36 Aedes albopictus cells were propagated in DMEM supplemented with fetal bovine serum (FBS, Omega) as described previously (Lazear et al., 2016). HEK-293T cells (human embryonic kidney) were maintained in DMEM supplemented with 7% FBS. K562 cells (human lymphoblast) were cultured in RPMI supplemented with 7% FBS.

Viruses. ZIKV strain H/PF/2013 (French Polynesia, 2013) was provided by the Arbovirus Branch of the Centers for Disease Control and Prevention with permission (X. de Lamballerie, Aix Marseille Université) (Baronti et al., 2014). ZIKV Brazil Paraiba 2015 was provided by S. Whitehead (Bethesda, MD) and originally obtained from P. F. C Vasconcelos (Instituto Evandro Chagas, Brazil). ZIKV MR-766 (Uganda, 1947) and Dakar 41519 (Senegal, 1982) were provided by the World Reference Center for Emerging Viruses and Arboviruses (R. Tesh, University of Texas Medical Branch). DENV strains (DENV-1 1254-4, DENV-2 172-08, DENV-3 N2845-09, DENV-4 N703-99) were isolated in Nicaragua and generously provided (E. Harris, University of California, Berkeley). Virus stocks were propagated in C6/36 cells after inoculating at a multiplicity of infection (MOI) of 0.01 and harvesting supernatants after 72, 96, or 120 h, as described previously (Lazear et al., 2016). To generate a mouse-adapted pathogenic variant, ZIKV Dakar 41519 was passaged in vivo in $Rag1^{-/-}$ mice (M. Gorman and M. Diamond, unpublished results) and a brain homogenate was used for all antibody protection studies in mice. Virus stocks were titrated by focus-forming assay (FFA) on Vero cells as described (Brien et al., 2013; Miner et al., 2016). Studies with ZIKV were conducted under biosafety level 2 (BSL2) and animal BSL3 (A-BSL3)

containment at Washington University School of Medicine with Institutional Biosafety Committee approval.

MAb generation. To generate anti-ZIKV mAbs, Irf3$^{-/-}$ mice were infected and boosted with $10^3$ FFU of ZIKV (MR-766 and H/PF/2013, respectively) and given a final intravenous boost with infectious $10^6$ FFU of ZIKV (H/PF/2013) (ZV-2 and ZV-13) or purified DIII (ZV-48, ZV-54, ZV-64, and ZV-67) three days prior to fusion with P3X63.Ag.6.5.3 myeloma cells. Hybridomas secreting antibodies that reacted with ZIKV-infected Vero cells were identified by flow cytometry and cloned by limiting dilution. All mAbs were purified by protein A affinity chromatography. The VH and VL sequences of mAbs ZV-2, ZV-48, ZV-64, and ZV-67 were amplified from hybridoma cell RNA by a 5' RACE procedure.

ZIKV mAbs domain mapping by ELISA. A MAXISORP 96-well plate (Nunc) was coated with 50 µl of 2 µg/ml of recombinant ZIKV E, ZIKV E-FL (fusion loop mutant), ZIKV DIII, WNV-E or DV4-E overnight at 4° C. Plates were washed three times in ELISA washing buffer (PBS with 0.02% Tween 20) followed by incubation with ELISA blocking buffer (PBS, 2% bovine serum albumin, and 0.02% Tween 20) for 1 h at 37° C. MAbs (0.5 µg/ml) were added for 1 h at room temperature. Plates were washed again and then sequentially incubated with 2 µg/ml of horseradish peroxidase-conjugated anti-mouse IgG and tetramethylbenzidine substrate. The reaction was stopped by the addition of 1 N H2SO4 to the medium, and emission (450 nm) was read using an iMark microplate reader (Bio-Rad).

Neutralization assays. Serial dilutions of mAb were incubated with 100 FFU of different ZIKV for one hour at 37° C. MAb-virus complexes were added to Vero cell monolayers in 96-well plates. After 90 minutes, cells were overlaid with 1 (w/v) methylcellulose in Modified Eagle Media (MEM) supplemented with 4% FBS. Plates were harvested 40 h later, and fixed with 1% PFA in PBS. The plates were incubated sequentially with 500 ng/ml of ZV-16 (E. Fernandez, unpublished results) and horseradish peroxidase (HRP)-conjugated goat anti-mouse IgG in PBS supplemented with 0.1% saponin and 0.1% BSA. ZIKV-infected foci were visualized using TrueBlue peroxidase substrate (KPL) and quantitated on an ImmunoSpot 5.0.37 macroanalyzer (Cellular Technologies Ltd). Non-linear regression analysis was performed, and EC50 values were calculated after comparison to wells infected with ZIKV in the absence of antibody.

MAb binding to flavivirus-infected cells. Vero or C6/36 cells were inoculated with different flaviviruses (ZIKV H/PF/2013, DENV-1 1254-4, DENV-2 172-08, DENV-3 N2845-09, and DENV-4 N703-99) in DMEM supplemented with 10 mM HEPES, penicillin and streptomycin, and 10% FBS. At different time points after infection (ZIKV H/PF/2013, MOI of 5, 24 h, Vero cells; DENV-1 1254-4, DENV-2 172-08, DENV-3 N2845-09, DENV-4 N703-99, MOI of 0.01, 120 h, C6/36 cells), cells were rinsed with PBS, detached, and centrifuged at 300×g for 5 min. Cells were fixed with 4% paraformaldehyde (PFA, Electron Microscopy Sciences) diluted in PBS for 20 min at room temperature and permeabilized with HBSS (Invitrogen), 10 mM HEPES, 0.1% saponin (Sigma), and 0.025% NaN3 (Sigma) (Perm buffer) for 10 min at room temperature. Cells then were rinsed one additional time with Perm buffer. Fifty-thousand cells were transferred to a U-bottom plate and incubated for 1 h at 4° C. with 10 µg/ml of anti-ZIKV mAbs or isotype controls (negative, CHK-166 (Pal et al., 2013); positive, WNV E53 (Oliphant et al., 2006)). After washing, cells were incubated with an Alexa Fluor 647-conjugated goat anti-mouse IgG (Invitrogen) for 1 h at 4° C. Cells were fixed in 1 PFA in PBS, processed on a FACS Array (BD Biosciences) and analyzed using FlowJo software (Tree Star).

Biolayer interferometry binding assays. The binding affinity of purified ZIKV E or ZIKV DIII protein with ZIKV mAbs was monitored by BLI using an Octet-Red96 device (Pall ForteBio). Briefly, 100 µg of each antibody was mixed with biotin (EZ-Link-NHS-PEG4-Biotin, Thermo Fisher) at a molar ratio of 20:1 biotin:protein and incubated at room temperature for 30 min. The unreacted biotin was removed by passage through a desalting column (5 ml Zeba Spin 7K MWCO, Thermo Fisher). The antibodies were loaded onto streptavidin biosensors (ForteBio) until saturation, typically 2 µg/ml for 3 min, in HBS-EP buffer (10 mM Hepes, pH 7.4, 150 mM NaCl, 3 mM EDTA, and 0.005% P20 surfactant) with 1% BSA. Association and dissociation were measured at 25° C. for all mAbs. Dissociation of the complexes was monitored by dipping sensors in binding buffer alone. The real-time data were analyzed using Biaevaluation 4.1 (GE Healthcare). Association and dissociation profiles, as well as steady-state equilibrium concentration curves, were fitted assuming a 1:1 binding model.

SVP production and binding assay. ZIKV SVPs were generated as described previously for WNV (Hanna et al., 2005). Briefly, a plasmid encoding the prM-E gene of ZIKV H/PF/2013 was transfected into HEK-293T cells. Transfected cells were incubated at 30° C., and SVPs were harvested every 24 h post-transfection were filtered through a 0.2 pm filter and stored aliquoted at −80° C. For binding assays, 96-well high-binding plates (Immulon 4HBX; Thermo Scientific) were coated with 1 µg/ml of ZV-67 in coating buffer (15 mM sodium carbonate, 35 mM sodium bicarbonate, pH 9.6) overnight at 4° C. Between each step, plates were washed three times with PBS+1.5% Tween 20 (PBS-T). Plates were blocked with PBS-T+1.5% BSA, followed by capture of SVPs diluted in blocking buffer for 1 h at 37° C. Plates were incubated with the indicated concentrations of biotin-conjugated monoclonal antibodies (ZV-2, ZV-13, ZV-48, ZV-54, ZV-64, ZV-67) for 30 min at 37° C., followed by incubation with 30 ng/ml streptavidin-HRP for 30 min at 37° C. The plates were developed with SureBlue TMB substrate (KPL) and stopped with 1 M HCl. Plates were analyzed at 450 nm, with a 570 nm correction (BioTek).

ADE studies. RVP production and subsequent ADE assays were performed using approaches detailed in prior studies with WNV and DENV RVPs (Dowd et al., 2011; Obara et al., 2013; Pierson et al., 2007). Briefly, plasmids expressing the C-prM-E genes of ZIKV H/PF/2013 or DENV-2 16881 were co-transfected into HEK-293T cells with a plasmid encoding a WNV replicon expressing GFP. Transfected cells were incubated at 30° C. and RVPs harvested on days 3-6 post-transfection, filtered through a 0.2 pM filter, and stored aliquoted at −80° C. For ADE studies, RVPs were incubated with serial dilutions of mAb under conditions of antibody excess for 1 h at 37° C. to allow for steady-state binding, followed by infection of FcγRIIa$^+$ K562 cells. Infections were carried out at 37° C. and GFP-positive infected cells detected by flow cytometry 48 h later.

Mouse protection experiments. Mice were purchased from Jackson Laboratories (WT C57BL/6J, #000664). Mice (4 to 5 week-old) were inoculated with ZIKV by subcutaneous (footpad) route with $10^5$ FFU of mouse-adapted ZIKV Dakar in a volume of 50 µL. One day prior to ZIKV infection, mice were treated with 2 mg of an Ifnar-blocking mAb (MAR1-5A3) (produced by Leinco Technologies)

(Sheehan et al., 2006) by intraperitoneal injection, as described previously (Lazear et al., 2016). ZIKV mAbs were administered as a single 250 μg dose one day before infection via an intraperitoneal route. Survival and weight loss were monitored. Serum samples were obtained at day 3 after ZIKV infection and extracted with the Viral RNA Mini Kit (serum) (QIAGEN). ZIKV RNA levels were determined by TaqMan one-step quantitative reverse transcriptase PCR (qRT-PCR) on an ABI 7500 Fast Instrument using standard cycling conditions. Viral burden is expressed on a log 10 scale as viral RNA equivalents per milliliter after comparison with a standard curve produced using serial 10-fold dilutions of ZIKV RNA. A published primer set was used to detect ZIKV RNA (Lanciotti et al., 2008): forward, 5'-CCGCTGCCCAACACAAG-3'; reverse, 5'-CCACTAACGTTCTTTTGCAGACAT-3'; probe, 5'-/56-FAM/AGCCTACCT/ZEN/TGACAAGCAATCA-GACACTCAA/3IABkFQ/-3' (Integrated DNA Technologies).

Protein production, purification, and crystallization. A cDNA encoding the full-length prM and ectodomain of E of ZIKV (strain H/PF/2013, residues 123-696, GenBank Accession KJ776791) was placed in the mammalian expression vector pFM1.2 (Mancia et al., 2004) downstream of a human IL-2 signal sequence peptide (MPLLLLLPLLWA-GAL) and terminated with a hexahistidine affinity tag. The protein was expressed by transient transfection of Expi293F cells using HYPE-5 reagent (Oz Biosciences) in serum-free Expi293 medium (Thermo Fisher). Cell supernatants were harvested 72 h after transfection. The soluble E protein was recovered by capture on nickel agarose beads (Goldbio) and purified by passage over S200 Superdex. The protein storage buffer contained 25 mM HEPES-HCl pH 7.4, 150 mM NaCl, and 0.01% sodium azide at 4° C. A ZIKV quad-fusion-loop variant (ZIKV E-FL) was made by site-directed mutagenesis (T76A, Q77G, W101R, L107R, as numbered from the mature N-terminus). A cDNA encoding the full-length prM and ectodomain of E DENV-4 (residues 113-678 of strain H241, GenBank accession AY947539) was inserted into pFM1.2 vector for transient expression in Expi293F cells. WNV E ectodomain (residues 291-694 of strain New York 1999, GenBank accession YP001527877) was produced in bacteria and refolded as described previously (Oliphant et al., 2007).

An untagged form of ZIKV DIII (strain H/PF/2013, residues 299 to 407) was cloned into the pET21a vector (Novagen) and expressed by IPTG-induction in BL21 (DE3) bacterial cells (Agilent). Isolated inclusion bodies were solubilized and oxidatively re-folded, as previously described for WNV DIII (Nybakken et al., 2005). ZV-48 scFv was engineered with a (GGGGS)$_3$ linker between the VL and VH domains, cloned into the pET21a vector, and expressed in the BL21 (DE3) as inclusion bodies. The ZV-48 scFv was refolded in vitro in a manner similar to ZIKV DIII.

After protein A affinity purification, the ZV-2, ZV-64 and ZV-67 IgG were cleaved with immobilized papain (Pierce Biotechnology), and Fab fragments were recovered by passage over a second protein A affinity column to remove cleaved Fc and any uncleaved IgG. The ZV-48 scFvs were complexed with excess DIII and purified by size exclusion chromatography in 150 mM NaCl and 20 mM HEPES pH 7.5. The ZV-48 scFv-DIII complexes were crystallized by hanging drop vapor diffusion at 14 mg/ml in 0.2 M Ammonium sulfate and 15% (w/v) PEG 4000. Crystals were cryo-protected in a solution containing 20% ethylene-glycol and cooled in liquid nitrogen for data collection. Concentrated Fab and DIII preparations were mixed at a 1:1 stoichiometry, incubated at 4° C. overnight, then used for crystallization trials without further purification. Diffraction-quality crystals of ZV-2-DIII complex were obtained in 0.1 M MES pH 6.5, 0.6 M NaCl and 20.6% PEG 4000 at 13 mg/ml. Diffraction-quality crystals of ZV-64-DIII were obtained in 0.1 M sodium acetate and 22% PEG 4000 at 15 mg/ml. Diffraction-quality crystals of ZV-67-DIII were obtained in 0.2 M Ammonium formate, 20% PEG 3350 at 14 mg/ml.

Structure determination and refinement. Fine-sliced diffraction data were collected at ALS beam line 4.2.2 (Molecular Biology Consortium) at 100 K at a wavelength of 1.0 Å using a CMOS detector in shutter-less mode. Data were processed in XDS (Kabsch, 2010) and scaled using AIMLESS (Evans and Murshudov, 2013). Molecular replacement phasing was accomplished in PHENIX (Adams et al., 2010) using the PHASER GUI (McCoy et al., 2007), with the structure of ZV-2 in complex with ZIKV DIII (H/PF/2013) determined first using the coordinates of WNV E16-DIII (RCSB:1ZTX) (Nybakken et al., 2005) assembled as three probes (VLVH, CLCH, and DIII) and subsequent structures determined using ZV-2-DIII coordinates. Repeated cycles of model building and atomic refinement were carried out in COOT (Emsley et al., 2010) and PHENIX. A summary of the data collection and refinement statistics is provided in Table 2.

Structural analysis. Antibody-antigen contacts were assessed using HBPLUS employing default settings (McDonald and Thornton, 1994), buried surfaces were calculated using AREAIMOL (Lee and Richards, 1971), and shape complementarity was measured using Sc (Lawrence and Colman, 1993). All structural representations were colored and rendered using the PyMOL Molecular Graphics System (www.pymol.org).

Statistical analysis. All virological data were analyzed with GraphPad Prism software. Kaplan-Meier survival curves were analyzed by the log rank test, and weight losses and viremia were compared using an ANOVA with a multiple comparisons test. A P value of <0.05 indicated statistically significant differences. SVP ELISA data were analyzed by non-linear regression analysis using a one-site binding model.

TABLE 1

Characteristics of anti-ZIKV mAbs.

| mAb | Priming[a] | % Neutralization (undiluted sups)[b] | Isotype[c] | Domain localization and epitope[d] | Cross-reactivity[e] | Affinity for DIII or ZIKV E $K_D$ (nM)[f] | $t_{1/2}$[g] (min) |
|---|---|---|---|---|---|---|---|
| ZV-2 | Virus | <30 | IgG2c | DIII (ABDE sheet) | none | 266 ± 42 | 0.3 |
| ZV-13 | Virus | <30 | IgG2c | DI-II (fusion loop) | WNV, JEV, DENV-1, -2, -3, -4 | 254 ± 10 | 3.3 |

TABLE 1-continued

Characteristics of anti-ZIKV mAbs.

| mAb | Priming[a] | % Neutralization (undiluted sups)[b] | Isotype[c] | Domain localization and epitope[d] | Cross-reactivity[e] | Affinity for DIII or ZIKV E $K_D$ (nM)[f] | $t_{1/2}$[g] (min) |
|---|---|---|---|---|---|---|---|
| ZV-48 | Virus + DIII | 100 | IgG2c | DIII (C-C' loop) | none | 35 ± 0.8 | 3.2 |
| ZV-54 | Virus + DIII | 100 | IgG2c | DIII (LR) | none | 7.9 ± 0.2 | 33.0 |
| ZV-64 | Virus + DIII | 98 | IgG2c | DIII (C-C' loop) | none | 32 ± 13 | 1.0 |
| ZV-67 | Virus + DIII | 100 | IgG2c | DIII (LR) | none | 8.8 ± 1.7 | 13.8 |

[a]To generate mAbs, mice were infected and boosted with 10³ FFU of ZIKV (MR-766 and H/PF/2013, respectively) and given a final intravenous boost with live ZIKV (H/PF/2013) or purified DIII.
[b]Undiluted hybridoma supernatant (~20 µg/ml) was incubated with 10² FFU of ZIKV (strain H/PF/2013) for one hour at 37° C. Virus-mAb mixtures were added to Vero cell monolayers for one hour at 37° C. prior to addition of a methylcellulose overlay (described in the Methods). The percent neutralization was determined compared to medium alone. Results are representative of at least three independent experiments.
[c]MAb isotype was determined using a commercial ELISA kit.
[d]Domain localization and epitope was determined by binding to WT or mutant recombinant proteins or X-ray crystallography (see FIG. 1 and FIG. 3).
[e]Cross-reactivity was determined by flow cytometric analysis of flavivirus-infected cells.
[f]$K_D$ (equilibrium) were determined by BLI with ZIKV E (ZV-13) or DIII (ZV-2, ZV-48, ZV-54, ZV-64, ZV-67) as described in FIG. 2 and FIG. 7.
[g]Calculated from the dissociation constant, $k_d$ kinetic.

TABLE 2

Data collection and refinement statistics.

| | ZV-2 Fab/DIII complex | ZV-48 scFv/DIII complex | ZV-64 Fab/DIII complex | ZV-67 Fab/DIII complex |
|---|---|---|---|---|
| PDB ID code | 5KVD | KDVE | 5KVF | 5KVG |
| Unit-cell, Å | | | | |
| Space group | $P2_12_12_1$ | $C222_1$ | $P2_12_12_1$ | $P2_12_12_1$ |
| [a]Resolution range, Å | 33.65-1.65 (1.71-1.65) | 48.5-1.170 (1.76-1.70) | 19.63-14.0 (1.45-1.40) | 57.54-1.40 (1.45-1.40) |
| Total reflections | 479367 (47934) | 645120 (57943) | 1093004 (103810) | 3080888 (292949) |
| Unique reflections | 71306 (7038) | 44589 (4335) | 104933 (10362) | 111954 (11045) |
| Average multiplicity | 6.7 (6.8) | 14.5 (13.3) | 10.4 (10.0) | 27.5 (26.5) |
| Mean I/σ (I) | 18.78 (2.12) | 14.28 (1.60) | 19.70 (1.83) | 22.62 (2.13) |
| Completeness, % | 99 (99) | 98 (96) | 100 (100) | 100 (100) |
| Rmerge | 0.0592 (0.9598) | 0.1504 (1.9540) | 0.0821 (1.4200) | 0.1098 (1.7170) |
| Rmeas | 0.0642 (1.0390) | 0.1559 (2.0320) | 0.0864 (1.4970) | 0.1119 (1.7500) |
| CC1/2 | 0.999 (0.723) | 0.999 (0.723) | 0.999 (0.595) | 1 (0.789) |
| CC* | 1 (0.916) | 1 (0.916) | 1 (0.864) | 1 (0.939) |
| Refinement | | | | |
| Rwork | 0.1901 (0.2747) | 0.1870 (0.3100) | 0.1538 (0.2458) | 0.1489 (0.1973) |
| [b]Rfree | 0.2214 (0.2916) | 0.2134 (0.3361) | 0.1866 (0.3038) | 0.1794 (0.2519) |
| CC(work) | 0.967 (0.789) | 0.963 (0.844) | 0.970 (0.826) | 0.971 (0.906) |
| CC(free) | 0.949 (0.727) | 0.964 (0.725) | 0.963 (0.726) | 0.964 (0.843) |
| Number of Atoms | | | | |
| non-hydrogen atoms | 4961 | 3210 | 4911 | 5121 |
| macromolecules | 4253 | 2554 | 4205 | 4109 |
| ligands | 18 | 39 | 30 | 2 |
| Protein residues | 550 | 331 | 546 | 540 |
| Solvent molecules | 690 | 619 | 675 | 1009 |
| RMS(bonds) | 0.004 | 0.003 | 0.005 | 0.006 |
| RMS(angles) | 0.76 | 0.67 | 0.85 | 0.94 |
| Coordinate error (MLH) | 0.21 | 0.21 | 0.16 | 0.13 |
| Ramachandran, favored, % | 98 | 98 | 98 | 99 |
| Ramachandran, allowed, % | 2.00 | 1.90 | 1.50 | 0.97 |
| Ramachandran, outliers, % | 0 | 0 | 0 | 0 |
| Clashscore | 2.72 | 3.33 | 2.99 | 1.36 |
| B-factor Model | 25 TLS groups | 26 TLS groups | anisotropic | anisotropic |
| Average B factor, Å² | 31.68 | 29.48 | 21.45 | 20.94 |

TABLE 2-continued

Data collection and refinement statistics.

|  | ZV-2 Fab/DIII complex | ZV-48 scFv/DIII complex | ZV-64 Fab/DIII complex | ZV-67 Fab/DIII complex |
|---|---|---|---|---|
| macromolecules | 30.56 | 25.98 | 19.50 | 17.98 |
| ligands | 34.31 | 73.38 | 33.71 | 20.45 |
| solvent | 38.55 | 41.19 | 33.06 | 32.97 |

$^a$Values in parentheses refer to the highest resolution shell.

$^b$Rfree = free R factor based on random 5% of all data. Diffraction source was ALS BL4.2.2 using detector RDI CMOS_8M. Data processing, scaling statistics, and refinement statistics are described in the Methods.

TABLE 3

Van der Waals contacts for Fab and scFv DIII complexes.

| DIII | ZV-2 | DIII | ZV-67 |
|---|---|---|---|
| $Lys^{E301}$ | $Ile^{H30}(1)$ | $Thr^{E309}$ | $Tyr^{H32}(4)$ |
| $Thr^{E315}$ | $Ser^{L56}(1)$ | $Ala^{E310}$ | $Asn^{H96}(3), Tyr^{H32}(1)$ |
| $Lys^{E316}$ | $Tyr^{H100A}(12), Asp^{H101}(1)$ | $Ala^{E311}$ | $Asn^{H96}(7), Tyr^{H97}(2)$ |
| $Ile^{E317}$ | $Tyr^{H100A}(3)$ | $Phe^{E312}$ | $Ser^{L50}(1)$ |
| $Pro^{E318}$ | $Tyr^{H100A}(2)$ | $Thr^{E313}$ | $Ser^{L50}(3), Tyr^{H97}(2)$ |
| $Ala^{E319}$ | $Tyr^{H100A}(3), Tyr^{H100}(3)$ | $Phe^{E314}$ | $Thr^{L31}(1)$ |
| $Glu^{E320}$ | $Asn^{L30D}(4), Tyr^{H100}(2)$ | $Gln^{E331}$ | $Tyr^{H97}(3)$ |
| $Thr^{E321}$ | $Asn^{L30D}(5), Gly^{H98}(3)$ | $Tyr^{E332}$ | $Tyr^{H97}(5)$ |
| $Leu^{E322}$ | $His^{L30A}(4), Tyr^{L32}(1), Asn^{L30D}(1), Gly^{L30C}(1)$ | $Ala^{E333}$ | $Tyr^{H97}(13), Asn^{H96}(1)$ |
| $Thr^{E327}$ | $Tyr^{H100A}(2), Tyr^{H96}(1), Ser^{H99}(1)$ | $Gly^{E334}$ | $Ser^{H31}(2)$ |
| $Glu^{E329}$ | $Try^{H32}(5), Arg^{H94}(5)$ | $Thr^{E335}$ | $Ser^{H31}(7), Thr^{H30}(4), Tyr^{H52}(1)$ |
|  |  |  | $Arg^{H53}(5), Tyr^{H32}(1)$ |
| $Asn^{E362}$ | $Ile^{H30}(3)$ | $Asp^{E336}$ | $Ser^{H31}(2)$ |
| $Val^{E364}$ | $Thr^{H28}(4)$ | $Gly^{E337}$ | $Arg^{H53}(1)$ |
| $Ile^{E385}$ | $Thr^{H28}(1)$ | $Ser^{E368}$ | $Arg^{H53}(3)$ |
| $Thr^{E366}$ | $Thr^{H28}(3)$ | $Glu^{E370}$ | $Tyr^{L94}(1), Tyr^{H52}(6), Asn^{H56}(4), Tyr^{H58}(5)$ |
| $Glu^{E367}$ | $Gly^{H26}(8), Tyr^{H27}(3), Ser^{H25}(3)$ | $Asn^{E371}$ | $Tyr^{L94}(3), Tyr^{L96}(3), Tyr^{H97}(6)$ |
| $Ser^{E372}$ | $Gly^{H26}(4), Tyr^{H27}(3)$ | $Glu^{E393}$ | $Tyr^{L49}(4), Tyr^{L55}(4), Thr^{L56}(4)$ |
| $Lys^{E373}$ | $Tyr^{H32}(1), Val^{H2}(1), Gly^{H26}(1),$ | $Lys^{E394}$ | $Leu^{L46}(1), Tyr^{L49}(11), Asn^{H96}(5),$ |
|  | $Tyr^{H27}(4), Thr^{H28}(2), Tyr^{H102}(1)$ |  | $Gly^{H98}(3)$ |
| $Met^{E374}$ | $Tyr^{H32}(4), Thr^{H28}(1)$ | $Lys^{E395}$ | $Tyr^{L49}(5)$ |
| $Met^{E375}$ | $Tyr^{H32}(5), Tyr^{H96}(4), Tyr^{H100A}(2)$ |  | $Asn^{L53}(3)$ |
| $Glu^{E377}$ | $Try^{H96}(5)$ | $Thr^{E397}$ | $Asn^{L53}(2)$ |

| DIII | ZV-48 | DIII | ZV-64 |
|---|---|---|---|
| $Leu^{E307}$ | $Asn^{L30C}(1), Asn^{L30D}(1), Glu^{L30E}(5)$ | $Leu^{E307}$ | $Asn^{L30D}(3), Gln^{L30E}(3), Ser^{L30C}(1)$ |
| $Lys^{E340}$ | $Ser^{L30B}(3), Asn^{L30C}(1), Glu^{L30E}(5)$ | $Lys^{E340}$ | $Ser^{L30B}(3)$ |
| $Pro^{E342}$ | $Asn^{L30C}(1)$ | $Pro^{E342}$ | $Ser^{L30C}(2)$ |
| $Ala^{E343}$ | $Asn^{L30C}(3)$ | $Ala^{E343}$ | $Ser^{L30C}(5)$ |
| $Gln^{E344}$ | $Tyr^{L30A}(2), Asn^{L30D}(1), Tyr^{L32}(1)$ | $Gln^{E344}$ | $Tyr^{L30A}(2), Asn^{L30D}(1), Tyr^{L32}(1)$ |
| $Val^{E347}$ | $Tyr^{L94}(1,)Trp^{H33}(4), Met^{H50}(1)$ | $Val^{E347}$ | $Tyr^{L94}(1), Trp^{H33}(4), Met^{H50}(1)$ |
| $Asp^{E348}$ | $Trp^{H33}(6)$ | $Asp^{E348}$ | $Tyr^{L94}(1), Trp^{H33}(8), His^{H35}(1)$ |
| $Gln^{E350}$ | $Tyr^{L32}(1), Arg^{H94}(1), Leu^{H95}(4),$ | $Gln^{E350}$ | $Ser^{H31}(1), Tyr^{L95}(1), Tyr^{H96}(2), Tyr^{H97}(5)$ |
|  | $Gly^{H96}(4), Asn^{H97}(4), Met^{H99}(6)$ |  |  |
| $Thr^{E351}$ | $Tyr^{L32}(1), Trp^{L50}(1), Tyr^{L91}(2), Tyr^{L96}(3),$ | $Thr^{E351}$ | $Tyr^{L32}(1), Trp^{L50}(2), Tyr^{L91}(2),$ |
|  | $Leu^{H95}(1), Gly^{H96}(1), Asn^{H97}(3)$ |  | $Tyr^{L96}(3), Tyr^{H97}(1)$ |
| $Leu^{E352}$ | $Tyr^{L32}(6)$ | $Leu^{E352}$ | $Tyr^{L32}(6)$ |
| $Thr^{E353}$ | $Tyr^{L32}(2), Tyr^{L91}(6),$ | $Thr^{E353}$ | $Tyr^{L32}(2), Tyr^{L91}(5), Tyr^{L92}(2),$ |
|  | $Tyr^{L92}(2), Tyr^{L94}(4),$ |  | $Tyr^{L94}(4), Tyr^{L96}(4)$ |
|  | $Tyr^{L96}(4)$ |  |  |
| $Pro^{E354}$ | $Tyr^{L30A}(10), Tyr^{L32}(1), Tyr^{L92}(1)$ | $Pro^{E354}$ | $Tyr^{L30}(1), Tyr^{L30A}(5), Tyr^{L92}(1)$ |
| $Leu^{E358}$ | $Asn^{L30C}(1)$ | $Val^{E355}$ | $Tyr^{L94}(1)$ |
| $Asp^{E384}$ | $Asn^{H56}(4)$ | $Leu^{E358}$ | $Ser^{L30C}(1)$ |
| $Tyr^{E386}$ | $Asn^{H31}(1)$ | $Val^{E391}$ | $Asn^{L30D}(1), Lys^{L30F}(1)$ |

Van der Waals contacts summary

|  | CDR-H1 26-32 | CDR-H2 52-56 | CDR-H3 95-102 | FRM-H | Total $V_H$ | CDR-L1 24-34 | CDR-L2 50-56 | CDR-L3 89-97 | FRM-L | Total $V_L$ |
|---|---|---|---|---|---|---|---|---|---|---|
| ZV-2 | 56 | 0 | 45 | 6 | 107 | 16 | 1 | 0 | 0 | 17 |
| ZV-48 | 2 | 4 | 23 | 12 | 41 | 46 | 1 | 23 | 0 | 70 |
| ZV-64 | 1 | 0 | 9 | 14 | 24 | 39 | 2 | 24 | 0 | 65 |
| ZV-67 | 21 | 20 | 50 | 5 | 96 | 1 | 17 | 7 | 21 | 46 |

Summary of van der Waals contacts across the interface in different mAb/DIII complexes. The amino acids are labeled (in superscript) to indicate their specific positions in the heavy chain (H), light chain (L) or DIII (E) sequences. Interactions were determined using HBPLUS (McDonald, 1994) using a cutoff distance of 3.9 Å.

TABLE 4

Hydrogen bond contacts for Fab and scFv DIII complexes with DIII.

| DIII | ZV-2 | DIII | ZV-67 |
|---|---|---|---|
| \multicolumn{4}{c}{Direct hydrogen bonds} | | | |
| Ile$^{E317}$(O) | Tyr$^{H100A}$(OH) | Ala$^{E311}$(N) | Asn$^{H96}$(OD1) |
| Glu$^{E320}$(O) | Asn$^{L30D}$(ND2) | Thr$^{E313}$(OG1) | Ser$^{L50}$(OG) |
| Thr$^{E327}$(O) | Tyr$^{H100A}$(OH) | Thr$^{E335}$(O) | Arg$^{H53}$(NH1) |
| Glu$^{E329}$(OE2) | Tyr$^{H32}$(OH), Arg$^{H94}$(NH1) | Thr$^{E335}$(N) | Ser$^{H31}$(O) |
| Val$^{E364}$(O) | Thr$^{H28}$(OG1) | Thr$^{E335}$(OG1) | Thr$^{H30}$(O) |
| Glu$^{E367}$(OE2) | Gly$^{H26}$(N) | Asn$^{E371}$(ND2) | Tyr$^{L94}$(OH) |
| Lys$^{E373}$(NZ) | Tyr$^{H102}$(OH) | Gly$^{E337}$(O) | Arg$^{H53}$(NH1) |
| Lys$^{E373}$(N) | Gly$^{H26}$(O) | Glu$^{E370}$(OE2) | Asn$^{H56}$(ND2), Tyr$^{H58}$(OH) |
| Lys$^{E373}$(O) | Thr$^{H28}$(N) | Asn$^{E371}$(OD1) | Tyr$^{H97}$(OH) |
| Glu$^{E377}$(OE1) | Tyr$^{H96}$(OH) | Lys$^{E394}$(NZ) | Asn$^{H96}$(O), Gly$^{H98}$(O) |
| | | Lys$^{E395}$(O) | Tyr$^{L49}$(OH) |
| | | Thr$^{E397}$(N) | Asn$^{L53}$(OD1) |
| \multicolumn{4}{c}{Indirect (solvent mediated) hydrogen bonds} | | | |
| Thr$^{E315}$(O) | Ser$^{L56}$(OG) | Thr$^{E313}$(OG1) | Ser$^{L5}$(OG) |
| Lys$^{E316}$(O) | Tyr$^{H100A}$(OH) | Phe$^{E314}$(O) | Thr$^{L31}$(OG1) |
| Ile$^{E317}$(O) | Tyr$^{L49}$(OH) | Gln$^{E331}$(OE1) | Phe$^{L91}$(O) |
| Glu$^{E320}$(OE2) | Gly$^{L30C}$(O) | Ala$^{E333}$(O) | Glu$^{L95}$(O) |
| Thr$^{E366}$(OG1) | Tyr$^{H27}$(O) | Thr$^{E335}$(OG1) | Ser$^{L43}$(O) |
| Asn$^{E371}$(O) | Gly$^{H26}$(O) | Glu$^{E370}$(OE1) | Ser$^{H54}$(OG) |
| Ser$^{E372}$(OG) | Thr$^{H28}$(OG1) | Asn$^{E371}$(OD1) | Tyr$^{L52}$(OH) |
| Met$^{E375}$(O) | Tyr$^{H96}$(OH) | Thr$^{E397}$(OG1), Thr$^{E397}$(O) | Ser$^{L52}$(OG), Asn$^{L53}$(OD1) |
| Glu$^{E377}$(OE1) | TyrH97(O) | | |

| DIII | ZV-48 | DIII | ZV-64 |
|---|---|---|---|
| \multicolumn{4}{c}{Direct hydrogen bonds} | | | |
| Lys$^{E340}$(NZ) | Ser$^{L30B}$(O), Glu$^{L30E}$(OE2) | Lys$^{E340}$(NZ) | Ser$^{L30B}$(O) |
| Ala$^{E343}$(O) | Asn$^{L30C}$(ND2) | Ala$^{E343}$(N) | Ser$^{L30C}$(OG) |
| Gln$^{E344}$(OE1) | Asn$^{L30D}$(ND2) | Ala$^{E343}$(O) | Ser$^{L30C}$(OG) |
| Val$^{E347}$(O) | Trp$^{H33}$(NE1) | Val$^{E347}$(O) | Trp$^{H33}$(NE1) |
| Gln$^{E350}$(NE2) | Gly$^{H96}$(O), Met$^{H99}$(O) | Gln$^{E350}$(O) | Tyr$^{H97}$(N) |
| Gln$^{E350}$(O) | Asn$^{H97}$(ND2) | Thr$^{E351}$(OG1) | Tyr$^{L96}$(OH) |
| Thr$^{E351}$(OG1) | Tyr$^{L96}$(OH) | Leu$^{E352}$(O) | Tyr$^{L32}$(OH) |
| Leu$^{E352}$(O) | Tyr$^{L32}$(OH) | Thr$^{E353}$(OG1) | Tyr$^{L91}$(O), Tyr$^{L96}$(OH) |
| Thr$^{E353}$(OG1) | Tyr$^{L96}$(OH), Tyr$^{L91}$(O) | | |
| Asp$^{E384}$(OD2) | Asn$^{H56}$(ND2) | | |
| \multicolumn{4}{c}{Indirect (solvent mediated) hydrogen bonds} | | | |
| Tyr$^{E305}$(O) | Glu$^{L30E}$(OE2) | Val$^{E341}$(O) | Ser$^{L30C}$(OG) |
| Val$^{E341}$(O) | Asn$^{L30C}$(O) | Asp$^{E348}$(OD2) | His$^{H35}$(NE2) |
| Asp$^{E348}$(OD2) | His$^{H35}$(NE2) | Met$^{E349}$(O) | Tyr$^{H97}$(O) |
| Gln$^{E350}$(OE1) | Trp$^{H33}$(O) | Asp$^{E348}$(OD2), Thr$^{E351}$(OG1) | Tyr$^{L94}$(OH), Tyr$^{L96}$(OH) |
| Thr$^{E351}$(OG1) | Tyr$^{L94}$(OH), Tyr$^{L96}$(OH) | Thr$^{E353}$(O) | Tyr$^{L94}$(OH) |
| Thr$^{E353}$(O) | Tyr$^{L94}$(OH) | Pro$^{E354}$(O) | Tyr$^{L92}$(O) |
| Pro$^{E354}$(O) | Tyr$^{L92}$(O) | Val$^{E355}$(O) | Tyr$^{L30A}$(OH) |
| Val$^{E355}$(O) | Tyr$^{L30A}$(OH) | Asp$^{E384}$(O) | Ser$^{H56}$(OG) |
| Tyr$^{E386}$(OH) | AsnH31(O) | | |

Hydrogen bonds summary

| | CDR-H1 26-32 | CDR-H2 52-56 | CDR-H3 95-102 | FRM-H | Total $V_H$ | CDR-L1 24-34 | CDR-L2 50-56 | CDR-L3 89-97 | FRM-L | Total $V_L$ |
|---|---|---|---|---|---|---|---|---|---|---|
| ZV-2  | 5 + 3 | 0 + 0 | 4 + 3 | 1 + 0 | 16 | 1 + 1 | 0 + 1 | 0 + 0 | 0 + 1 | 4 |
| ZV-48 | 0 + 1 | 1 + 0 | 3 + 0 | 1 + 2 | 8  | 5 + 3 | 0 + 0 | 3 + 4 | 0     | 15 |
| ZV-64 | 0 + 0 | 0 + 1 | 1 + 1 | 1 + 1 | 5  | 4 + 2 | 0 + 0 | 3 + 4 | 0     | 13 |
| ZV-67 | 2 + 0 | 3 + 2 | 4 + 1 | 1 + 0 | 13 | 0 + 1 | 2 + 2 | 1 + 1 | 1 + 2 | 10 |

Summary of hydrogen bonding across the interface in different mAbs/DIII complexes. The amino acids are labeled (in superscript) to indicate their specific positions in the heavy chain (H), light chain (L) or DIII (E) sequences. Hydrogen boding interactions were assessed using HBPLUS (McDonald, 1994).

TABLE 5

MAb/DIII contacts and buried surface area summary.

| | Van der Waals contacts | Hydrogen bonds | Buried Surface Area (Å²) at the mAbs/DIII Interface | | | Buried Surface Area (Å²) at the DIII/mAbs | | |
|---|---|---|---|---|---|---|---|---|
| | $V_H + V_L$ Total | $V_H + V_L$ Total | $V_H$ | $V_L$ | $V_H + V_L$ Total | Interface DIII Total | DIII surface lost (%) | Sc |
| ZV-2  | 124 | 20 | 800 | 234 | 943 | 876 | 14.3 | 0.676 |
| ZV-48 | 111 | 23 | 313 | 542 | 767 | 875 | 14.6 | 0.689 |
| ZV-64 |  89 | 18 | 306 | 522 | 750 | 829 | 14.1 | 0.708 |
| ZV-67 | 142 | 23 | 580 | 410 | 866 | 882 | 13.6 | 0.703 |

For each antibody, the total number of van der Waals contacts and direct and water-mediated hydrogen bonds are listed (as from Table 3 and Table 4), as is the amount of surface area buried when bound to DIII. The surface area lost by either antibody chain alone ($V_H$ or $V_L$) is given separately for comparison. The total area buried by both antibody chains due to interaction with DIII is also given ($V_H$ or $V_L$ Total). The amount of surface area lost by DIII due to interaction with antibody is given (DIII Total). The same value is given as a percent of the entire DIII surface area. All area values were calculated from the structural models using the program areaimol (Lee, 1971). The shape complementarity (Sc) at each mAb/DIII interface was calculated from the structural models using the program SC (Lawrence, 1993). Interfaces that mesh precisely have an Sc value of 1.

REFERENCES FOR THE EXAMPLES

1. Adams, P. D., Afonine, P. V., Bunkoczi, G., Chen, V. B., Davis, I. W., Echols, N., Headd, J. J., Hung, L. W., Kapral, G. J., Grosse-Kunstleve, R. W., et al. (2010). PHENIX: a comprehensive Python-based system for macromolecular structure solution. Acta Crystallogr D Biol Crystallogr 66, 213221.
2. Austin, S. K., Dowd, K. A., Shrestha, B., Nelson, C. A., Edeling, M. A., Johnson, S., Pierson, T. C., Diamond, M. S., and Fremont, D. H. (2012). Structural basis of differential neutralization of DENV-1 genotypes by an antibody that recognizes a cryptic epitope. PLoS Pathog 8, e1002930.
3. Balsitis, S. J., Williams, K. L., Lachica, R., Flores, D., Kyle, J. L., Mehlhop, E., Johnson, S., Diamond, M. S., Beatty, P. R., and Harris, E. (2010). Lethal antibody enhancement of dengue disease in mice is prevented by Fc modification. PLoS Pathog, e1000790.
4. Barba-Spaeth, G., Dejnirattisai, W., Rouvinski, A., Vaney, M. C., Medits, I., Sharma, A., Simon-Loriere, E., Sakuntabhai, A., Cao-Lormeau, V. M., Haouz, A., et al. (2016). Structural basis of potent Zika-dengue virus antibody cross-neutralization. Nature.
5. Baronti, C., Piorkowski, G., Charrel, R. N., Boubis, L., Leparc-Goffart, I., and de Lamballerie, X. (2014). Complete coding sequence of zika virus from a French polynesia outbreak in 2013. Genome announcements 2.
6. Beasley, D. W., and Barrett, A. D. (2002). Identification of neutralizing epitopes within structural domain III of the West Nile virus envelope protein. J Virol 76, 13097-13100.
7. Belmusto-Worn, V. E., Sanchez, J. L., McCarthy, K., Nichols, R., Bautista, C. T., Magill, A. J., Pastor-Cauna, G., Echevarria, C., Laguna-Torres, V. A., Samame, B. K., et al. (2005). Randomized, double-blind, phase III, pivotal field trial of the comparative immunogenicity, safety, and tolerability of two yellow fever 17D vaccines (Arilvax and YF-VAX) in healthy infants and children in Peru. Am J Trop Med Hyg 72, 189-197.
8. Beltramello, M., Williams, K. L., Simmons, C. P., Macagno, A., Simonelli, L., Quyen, N. T., Sukupolvi-Petty, S., Navarro-Sanchez, E., Young, P. R., de Silva, A. M., et al. (2010). The human immune response to Dengue virus is dominated by highly cross-reactive antibodies endowed with neutralizing and enhancing activity. Cell Host Microbe 8, 271-283.
9. Block, O. K., Rodrigo, W. W., Quinn, M., Jin, X., Rose, R. C., and Schlesinger, J. J. (2010). A tetravalent recombinant dengue domain III protein vaccine stimulates neutralizing and enhancing antibodies in mice. Vaccine 28, 8085-8094.
10. Brasil, P., Pereira, J. P., Jr., Raja Gabaglia, C., Damasceno, L., Wakimoto, M., Ribeiro Nogueira, R. M., Carvalho de Sequeira, P., Machado Siqueira, A., Abreu de Carvalho, L. M., Cotrim da Cunha, D., et al. (2016). Zika Virus Infection in Pregnant Women in Rio de Janeiro—Preliminary Report. N Engl J Med.
11. Brien, J. D., Austin, S. K., Sukupolvi-Petty, S., O'Brien, K. M., Johnson, S., Fremont, D. H., and Diamond, M. S. (2010). Genotype Specific Neutralization and Protection by Antibodies against Dengue Virus Type 3. J Virol 84, 10630-10643.
12. Brien, J. D., Lazear, H. M., and Diamond, M. S. (2013). Propagation, quantification, detection, and storage of West Nile virus. Curr Protoc Microbiol 31, 15D 13 11-15D 13 18.
13. Carteaux, G., Maquart, M., Bedet, A., Contou, D., Brugieres, P., Fourati, S., Cleret de Langavant, L., de Broucker, T., Brun-Buisson, C., Leparc-Goffart, I., et al. (2016). Zika Virus Associated with Meningoencephalitis. N Engl J Med 374, 1595-1596.
14. Cockburn, J. J., Navarro Sanchez, M. E., Fretes, N., Urvoas, A., Staropoli, I., Kikuti, C. M., Coffey, L. L., Arenzana Seisdedos, F., Bedouelle, H., and Rey, F. A. (2012). Mechanism of dengue virus broad cross-neutralization by a monoclonal antibody. Structure 20, 303-314.
15. Correia, B. E., Bates, J. T., Loomis, R. J., Baneyx, G., Carrico, C., Jardine, J. G., Rupert, P., Correnti, C., Kalyuzhniy, O., Vittal, V., et al. (2014). Proof of principle for epitope-focused vaccine design. Nature 507, 201-206.
16. Cugola, F. R., Fernandes, I. R., Russo, F. B., Freitas, B. C., Dias, J. L., Guimaraes, K. P., Benazzato, C., Almeida, N., Pignatari, G. C., Romero, S., et al. (2016). The Brazilian Zika virus strain causes birth defects in experimental models. Nature 534, 267-271.
17. Dai, L., Song, J., Lu, X., Deng, Y. Q., Musyoki, A. M., Cheng, H., Zhang, Y., Yuan, Y., Song, H., Haywood, J., et al. (2016). Structures of the Zika Virus Envelope Protein and Its Complex with a Flavivirus Broadly Protective Antibody. Cell Host Microbe 19, 696-704.
18. de Alwis, R., Smith, S. A., Olivarez, N. P., Messer, W. B., Huynh, J. P., Wahala, W. M., White, L. J., Diamond, M. S., Baric, R. S., Crowe, J. E., Jr., et al. (2012).

Identification of human neutralizing antibodies that bind to complex epitopes on dengue virions. Proc Natl Acad Sci USA 109, 74397444.
19. Dick, G. W. (1952). Zika virus. II. Pathogenicity and physical properties. Trans R Soc Trop Med Hyg 46, 521-534.
20. Dick, G. W., Kitchen, S. F., and Haddow, A. J. (1952). Zika virus. I. Isolations and serological specificity. Trans R Soc Trop Med Hyg 46, 509-520.
21. Dowd, K. A., DeMaso, C. R., and Pierson, T. C. (2015). Genotypic Differences in Dengue Virus Neutralization Are Explained by a Single Amino Acid Mutation That Modulates Virus Breathing. MBio 6, e01559-01515.
22. Dowd, K. A., Jost, C. A., Durbin, A. P., Whitehead, S. S., and Pierson, T. C. (2011). A dynamic landscape for antibody binding modulates antibody-mediated neutralization of West Nile virus. PLoS Pathog 7, e1002111.
23. Edeling, M. A., Austin, S. K., Shrestha, B., Dowd, K. A., Mukherjee, S., Nelson, C. A., Johnson, S., Mabila, M. N., Christian, E. A., Rucker, J., et al. (2014). Potent dengue virus neutralization by a therapeutic antibody with low monovalent affinity requires bivalent engagement. PLoS Pathog 10, e1004072.
24. Emsley, P., Lohkamp, B., Scott, W. G., and Cowtan, K. (2010). Features and development of Coot. Acta Crystallogr D Biol Crystallogr 66, 486-501.
25. Evans, P. R., and Murshudov, G. N. (2013). How good are my data and what is the resolution? Acta Crystallogr D Biol Crystallogr 69, 1204-1214.
26. Fibriansah, G., Tan, J. L., Smith, S. A., de Alwis, A. R., Ng, T. S., Kostyuchenko, V. A., Ibarra, K. D., Wang, J., Harris, E., de Silva, A., et al. (2014). A potent anti-dengue human antibody preferentially recognizes the conformation of E protein monomers assembled on the virus surface. EMBO Mol Med 6, 358-371.
27. Goncalvez, A. P., Chien, C. H., Tubthong, K., Gorshkova, I., Roll, C., Donau, O., Schuck, P., Yoksan, S., Wang, S. D., Purcell, R. H., et al. (2008). Humanized monoclonal antibodies derived from chimpanzee Fabs protect against Japanese encephalitis virus in vitro and in vivo. J Virol 82, 7009-7021.
28. Goncalvez, A. P., Engle, R. E., St Claire, M., Purcell, R. H., and Lai, C. J. (2007). Monoclonal antibody-mediated enhancement of dengue virus infection in vitro and in vivo and strategies for prevention. Proc Natl Acad Sci USA 104, 9422-9427.
29. Grant, A., Ponia, S. S., Tripathi, S., Balasubramaniam, V., Miorin, L., Sourisseau, M., Schwarz, M. C., Sanchez-Seco, M. P., Evans, M. J., Best, S. M., et al. (2016). Zika Virus Targets Human STAT2 to Inhibit Type I Interferon Signaling. Cell Host Microbe 19, 882-890.
30. Gromowski, G. D., and Barrett, A. D. (2007). Characterization of an antigenic site that contains a dominant, type-specific neutralization determinant on the envelope protein domain III (ED3) of dengue 2 virus. Virology 366, 349-360.
31. Hanna, S. L., Pierson, T. C., Sanchez, M. D., Ahmed, A. A., Murtadha, M. M., and Doms, R. W. (2005). N-linked glycosylation of west nile virus envelope proteins influences particle assembly and infectivity. J Virol 79, 13262-13274.
32. Heinz, F. X., Holzmann, H., Essl, A., and Kundi, M. (2007). Field effectiveness of vaccination against tick-borne encephalitis. Vaccine 25, 7559-7567.
33. Heinz, F. X., and Stiasny, K. (2012). Flaviviruses and their antigenic structure. J Clin Virol 55, 289295.
34. Jarmer, J., Zlatkovic, J., Tsouchnikas, G., Vratskikh, O., Strauss, J., Aberle, J. H., Chmelik, V., Kundi, M., Stiasny, K., and Heinz, F. X. (2014). Variation of the specificity of the human antibody responses after tick-borne encephalitis virus infection and vaccination. J Virol 88, 13845-13857. Kabsch, W. (2010). XDS. Acta Crystallogr D Biol Crystallogr 66, 125-132.
35. Kaufmann, B., Nybakken, G., Chipman, P. R., Zhang, W., Fremont, D. H., Diamond, M. S., Kuhn, R. J., and Rossmann, M. G. (2006). West Nile virus in complex with a neutralizing monoclonal antibody. Proc Natl Acad Sci USA 103, 12400-12404.
36. Kaufmann, B., Vogt, M. R., Goudsmit, J., Holdaway, H. A., Aksyuk, A. A., Chipman, P. R., Kuhn, R. J., Diamond, M. S., and Rossmann, M. G. (2010). Neutralization of West Nile virus by cross-linking of its surface proteins with Fab fragments of the human monoclonal antibody CR4354. Proc Natl Acad Sci USA 107, 18950-18955.
37. Kim, J., Mohanty, S., Ganesan, L. P., Hua, K., Jarjoura, D., Hayton, W. L., Robinson, J. M., and Anderson, C. L. (2009). FcRn in the yolk sac endoderm of mouse is required for IgG transport to fetus. J Immunol 182, 2583-2589.
38. Kostyuchenko, V. A., Lim, E. X., Zhang, S., Fibriansah, G., Ng, T. S., Ooi, J. S., Shi, J., and Lok, S. M. (2016). Structure of the thermally stable Zika virus. Nature 533, 425-428.
39. Kuhn, R. J., Zhang, W., Rossmann, M. G., Pletnev, S. V., Corver, J., Lenches, E., Jones, C. T., Mukhopadhyay, S., Chipman, P. R., Strauss, E. G., et al. (2002). Structure of dengue virus: implications for flavivirus organization, maturation, and fusion. Cell 108, 717-725.
40. Lanciotti, R. S., Kosoy, O. L., Laven, J. J., Velez, J. O., Lambert, A. J., Johnson, A. J., Stanfield, S. M., and Duffy, M. R. (2008). Genetic and serologic properties of Zika virus associated with an epidemic, Yap State, Micronesia, 2007. Emerg Infect Dis 14, 1232-1239.
41. Larocca, R. A., Abbink, P., Peron, J. P., Zanotto, P. M., Iampietro, M. J., Badamchi-Zadeh, A., Boyd, M., Ng'ang'a, D., Kirilova, M., Nityanandam, R., et al. (2016). Vaccine protection against Zika virus from Brazil. Nature.
42. Lawrence, M. C., and Colman, P. M. (1993). Shape complementarity at protein/protein interfaces. J Mol Biol 234, 946-950.
43. Lazear, H. M., and Diamond, M. S. (2016). Zika Virus: New Clinical Syndromes and Its Emergence in the Western Hemisphere. J Virol 90, 4864-4875.
44. Lazear, H. M., Govero, J., Smith, A. M., Platt, D. J., Fernandez, E., Miner, J. J., and Diamond, M. S. (2016). A Mouse Model of Zika Virus Pathogenesis. Cell Host Microbe.
45. Lee, B., and Richards, F. M. (1971). The interpretation of protein structures: estimation of static accessibility. J Mol Biol 55, 379-400.
46. Li, C., Xu, D., Ye, Q., Hong, S., Jiang, Y., Liu, X., Zhang, N., Shi, L., Qin, C. F., and Xu, Z. (2016). Zika Virus Disrupts Neural Progenitor Development and Leads to Microcephaly in Mice. Cell stem cell.
47. Lindenbach, B. D., Murray, C. L., Thiel, H. J., and Rice, C. M. (2013). Flaviviviridae. In Fields Virology, D. M. Knipe, and P. M. Howley, eds. (Philadelphia: Lippincott Williams & Wilkins), pp. 712-746.
48. Lok, S. M., Kostyuchenko, V., Nybakken, G. E., Holdaway, H. A., Battisti, A. J., Sukupolvi-Petty, S., Sedlak, D., Fremont, D. H., Chipman, P. R., Roehrig, J. T., et al. (2008). Binding of a neutralizing antibody to dengue virus 49. Lucchese, G., and Kanduc, D. (2016). Zika virus and autoimmunity: From microcephaly to Guillain-Barre syndrome, and beyond. Autoimmunity reviews.
50. Mancia, F., Patel, S. D., Rajala, M. W., Scherer, P. E., Nemes, A., Schieren, I., Hendrickson, W. A., and Shapiro, L. (2004). Optimization of protein production in mammalian cells with a coexpressed fluorescent marker. Structure 12, 1355-1360.
51. Martina, B. E., Koraka, P., van den Doel, P., van Amerongen, G., Rimmelzwaan, G. F., and Osterhaus, A. D. (2008). Immunization with West Nile virus envelope domain III protects mice against lethal infection with homologous and heterologous virus. Vaccine 26, 153-157.
52. McCoy, A. J., Grosse-Kunstleve, R. W., Adams, P. D., Winn, M. D., Storoni, L. C., and Read, R. J. (2007). Phaser crystallographic software. Journal of applied crystallography 40, 658-674.
53. McDonald, I. K., and Thornton, J. M. (1994). Satisfying hydrogen bonding potential in proteins. J Mol Biol 238, 777-793.
54. Midgley, C. M., Flanagan, A., Tran, H. B., Dejnirattisai, W., Chawansuntati, K., Jumnainsong, A., Wongwiwat, W., Duangchinda, T., Mongkolsapaya, J., Grimes, J. M., et al. (2012). Structural analysis of a dengue cross-reactive antibody complexed with envelope domain III reveals the molecular basis of cross-reactivity. J Immunol 188, 4971-4979.
55. Miner, J. J., Cao, B., Govero, J., Smith, A. M., Fernandez, E., Cabrera, O. H., Garber, C., Noll, M., Klein, R. S., Noguchi, K. K., et al. (2016). Zika Virus Infection during Pregnancy in Mice Causes Placental Damage and Fetal Demise. Cell 165, 1081-1091.
56. Nelson, S., Jost, C. A., Xu, Q., Ess, J., Martin, J. E., Oliphant, T., Whitehead, S. S., Durbin, A. P., Graham, B. S., Diamond, M. S., et al. (2008). Maturation of West Nile virus modulates sensitivity to antibody-mediated neutralization. PLoS Pathog 4, e1000060.
57. Nybakken, G., Oliphant, T., Johnson, S., Burke, S., Diamond, M. S., and Fremont, D. H. (2005). Structural basis for neutralization of a therapeutic antibody against West Nile virus. Nature 437, 764-769.
58. Obara, C. J., Dowd, K. A., Ledgerwood, J. E., and Pierson, T. C. (2013). Impact of viral attachment factor expression on antibody-mediated neutralization of flaviviruses. Virology 437, 20-27.
59. Oehler, E., Watrin, L., Larre, P., Leparc-Goffart, I., Lastere, S., Valour, F., Baudouin, L., Mallet, H., Musso, D., and Ghawche, F. (2014). Zika virus infection complicated by Guillain-Barre syndrome-case report, French Polynesia, December 2013. Euro Surveill 19.
60. Oliphant, T., Engle, M., Nybakken, G., Doane, C., Johnson, S., Huang, L., Gorlatov, S., Mehlhop, E., Marri, A., Chung, K. M., et al. (2005). Development of a humanized monoclonal antibody with therapeutic potential against West Nile virus. Nature Medicine 11, 522-530.
61. Oliphant, T., Nybakken, G. E., Austin, S. K., Xu, Q., Bramson, J., Loeb, M., Throsby, M., Fremont, D. H., Pierson, T. C., and Diamond, M. S. (2007). The Induction of Epitope-Specific Neutralizing Antibodies against West Nile virus. J Virol 81, 11828-11839.
62. Oliphant, T., Nybakken, G. E., Engle, M., Xu, Q., Nelson, C. A., Sukupolvi-Petty, S., Marri, A., Lachmi, B. E., Olshevsky, U., Fremont, D. H., et al. (2006). Antibody recognition and neutralization determinants on domains I and II of West Nile Virus envelope protein. J Virol 80, 12149-12159.
63. Pal, P., Dowd, K. A., Brien, J. D., Edeling, M. A., Gorlatov, S., Johnson, S., Lee, I., Akahata, W., Nabel, G. J., Richter, M. K. S., et al. (2013). Development of a highly protective combination monoclonal antibody therapy against Chikungunya virus PLoS Pathog 9, e1003312.
64. Pentsuk, N., and van der Laan, J. W. (2009). An interspecies comparison of placental antibody transfer: new insights into developmental toxicity testing of monoclonal antibodies. Birth defects research Part B, Developmental and reproductive toxicology 86, 328-344.
65. Pierson, T. C., and Diamond, M. S. (2008). Molecular mechanisms of antibody-mediated neutralization of flavivirus infection. Exp Rev Mol Med 10, e12.
66. Pierson, T. C., and Diamond, M. S. (2013). Flaviviruses. In Fields Virology, D. M. Knipe, and P. M. Howley, eds. (Lippincott Williams & Wilkins), pp. 747-794.
67. Pierson, T. C., and Diamond, M. S. (2015). A game of numbers: the stoichiometry of antibody-mediated neutralization of flavivirus infection. Progress in molecular biology and translational science 129, 141-166.
68. Pierson, T. C., Fremont, D. H., Kuhn, R. J., and Diamond, M. S. (2008). Structural insights into the mechanisms of antibody-mediated neutralization of flavivirus infection: implications for vaccine development. Cell Host Microbe 4, 229-238.
69. Pierson, T. C., Xu, Q., Nelson, S., Oliphant, T., Nybakken, G. E., Fremont, D. H., and Diamond, M. S. (2007). The stoichiometry of antibody-mediated neutralization and enhancement of West Nile virus infection. Cell Host and Microbe 1, 135-145.
70. Rossi, S. L., Tesh, R. B., Azar, S. R., Muruato, A. E., Hanley, K. A., Auguste, A. J., Langsjoen, R. M., Paessler, S., Vasilakis, N., and Weaver, S. C. (2016). Characterization of a Novel Murine Model to Study Zika Virus. Am J Trop Med Hyg.
71. Rouvinski, A., Guardado-Calvo, P., Barba-Spaeth, G., Duquerroy, S., Vaney, M. C., Kikuti, C. M., Navarro Sanchez, M. E., Dejnirattisai, W., Wongwiwat, W., Haouz, A., et al. (2015). Recognition determinants of broadly neutralizing human antibodies against dengue viruses. Nature 520, 109113.
72. Sanchez, M. D., Pierson, T. C., McAllister, D., Hanna, S. L., Puffer, B. A., Valentine, L. E., Murtadha, M. M., Hoxie, J. A., and Doms, R. W. (2005). Characterization of neutralizing antibodies to West Nile virus. Virology 336, 70-82.
73. Schneeweiss, A., Chabierski, S., Salomo, M., Delaroque, N., Al-Robaiy, S., Grunwald, T., Burki, K., Liebert, U. G., and Ulbert, S. (2011). A DNA vaccine encoding the E protein of West Nile virus is protective and can be boosted by recombinant domain DIII. Vaccine 29, 6352-6357.
74. Sheehan, K. C., Lai, K. S., Dunn, G. P., Bruce, A. T., Diamond, M. S., Heutel, J. D., Dungo-Arthur, C., Carrero, J. A., White, J. M., Hertzog, P. J., et al. (2006). Blocking monoclonal antibodies specific for mouse IFN-alpha/beta receptor subunit 1 (IFNAR-1) from mice immunized by in vivo hydrodynamic transfection. J Interferon Cytokine Res 26, 804-819.
75. Shrestha, B., Brien, J. D., Sukupolvi-Petty, S., Austin, S. K., Edeling, M. A., Kim, T., O'Brien, K. M., Nelson, C. A., Johnson, S., Fremont, D. H., et al. (2010). The Development of Therapeutic Antibodies that Neutralize 76. Sirohi, D., Chen, Z., Sun, L., Klose, T., Pierson, T. C., Rossmann, M. G., and Kuhn, R. J. (2016). The 3.8 Å resolution cryo-EM structure of Zika virus. Science.
77. Smith, S. A., de Alwis, A. R., Kose, N., Harris, E., Ibarra, K. D., Kahle, K. M., Pfaff, J. M., Xiang, X., Doranz, B. J., de Silva, A. M., et al. (2013). The potent and broadly neutralizing human dengue virus-specific monoclonal antibody 1C19 reveals a unique cross-reactive epitope on the be loop of domain II of the envelope protein. MBio 4, e00873-00813.
78. Sukupolvi-Petty, S., Austin, S. K., Engle, M., Brien, J. D., Dowd, K. A., Williams, K. L., Johnson, S., Rico-Hesse, R., Harris, E., Pierson, T. C., et al. (2010). Structure and Function Analysis of Therapeutic Monoclonal Antibodies against Dengue Virus Type 2. J Virol 84, 9227-9239.
79. Sukupolvi-Petty, S., Austin, S. K., Purtha, W. E., Oliphant, T., Nybakken, G., Schlesinger, J. J., Roehrig, J. T., Gromowski, G. D., Barrett, A. D., Fremont, D. H., et al. (2007). Type- and Sub-Complex-Specific Neutralizing Antibodies Against Domain III of Dengue Virus Type-2 Envelope Protein Recognize Adjacent Epitopes. J Virol 81, 12816-12826.
80. Sukupolvi-Petty, S., Brien, J. D., Austin, S. K., Shrestha, B., Swayne, S., Kahle, K., Doranz, B. J., Johnson, S., Pierson, T. C., Fremont, D. H., et al. (2013). Functional analysis of antibodies against Dengue virus type 4 reveals strain-dependent epitope exposure that impacts neutralization and protection. J Virol 87, 8826-8842.
81. Vogt, M. R., Dowd, K. A., Engle, M., Tesh, R. B., Johnson, S., Pierson, T. C., and Diamond, M. S. (2011). Poorly neutralizing cross-reactive antibodies against the fusion loop of West Nile virus envelope protein protect in vivo via Fc-{gamma} receptor and complement-dependent effector mechanisms. J Virol 22, 11567-11580.
82. Wahala, W. M., Donaldson, E. F., de Alwis, R., Accavitti-Loper, M. A., Baric, R. S., and de Silva, A. M. (2010). Natural strain variation and antibody neutralization of Dengue serotype 3 viruses. PLoS Pathog 6, e1000821.
83. Williams, K. L., Sukupolvi-Petty, S., Beltramello, M., Johnson, S., Sallusto, F., Lanzavecchia, A., Diamond, M. S., and Harris, E. (2013). Therapeutic Efficacy of Antibodies Lacking FcgammaR against Lethal Dengue Virus Infection Is Due to Neutralizing Potency and Blocking of Enhancing Antibodies. PLoS Pathog 9, e1003157.
84. Wu, K. P., Wu, C. W., Tsao, Y. P., Kuo, T. W., Lou, Y. C., Lin, C. W., Wu, S. C., and Cheng, J. W. (2003). Structural basis of a Flavivirus recognized by its neutralizing antibody: Solution structure of the domain III of the Japanese Encephalitis virus envelope protein. J Biol Chem 278, 4600746013.
85. Zellweger, R. M., Prestwood, T. R., and Shresta, S. (2010). Enhanced infection of liver sinusoidal endothelial cells in a mouse model of antibody-induced severe dengue disease. Cell Host Microbe 7, 128-139.
86. Zhang, X., Ge, P., Yu, X., Brannan, J. M., Bi, G., Zhang, Q., Schein, S., and Zhou, Z. H. (2013). Cryo-EM structure of the mature dengue virus at 3.5-A resolution. Nat Struct Mol Biol 20, 105110.
87. Zlatkovic, J., Tsouchnikas, G., Jarmer, J., Koessl, C., Stiasny, K., and Heinz, F. X. (2013). Aluminum hydroxide influences not only the extent but also the fine specificity and functional activity of antibody responses to tick-borne encephalitis virus in mice. J Virol 87, 12187-12195.
88. Al-Lazikani, B., Lesk, A. M., and Chothia, C. (1997). Standard conformations for the canonical structures of immunoglobulins. J Mol Biol 273, 927-948.

What is claimed is:

1. An isolated anti-Zika antigen binding protein comprising a light chain variable region amino acid sequence of SEQ ID NO: 8 and comprising a heavy chain variable region amino acid sequence of SEQ ID NO: 7.

2. The isolated antigen binding protein of claim 1, wherein the antigen binding protein further comprises a human constant domain, wherein the human constant domain is selected from an IgG, IgA, IgM, or IgE constant domain.

3. The isolated antigen binding protein of claim 1, wherein the antigen binding protein is a monoclonal antibody or an antibody fragment.

4. An immunoassay comprising at least one isolated antigen binding protein of claim 2.

5. The immunoassay of claim 4, wherein the immunoassay is a competitive immunoassay.

6. A method of treating a Zika virus infection in a subject, the method comprising administering to the subject an effective amount of an isolated antigen binding protein, wherein the antigen binding protein comprises a light chain variable region amino acid sequence of SEQ ID NO: 8 and comprises a heavy chain variable region amino acid sequence of SEQ ID NO:7.

7. A method of providing clinical protection with reduced viremia against a Zika virus infection in a subject, the method comprising administering to the subject an effective amount of an isolated antigen binding protein, wherein the antigen binding protein comprises a light chain variable region amino acid sequence of SEQ ID NO: 8 and comprises a the heavy chain variable region amino acid sequence of SEQ ID NO:7.

8. The method of claim 6, wherein the subject is pregnant or plans to become pregnant.

* * * * *

SEQUENCE LISTING

```
<160> NUMBER OF SEQ ID NOS: 56

<210> SEQ ID NO 1
<211> LENGTH: 120
<212> TYPE: PRT
<213> ORGANISM: Artificial Sequence
<220> FEATURE:
<223> OTHER INFORMATION: SYNTHESIZED

<400> SEQUENCE: 1

Gln Val Gln Leu Gln Glu Ser Gly Ala Glu Leu Met Lys Pro Gly Ala
1               5                   10                  15

Ser Val Lys Leu Ser Cys Lys Thr Ser Gly Tyr Thr Phe Ile Gly Tyr
            20                  25                  30

Trp Ile Glu Trp Leu Lys Gln Arg Pro Gly His Gly Leu Glu Trp Val
        35                  40                  45

Gly Glu Ile Phe Pro Gly Ser Gly Arg Thr Lys Tyr Asn Glu Lys Phe
    50                  55                  60

Lys Gly Arg Ala Thr Phe Thr Ala Asp Thr Ser Ser Asn Met Ala Tyr
65                  70                  75                  80

Met Gln Leu Ser Ser Leu Thr Thr Glu Asp Ser Ala Ile Tyr Tyr Cys
                85                  90                  95

Ala Arg Tyr Tyr Tyr Gly Ser Tyr Tyr Ala Leu Asp Tyr Trp Gly Gln
            100                 105                 110

Gly Thr Ser Val Thr Val Ser Ser
        115                 120
```

```
<210> SEQ ID NO 2
<211> LENGTH: 113
<212> TYPE: PRT
<213> ORGANISM: Artificial Sequence
<220> FEATURE:
<223> OTHER INFORMATION: SYNTHESIZED

<400> SEQUENCE: 2
```

Asp Ile Val Met Thr Gln Ser Pro Ser Ser Leu Ser Val Ser Ala Gly
1               5                   10                  15

Glu Lys Val Thr Leu Ser Cys Lys Ser Ser Gln Ser Leu Leu His Ser
            20                  25                  30

Gly Asn Gln Lys Asn Tyr Leu Ala Trp Tyr Gln Gln Lys Pro Gly Gln
        35                  40                  45

Ala Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Ser Tyr Pro Leu Thr Phe Gly Ala Gly Thr Lys Leu Glu Leu
            100                 105                 110

Lys

```
<210> SEQ ID NO 3
<211> LENGTH: 116
<212> TYPE: PRT
<213> ORGANISM: Artificial Sequence
<220> FEATURE:
<223> OTHER INFORMATION: SYNTHESIZED

<400> SEQUENCE: 3
```

Gln Val Gln Leu Gln Gln Pro Gly Ala Glu Leu Leu Lys Pro Gly Ala
1               5                   10                  15

Ser Val Lys Leu Ser Cys Lys Ala Ser Gly Tyr Ser Phe Ser Asn Tyr
            20                  25                  30

Trp Met His Trp Val Lys Gln Arg Pro Gly Gln Gly Pro Glu Trp Ile
        35                  40                  45

Gly Met Ile His Pro Asn Ser Gly Asn Thr Lys Tyr Asn Glu Lys Phe
    50                  55                  60

Lys Asn Lys Ala Thr Leu Thr Val Asp Lys Ser Ser Ser Met Val Tyr
65                  70                  75                  80

Met Gln Leu Ser Ser Leu Thr Ser Glu Asp Ser Ala Val Phe Tyr Cys
                85                  90                  95

Ala Arg Leu Gly Asn Asp Met Asp Tyr Trp Gly Gln Gly Thr Ser Val
            100                 105                 110

Thr Val Ser Ser
        115

```
<210> SEQ ID NO 4
<211> LENGTH: 113
<212> TYPE: PRT
<213> ORGANISM: Artificial Sequence
<220> FEATURE:
<223> OTHER INFORMATION: SYNTHESIZED

<400> SEQUENCE: 4
```

Asp Ile Val Met Ser Gln Ser Pro Ser Ser Leu Ala Val Ser Val Gly

```
                1               5                   10                  15
            Glu Lys Ile Thr Met Ser Cys Lys Ser Ser Gln Ser Leu Leu Tyr Ser
                            20                  25                  30

Asn Asn Glu Lys Asn Tyr Leu Ala Trp Tyr Gln Gln Lys Pro Gly Gln
                            35                  40                  45

Ser Pro Lys Leu Leu Ile Tyr Trp Ala Ser Ala Arg Asp Ser Gly Val
                50                  55                  60

Pro Asp Arg Phe Thr Gly Ser Gly Ser Gly Thr Asp Phe Thr Leu Thr
            65                  70                  75                  80

Ile Ser Ser Val Lys Ala Glu Asp Leu Ala Val Phe Tyr Cys Gln Gln
                            85                  90                  95

Tyr Tyr Ser Tyr Pro Tyr Thr Phe Gly Gly Gly Thr Lys Leu Glu Ile
                            100                 105                 110

Lys

<210> SEQ ID NO 5
<211> LENGTH: 119
<212> TYPE: PRT
<213> ORGANISM: Artificial Sequence
<220> FEATURE:
<223> OTHER INFORMATION: SYNTHESIZED

<400> SEQUENCE: 5

Gln Val Gln Leu Gln Gln Pro Gly Ala Glu Leu Val Lys Pro Gly Ala
            1               5                   10                  15

Ser Val Lys Leu Ser Cys Lys Ala Ser Gly Tyr Thr Phe Thr Ser Ser
                            20                  25                  30

Trp Met His Trp Val Lys Gln Arg Pro Gly Gln Gly Leu Glu Trp Ile
                            35                  40                  45

Gly Met Ile His Pro Asn Ser Gly Ser Thr Asn Tyr Asn Glu Lys Phe
                50                  55                  60

Lys Asn Lys Ala Thr Leu Thr Val Asp Lys Ser Ser Ser Thr Ala Tyr
            65                  70                  75                  80

Met Gln Leu Ser Ser Leu Thr Ser Glu Asp Ser Ala Val Tyr Tyr Cys
                            85                  90                  95

Ala Arg Tyr Tyr Tyr Asp Tyr Asp Gly Met Asp Tyr Trp Gly Gln Gly
                            100                 105                 110

Thr Ser Val Thr Val Ser Ser
                            115

<210> SEQ ID NO 6
<211> LENGTH: 113
<212> TYPE: PRT
<213> ORGANISM: Artificial Sequence
<220> FEATURE:
<223> OTHER INFORMATION: SYNTHESIZED

<400> SEQUENCE: 6

Asp Ile Val Met Ser Gln Ser Pro Ser Ser Leu Ala Val Ser Val Gly
            1               5                   10                  15

Glu Lys Val Thr Met Ser Cys Lys Ser Ser Gln Ser Leu Leu Tyr Ser
                            20                  25                  30

Ser Asn Gln Lys Asn Tyr Leu Ala Trp Tyr Gln Gln Lys Pro Gly Gln
                            35                  40                  45

Ser Pro Lys Leu Leu Ile Tyr Trp Ala Ser Thr Arg Glu Ser Gly Val
                50                  55                  60

Pro Asp Arg Phe Thr Gly Ser Gly Ser Gly Thr Asp Phe Thr Leu Thr
```

```
                65                  70                  75                  80
Ile Ser Ser Val Lys Ala Glu Asp Leu Ala Val Tyr Tyr Cys Gln Gln
                    85                  90                  95

Tyr Tyr Thr Tyr Pro Tyr Thr Phe Gly Gly Gly Thr Lys Leu Glu Ile
                100                 105                 110

Asn

<210> SEQ ID NO 7
<211> LENGTH: 116
<212> TYPE: PRT
<213> ORGANISM: Artificial Sequence
<220> FEATURE:
<223> OTHER INFORMATION: SYNTHESIZED

<400> SEQUENCE: 7

Gln Ala Gln Leu Gln Gln Ser Gly Thr Gly Leu Ala Arg Pro Gly Ala
1               5                   10                  15

Ser Val Lys Leu Ser Cys Lys Ala Ser Gly Tyr Thr Phe Thr Ser Tyr
                20                  25                  30

Gly Ile Ser Trp Val Thr Gln Arg Ala Gly Gln Gly Leu Glu Trp Ile
            35                  40                  45

Gly Val Ile Tyr Pro Arg Ser Gly Asn Thr Tyr Tyr Asn Glu Lys Phe
        50                  55                  60

Arg Gly Lys Ala Thr Leu Thr Ala Asp Lys Ser Ser Ser Ser Ala Tyr
65                  70                  75                  80

Met Glu Leu Arg Gly Leu Thr Ala Glu Asp Ser Ala Val Tyr Phe Cys
                85                  90                  95

Ala Arg Glu Asn Tyr Gly Ser Val Tyr Trp Gly Gln Gly Thr Thr Leu
                100                 105                 110

Thr Val Ser Ser
            115

<210> SEQ ID NO 8
<211> LENGTH: 107
<212> TYPE: PRT
<213> ORGANISM: Artificial Sequence
<220> FEATURE:
<223> OTHER INFORMATION: SYNTHESIZED

<400> SEQUENCE: 8

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ala
                20                  25                  30

Val Ala Trp Tyr Gln Gln Lys Pro Gly Gln Ser Pro Lys Leu Leu Ile
            35                  40                  45

Tyr Ser Ala Ser Asn Arg Tyr Thr Gly Val Pro Asp Arg Phe Thr Gly
        50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Phe Ser Ser Tyr Pro Tyr
                85                  90                  95

Thr Phe Gly Gly Gly Thr Lys Leu Glu Ile Lys
                100                 105

<210> SEQ ID NO 9
<211> LENGTH: 116
<212> TYPE: PRT
```

```
<213> ORGANISM: Artificial Sequence
<220> FEATURE:
<223> OTHER INFORMATION: SYNTHESIZED

<400> SEQUENCE: 9

Gln Val Gln Leu Gln Gln Ser Gly Val Gly Leu Ala Arg Pro Gly Thr
1               5                   10                  15

Ser Val Lys Leu Ser Cys Lys Ala Ser Gly Tyr Ser Phe Thr Thr Tyr
            20                  25                  30

Gly Ile Ser Trp Val Thr Gln Arg Pro Gly Gln Gly Leu Glu Trp Ile
        35                  40                  45

Gly Val Ile Tyr Pro Arg Ser Asn Asn Thr Tyr Tyr Asn Glu Arg Phe
    50                  55                  60

Arg Gly Lys Ala Thr Leu Thr Ala Asp Lys Ser Ser Ser Ser Ala Tyr
65                  70                  75                  80

Leu Glu Leu Arg Gly Leu Thr Ala Glu Asp Ser Ala Val Tyr Phe Cys
                85                  90                  95

Ala Arg Glu Asn Tyr Gly Ser Val Tyr Trp Gly Gln Gly Thr Thr Leu
            100                 105                 110

Thr Val Ser Ser
        115

<210> SEQ ID NO 10
<211> LENGTH: 107
<212> TYPE: PRT
<213> ORGANISM: Artificial Sequence
<220> FEATURE:
<223> OTHER INFORMATION: SYNTHESIZED

<400> SEQUENCE: 10

Asp Ile Val Met Thr Gln Ser Gln Lys Phe Met Ser Thr Ser Val Gly
1               5                   10                  15

Asp Arg Val Thr Ile Thr Cys Lys Ala Ser Gln Ser Val Gly Thr Ala
            20                  25                  30

Val Ala Trp Tyr His Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Thr Tyr Met Gln Ser
65                  70                  75                  80

Glu Asp Leu Ala Asp Tyr Phe Cys Gln Gln Phe Ser Asn Tyr Pro Phe
                85                  90                  95

Thr Phe Gly Gly Gly Thr Lys Leu Glu Ile Lys
            100                 105

<210> SEQ ID NO 11
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 11

Gly Tyr Thr Phe Ile Gly Tyr
1               5

<210> SEQ ID NO 12
<211> LENGTH: 7
<212> TYPE: PRT
<213> ORGANISM: Artificial Sequence
```

```
<220> FEATURE:
<223> OTHER INFORMATION: SYNTHESIZED

<400> SEQUENCE: 12

Gly Tyr Ser Phe Ser Asn Tyr
1               5

<210> SEQ ID NO 13
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 13

Gly Tyr Thr Phe Thr Ser Ser
1               5

<210> SEQ ID NO 14
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 14

Gly Tyr Thr Phe Thr Ser Tyr
1               5

<210> SEQ ID NO 15
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 15

Gly Tyr Ser Phe Thr Thr Tyr
1               5

<210> SEQ ID NO 16
<211> LENGTH: 6
<212> TYPE: PRT
<213> ORGANISM: Artificial Sequence
<220> FEATURE:
<223> OTHER INFORMATION: SYNTHESIZED

<400> SEQUENCE: 16

Phe Pro Gly Ser Gly Arg
1               5

<210> SEQ ID NO 17
<211> LENGTH: 6
<212> TYPE: PRT
<213> ORGANISM: Artificial Sequence
<220> FEATURE:
<223> OTHER INFORMATION: SYNTHESIZED

<400> SEQUENCE: 17

His Pro Asn Ser Gly Asn
1               5

<210> SEQ ID NO 18
<211> LENGTH: 6
<212> TYPE: PRT
<213> ORGANISM: Artificial Sequence
<220> FEATURE:
```

```
<223> OTHER INFORMATION: SYNTHESIZED

<400> SEQUENCE: 18

His Pro Asn Ser Gly Ser
1               5

<210> SEQ ID NO 19
<211> LENGTH: 6
<212> TYPE: PRT
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (5)..(5)
<223> OTHER INFORMATION: Xaa can be any naturally occurring amino acid

<400> SEQUENCE: 19

Tyr Pro Arg Ser Xaa Asn
1               5

<210> SEQ ID NO 20
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 20

Tyr Tyr Tyr Gly Ser Tyr Tyr Ala Leu Asp Tyr
1               5                   10

<210> SEQ ID NO 21
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 21

Leu Gly Asn Asp Met Asp Tyr
1               5

<210> SEQ ID NO 22
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 22

Tyr Tyr Tyr Asp Tyr Asp Gly Met Asp Tyr
1               5                   10

<210> SEQ ID NO 23
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 23

Glu Asn Tyr Gly Ser Val Tyr
1               5

<210> SEQ ID NO 24
<211> LENGTH: 17
```

```
<212> TYPE: PRT
<213> ORGANISM: Artificial Sequence
<220> FEATURE:
<223> OTHER INFORMATION: SYNTHESIZED

<400> SEQUENCE: 24

Lys Ser Ser Gln Ser Leu Leu His Ser Gly Asn Gln Lys Asn Tyr Leu
1               5                   10                  15

Ala

<210> SEQ ID NO 25
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 25

Lys Ser Ser Gln Ser Leu Leu Tyr Ser Asn Asn Glu Lys Asn Tyr Leu
1               5                   10                  15

Ala

<210> SEQ ID NO 26
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 26

Lys Ser Ser Gln Ser Leu Leu Tyr Ser Ser Asn Gln Lys Asn Tyr Leu
1               5                   10                  15

Ala

<210> SEQ ID NO 27
<211> LENGTH: 11
<212> TYPE: PRT
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (5)..(5)
<223> OTHER INFORMATION: Xaa can be any naturally occurring amino acid

<400> SEQUENCE: 27

Lys Ala Ser Gln Xaa Val Gly Thr Ala Val Ala
1               5                   10

<210> SEQ ID NO 28
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 28

Gly Ala Ser Thr Arg Glu Ser
1               5

<210> SEQ ID NO 29
<211> LENGTH: 7
<212> TYPE: PRT
<213> ORGANISM: Artificial Sequence
<220> FEATURE:
<223> OTHER INFORMATION: SYNTHESIZED
```

<400> SEQUENCE: 29

Trp Ala Ser Ala Arg Asp Ser
1               5

<210> SEQ ID NO 30
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 30

Trp Ala Ser Thr Arg Glu Ser
1               5

<210> SEQ ID NO 31
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 31

Ser Ala Ser Asn Arg Tyr Thr
1               5

<210> SEQ ID NO 32
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 32

Gln Asn Asp His Ser Tyr Pro Leu Thr
1               5

<210> SEQ ID NO 33
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 33

Gln Gln Tyr Tyr Ser Tyr Pro Tyr Thr
1               5

<210> SEQ ID NO 34
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 34

Gln Gln Tyr Tyr Thr Tyr Pro Tyr Thr
1               5

<210> SEQ ID NO 35
<211> LENGTH: 9
<212> TYPE: PRT
<213> ORGANISM: Artificial Sequence
<220> FEATURE:
<223> OTHER INFORMATION: SYNTHESIZED

```
<400> SEQUENCE: 35

Gln Gln Phe Ser Ser Tyr Pro Tyr Thr
1               5

<210> SEQ ID NO 36
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 36

Gln Gln Phe Ser Asn Tyr Pro Phe Thr
1               5

<210> SEQ ID NO 37
<211> LENGTH: 104
<212> TYPE: PRT
<213> ORGANISM: Artificial Sequence
<220> FEATURE:
<223> OTHER INFORMATION: SYNTHESIZED

<400> SEQUENCE: 37

Lys Gly Val Ser Tyr Ser Leu Cys Thr Ala Ala Phe Thr Phe Thr Lys
1               5                   10                  15

Ile Pro Ala Glu Thr Leu His Gly Thr Val Thr Val Glu Val Gln Tyr
            20                  25                  30

Ala Gly Thr Asp Gly Pro Cys Lys Val Pro Ala Gln Met Ala Val Asp
        35                  40                  45

Met Gln Thr Leu Thr Pro Val Gly Arg Leu Ile Thr Ala Asn Pro Val
    50                  55                  60

Ile Thr Glu Ser Thr Glu Asn Ser Lys Met Met Leu Glu Leu Asp Pro
65                  70                  75                  80

Pro Phe Gly Asp Ser Tyr Ile Val Ile Gly Val Gly Glu Lys Lys Ile
                85                  90                  95

Thr His His Trp His Arg Ser Gly
            100

<210> SEQ ID NO 38
<211> LENGTH: 104
<212> TYPE: PRT
<213> ORGANISM: Artificial Sequence
<220> FEATURE:
<223> OTHER INFORMATION: SYNTHESIZED

<400> SEQUENCE: 38

Lys Gly Val Ser Tyr Ser Leu Cys Thr Ala Ala Phe Thr Phe Thr Lys
1               5                   10                  15

Val Pro Ala Glu Thr Leu His Gly Thr Val Thr Val Glu Val Gln Tyr
            20                  25                  30

Ala Gly Thr Asp Gly Pro Cys Lys Ile Pro Val Gln Met Ala Val Asp
        35                  40                  45

Met Gln Thr Leu Thr Pro Val Gly Arg Leu Ile Thr Ala Asn Pro Val
    50                  55                  60

Ile Thr Glu Ser Thr Glu Asn Ser Lys Met Met Leu Glu Leu Asp Pro
65                  70                  75                  80

Pro Phe Gly Asp Ser Tyr Ile Val Ile Gly Val Gly Asp Lys Lys Ile
                85                  90                  95

Thr His His Trp His Arg Ser Gly
            100
```

<210> SEQ ID NO 39
<211> LENGTH: 104
<212> TYPE: PRT
<213> ORGANISM: Artificial Sequence
<220> FEATURE:
<223> OTHER INFORMATION: SYNTHESIZED

<400> SEQUENCE: 39

```
Lys Gly Thr Thr Tyr Gly Val Cys Ser Lys Ala Phe Lys Phe Leu Gly
1               5                   10                  15

Thr Pro Ala Asp Thr Gly His Gly Thr Val Val Leu Glu Leu Gln Tyr
            20                  25                  30

Thr Gly Thr Asp Gly Pro Cys Lys Val Pro Ile Ser Ser Val Ala Ser
        35                  40                  45

Leu Asn Asp Leu Thr Pro Val Gly Arg Leu Val Thr Asn Pro Phe
50                  55                  60

Val Ser Val Ala Thr Ala Asn Ala Lys Val Leu Ile Glu Leu Glu Pro
65                  70                  75                  80

Pro Phe Gly Asp Ser Tyr Ile Val Val Gly Arg Gly Glu Gln Gln Ile
                85                  90                  95

Asn His His Trp His Lys Ser Gly
            100
```

<210> SEQ ID NO 40
<211> LENGTH: 101
<212> TYPE: PRT
<213> ORGANISM: Artificial Sequence
<220> FEATURE:
<223> OTHER INFORMATION: SYNTHESIZED

<400> SEQUENCE: 40

```
Lys Gly Met Ser Tyr Val Met Cys Thr Gly Ser Phe Lys Leu Glu Lys
1               5                   10                  15

Glu Val Ala Glu Thr Gln His Gly Thr Val Leu Val Gln Val Lys Tyr
            20                  25                  30

Glu Gly Thr Asp Ala Pro Cys Lys Ile Pro Phe Ser Thr Gln Asp Glu
        35                  40                  45

Lys Gly Ala Thr Gln Asn Gly Arg Leu Ile Thr Ala Asn Pro Ile Val
    50                  55                  60

Thr Asp Lys Glu Lys Pro Val Asn Ile Glu Ala Glu Pro Pro Phe Gly
65                  70                  75                  80

Glu Ser Tyr Ile Val Val Gly Ala Gly Glu Lys Ala Leu Lys Leu Ser
                85                  90                  95

Trp Phe Lys Lys Gly
            100
```

<210> SEQ ID NO 41
<211> LENGTH: 101
<212> TYPE: PRT
<213> ORGANISM: Artificial Sequence
<220> FEATURE:
<223> OTHER INFORMATION: SYNTHESIZED

<400> SEQUENCE: 41

```
Lys Gly Met Ser Tyr Val Met Cys Thr Gly Ser Phe Lys Leu Glu Lys
1               5                   10                  15

Glu Val Ala Glu Thr Gln His Gly Thr Val Leu Val Gln Val Lys Tyr
            20                  25                  30
```

```
Glu Gly Thr Asp Ala Pro Cys Lys Ile Pro Phe Ser Ser Gln Asp Glu
            35                  40                  45

Lys Gly Val Thr Gln Asn Gly Arg Leu Ile Thr Ala Asn Pro Ile Val
 50                  55                  60

Thr Asp Lys Glu Lys Pro Val Asn Ile Glu Ala Glu Pro Pro Phe Gly
 65                  70                  75                  80

Glu Ser Tyr Ile Val Val Gly Ala Gly Glu Lys Ala Leu Lys Leu Ser
                 85                  90                  95

Trp Phe Lys Lys Gly
            100

<210> SEQ ID NO 42
<211> LENGTH: 101
<212> TYPE: PRT
<213> ORGANISM: Artificial Sequence
<220> FEATURE:
<223> OTHER INFORMATION: SYNTHESIZED

<400> SEQUENCE: 42

Lys Gly Met Ser Tyr Ser Met Cys Thr Gly Lys Phe Lys Val Val Lys
  1               5                  10                  15

Glu Ile Ala Glu Thr Gln His Gly Thr Ile Val Ile Arg Val Gln Tyr
             20                  25                  30

Glu Gly Asp Gly Ser Pro Cys Lys Ile Pro Phe Glu Ile Met Asp Leu
            35                  40                  45

Glu Lys Arg His Val Leu Gly Arg Leu Ile Thr Val Asn Pro Ile Val
 50                  55                  60

Thr Glu Lys Asp Ser Pro Val Asn Ile Glu Ala Glu Pro Pro Phe Gly
 65                  70                  75                  80

Asp Ser Tyr Ile Ile Ile Gly Val Glu Pro Gly Gln Leu Lys Leu Asn
                 85                  90                  95

Trp Phe Lys Lys Gly
            100

<210> SEQ ID NO 43
<211> LENGTH: 101
<212> TYPE: PRT
<213> ORGANISM: Artificial Sequence
<220> FEATURE:
<223> OTHER INFORMATION: SYNTHESIZED

<400> SEQUENCE: 43

Lys Gly Met Ser Tyr Ala Met Cys Leu Asn Thr Phe Val Leu Lys Lys
  1               5                  10                  15

Glu Val Ser Glu Thr Gln His Gly Thr Ile Leu Ile Lys Val Glu Tyr
             20                  25                  30

Lys Gly Glu Asp Ala Pro Cys Lys Ile Pro Phe Ser Thr Glu Asp Gly
            35                  40                  45

Gln Gly Lys Ala His Asn Gly Arg Leu Ile Thr Ala Asn Pro Val Val
 50                  55                  60

Thr Lys Lys Glu Glu Pro Val Asn Ile Glu Ala Glu Pro Pro Phe Gly
 65                  70                  75                  80

Glu Ser Asn Ile Val Ile Gly Ile Gly Asp Lys Ala Leu Lys Ile Asn
                 85                  90                  95

Trp Tyr Arg Lys Gly
            100

<210> SEQ ID NO 44
```

-continued

```
<211> LENGTH: 101
<212> TYPE: PRT
<213> ORGANISM: Artificial Sequence
<220> FEATURE:
<223> OTHER INFORMATION: SYNTHESIZED

<400> SEQUENCE: 44

Lys Gly Met Ser Tyr Thr Met Cys Ser Gly Lys Phe Ser Ile Asp Lys
1               5                   10                  15

Glu Met Ala Glu Thr Gln His Gly Thr Thr Val Val Lys Val Lys Tyr
            20                  25                  30

Glu Gly Ala Gly Ala Pro Cys Lys Val Pro Ile Glu Ile Arg Asp Val
        35                  40                  45

Asn Lys Glu Lys Val Val Gly Arg Ile Ile Ser Ser Thr Pro Phe Ala
 50                  55                  60

Glu Asn Thr Asn Ser Val Thr Asn Ile Glu Leu Glu Pro Pro Phe Gly
65                  70                  75                  80

Asp Ser Tyr Ile Val Ile Gly Val Gly Asp Ser Ala Leu Thr Leu His
                85                  90                  95

Trp Phe Arg Lys Gly
            100

<210> SEQ ID NO 45
<211> LENGTH: 6
<212> TYPE: PRT
<213> ORGANISM: Zika Virus

<400> SEQUENCE: 45

Thr Ala Ala Phe Thr Phe
1               5

<210> SEQ ID NO 46
<211> LENGTH: 7
<212> TYPE: PRT
<213> ORGANISM: Zika Virus

<400> SEQUENCE: 46

Gln Tyr Ala Gly Thr Asp Gly
1               5

<210> SEQ ID NO 47
<211> LENGTH: 4
<212> TYPE: PRT
<213> ORGANISM: Zika Virus
<220> FEATURE:
<221> NAME/KEY: misc_feature
<222> LOCATION: (2)..(2)
<223> OTHER INFORMATION: Xaa can be any naturally occurring amino acid

<400> SEQUENCE: 47

Ser Xaa Glu Asn
1

<210> SEQ ID NO 48
<211> LENGTH: 5
<212> TYPE: PRT
<213> ORGANISM: Zika Virus

<400> SEQUENCE: 48

Glu Lys Lys Ile Thr
1               5

<210> SEQ ID NO 49
```

```
<211> LENGTH: 5
<212> TYPE: PRT
<213> ORGANISM: Zika Virus

<400> SEQUENCE: 49

Asp Lys Lys Ile Thr
1               5

<210> SEQ ID NO 50
<211> LENGTH: 6
<212> TYPE: PRT
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 50

Tyr Xaa Arg Xaa Xaa Asn
1               5

<210> SEQ ID NO 51
<211> LENGTH: 119
<212> TYPE: PRT
<213> ORGANISM: Artificial Sequence
<220> FEATURE:
<223> OTHER INFORMATION: SYNTHESIZED

<400> SEQUENCE: 51

Gln Val Gln Leu Gln Gln Ser Gly Ala Glu Leu Met Lys Pro Gly Ala
1               5                   10                  15

Ser Val Lys Leu Ser Cys Lys Ala Thr Gly Tyr Thr Phe Thr Gly Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Asn Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Thr Glu Asp Ser Ala Ile Tyr Tyr Cys
                85                  90                  95

Ala Arg Tyr Tyr Tyr Gly Ser Tyr Ala Met Asp Tyr Trp Gly Gln Gly
            100                 105                 110

Thr Ser Val Thr Val Ser Ser
        115

<210> SEQ ID NO 52
<211> LENGTH: 113
<212> TYPE: PRT
<213> ORGANISM: Artificial Sequence
<220> FEATURE:
<223> OTHER INFORMATION: SYNTHESIZED

<400> SEQUENCE: 52

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30
```

```
Gly Asn Gln Lys Asn Tyr Leu Ala Trp Tyr Gln Gln Lys Pro Gly Gln
            35                  40                  45

Pro Pro Lys Leu Leu Ile Tyr Gly Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                85                  90                  95

Asp His Ser Tyr Pro Leu Thr Phe Gly Ala Gly Thr Lys Leu Glu Leu
                100                 105                 110

Lys

<210> SEQ ID NO 53
<211> LENGTH: 117
<212> TYPE: PRT
<213> ORGANISM: Artificial Sequence
<220> FEATURE:
<223> OTHER INFORMATION: SYNTHESIZED

<400> SEQUENCE: 53

Gln Val Gln Leu Gln Gln Pro Gly Ala Glu Leu Val Lys Pro Gly Ala
 1               5                  10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Met Ile His Pro Asn Ser Gly Ser Thr Asn Tyr Asn Glu Lys Phe
 50                  55                  60

Lys Ser Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Phe Tyr Cys
                85                  90                  95

Ala Arg Tyr Tyr Asp Tyr Asp Met Asp Tyr Trp Gly Gln Gly Thr Ser
                100                 105                 110

Val Thr Val Ser Ser
        115

<210> SEQ ID NO 54
<211> LENGTH: 113
<212> TYPE: PRT
<213> ORGANISM: Artificial Sequence
<220> FEATURE:
<223> OTHER INFORMATION: SYNTHESIZED

<400> SEQUENCE: 54

Asp Ile Val Met Thr Gln Ser Pro Ser Ser Leu Ala Met Ser Val Gly
 1               5                  10                  15

Gln Lys Val Thr Met Ser Cys Lys Ser Ser Gln Ser Leu Leu Asn Ser
                20                  25                  30

Ser Asn Gln Lys Asn Tyr Leu Ala Trp Tyr Gln Gln Lys Pro Gly Gln
            35                  40                  45

Ser Pro Lys Leu Leu Val Tyr Phe Ala Ser Thr Arg Glu Ser Gly Val
 50                  55                  60

Pro Asp Arg Phe Ile Gly Ser Gly Ser Gly Thr Asp Phe Thr Leu Thr
 65                  70                  75                  80

Ile Ser Ser Val Gln Ala Glu Asp Leu Ala Asp Tyr Phe Cys Gln Gln
                85                  90                  95
```

His Tyr Ser Thr Pro Tyr Thr Phe Gly Gly Thr Lys Leu Glu Ile
            100                 105                 110

Lys

<210> SEQ ID NO 55
<211> LENGTH: 114
<212> TYPE: PRT
<213> ORGANISM: Artificial Sequence
<220> FEATURE:
<223> OTHER INFORMATION: SYNTHESIZED

<400> SEQUENCE: 55

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Arg Thr Gly Gln Gly Leu Glu Trp Ile
        35                  40                  45

Gly Glu Ile Tyr Pro Arg Ser Gly Asn Thr Tyr Tyr Asn Glu Lys Phe
    50                  55                  60

Lys Gly Lys Ala Thr Leu Thr Ala Asp Lys Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Asn Tyr Gly Ser Tyr Trp Gly Gln Gly Thr Thr Leu Thr Val
            100                 105                 110

Ser Ser

<210> SEQ ID NO 56
<211> LENGTH: 107
<212> TYPE: PRT
<213> ORGANISM: Artificial Sequence
<220> FEATURE:
<223> OTHER INFORMATION: SYNTHESIZED

<400> SEQUENCE: 56

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys
            100                 105